US011142750B2

(12) United States Patent
Smith et al.

(10) Patent No.: US 11,142,750 B2
(45) Date of Patent: Oct. 12, 2021

(54) OPTIMIZED ENGINEERED MEGANUCLEASES HAVING SPECIFICITY FOR A RECOGNITION SEQUENCE IN THE HEPATITIS B VIRUS GENOME

(71) Applicant: Precision BioSciences, Inc., Durham, NC (US)

(72) Inventors: James Jefferson Smith, Morrisville, NC (US); Janel Lape, Wake Forest, NC (US); Victor Bartsevich, Durham, NC (US); Hui Li, Apex, NC (US)

(73) Assignee: Precision BioSciences, Inc., Durham, NC (US)

( * ) Notice: Subject to any disclaimer, the term of this patent is extended or adjusted under 35 U.S.C. 154(b) by 111 days.

(21) Appl. No.: 16/381,668

(22) Filed: Apr. 11, 2019

(65) Prior Publication Data
US 2019/0338263 A1   Nov. 7, 2019

Related U.S. Application Data

(60) Provisional application No. 62/656,831, filed on Apr. 12, 2018.

(51) Int. Cl.
| C12N 9/22 | (2006.01) |
| A61K 47/69 | (2017.01) |
| A61K 9/16 | (2006.01) |
| C12N 15/86 | (2006.01) |
| C12N 15/85 | (2006.01) |

(52) U.S. Cl.
CPC .............. *C12N 9/22* (2013.01); *A61K 9/1617* (2013.01); *A61K 47/6929* (2017.08); *C12N 15/86* (2013.01); *C12N 2015/8518* (2013.01)

(58) Field of Classification Search
CPC .. C12N 9/22; C12N 15/86; C12N 2015/8518; C12N 2310/20; A61K 47/6929; A61K 9/1617; C12Y 301/21001
See application file for complete search history.

(56) References Cited

U.S. PATENT DOCUMENTS

| 4,873,192 | A | 10/1989 | Kunkel |
| 6,015,832 | A | 1/2000 | Baker, Jr. et al. |
| 6,506,803 | B1 | 1/2003 | Baker, Jr. et al. |
| 6,559,189 | B2 | 5/2003 | Baker, Jr. et al. |
| 6,635,676 | B2 | 10/2003 | Baker, Jr. et al. |
| 7,074,596 | B2 | 7/2006 | Darzynkiewicz et al. |
| 7,672,016 | B2 | 3/2010 | Kaneko et al. |
| 8,021,867 | B2 | 9/2011 | Smith et al. |
| 8,278,036 | B2 | 10/2012 | Kariko et al. |
| 8,445,251 | B2 | 5/2013 | Smith et al. |
| 8,513,184 | B2 | 8/2013 | Appleby et al. |
| 8,722,054 | B2 | 5/2014 | Apelian et al. |
| 9,181,288 | B2 | 11/2015 | Hartman et al. |
| 9,186,337 | B2 | 11/2015 | Baker et al. |
| 9,340,777 | B2 | 5/2016 | Smith et al. |
| 9,434,931 | B2 | 9/2016 | Smith et al. |
| 9,670,205 | B2 | 6/2017 | Aktoudianakis et al. |
| 9,884,866 | B2 | 2/2018 | Feguson et al. |
| 10,041,053 | B2 | 8/2018 | Smith et al. |
| 10,851,358 | B2 | 12/2020 | Jantz et al. |
| 2002/0045667 | A1 | 4/2002 | Baker, Jr. et al. |
| 2004/0043041 | A1 | 3/2004 | Baker, Jr. et al. |
| 2008/0234251 | A1 | 9/2008 | Doherty et al. |
| 2008/0306050 | A1 | 12/2008 | Doherty et al. |
| 2009/0047249 | A1 | 2/2009 | Graupe et al. |
| 2010/0015178 | A1 | 1/2010 | Combs et al. |
| 2010/0029585 | A1 | 2/2010 | Howbert et al. |
| 2010/0143301 | A1 | 6/2010 | Desai et al. |
| 2011/0092485 | A1 | 4/2011 | Howbert et al. |
| 2011/0098248 | A1 | 4/2011 | Halcomb et al. |
| 2011/0118235 | A1 | 5/2011 | Howbert et al. |
| 2012/0082658 | A1 | 4/2012 | Hershberg |
| 2012/0171191 | A1 | 7/2012 | Choulika et al. |
| 2012/0219615 | A1 | 8/2012 | Hershberg et al. |
| 2013/0079327 | A1 | 3/2013 | Yamamoto et al. |
| 2013/0217880 | A1 | 8/2013 | Yamamoto et al. |
| 2013/0251673 | A1 | 9/2013 | Hartman et al. |
| 2013/0267517 | A1 | 10/2013 | Guo et al. |
| 2013/0344029 | A1 | 12/2013 | Aciro et al. |
| 2013/0344030 | A1 | 12/2013 | Steadman et al. |
| 2014/0030221 | A1 | 1/2014 | Aciro et al. |

(Continued)

FOREIGN PATENT DOCUMENTS

| JP | 2009-511085 A | 3/2009 |
| JP | 2011-501971 A | 1/2011 |

(Continued)

OTHER PUBLICATIONS

U.S. Appl. No. 16/342,169, filed Apr. 15, 2019, Jantz et al.
PCT/US2017/056638, Jan. 31, 2018, Invitation to Pay Additional Fees.
PCT/US2017/056638, Apr. 9, 2018, International Search Report and Written Opinion.
PCT/US2017/056638, Apr. 25, 2019, International Preliminary Report on Patentability.
PCT/US2019/027203, Jul. 16, 2019, International Search Report and Written Opinion.

(Continued)

*Primary Examiner* — Delia M Ramirez
(74) *Attorney, Agent, or Firm* — Wolf, Greenfield & Sacks, P.C.

(57) ABSTRACT

The present invention encompasses engineered nucleases which recognize and cleave a recognition sequence within a Hepatitis B virus (HBV) genome. The engineered meganucleases can exhibit at least one optimized characteristic, such as enhanced specificity and/or efficiency of indel formation, when compared to the first-generation meganuclease HBV 11-12x.26. Further, the invention encompasses pharmaceutical compositions comprising engineered meganuclease proteins, nucleic acids encoding engineered meganucleases, and the use of such compositions for treating HBV infections or hepatocellular carcinoma.

6 Claims, 17 Drawing Sheets

Specification includes a Sequence Listing.

(56) References Cited

U.S. PATENT DOCUMENTS

| | | |
|---|---|---|
| 2014/0045849 A1 | 2/2014 | McGowan et al. |
| 2014/0066432 A1 | 3/2014 | Howbert et al. |
| 2014/0073642 A1 | 3/2014 | McGowan et al. |
| 2014/0088085 A1 | 3/2014 | Burgess et al. |
| 2014/0171432 A1 | 6/2014 | Kanouni et al. |
| 2014/0178337 A1 | 6/2014 | Hartman et al. |
| 2014/0179005 A1 | 6/2014 | Jantz et al. |
| 2014/0194469 A1 | 7/2014 | Nie et al. |
| 2014/0213591 A1 | 7/2014 | Chen et al. |
| 2014/0275084 A1 | 9/2014 | Kanouni et al. |
| 2014/0275092 A1 | 9/2014 | Albrecht et al. |
| 2014/0275167 A1 | 9/2014 | Hartman |
| 2014/0330015 A1 | 11/2014 | Yamamoto et al. |
| 2014/0343032 A1 | 11/2014 | Guo et al. |
| 2014/0350031 A1 | 11/2014 | McGowan et al. |
| 2014/0371195 A1 | 12/2014 | Labelle et al. |
| 2014/0371214 A1 | 12/2014 | Labelle et al. |
| 2015/0031687 A1 | 1/2015 | Guo et al. |
| 2015/0132258 A1 | 5/2015 | Hartman |
| 2015/0197533 A1 | 7/2015 | Hartman et al. |
| 2015/0210682 A1 | 7/2015 | Han et al. |
| 2015/0225355 A1 | 8/2015 | Hartman |
| 2015/0252057 A1 | 9/2015 | Guo et al. |
| 2015/0259324 A1 | 9/2015 | Hartman et al. |
| 2015/0274652 A1 | 10/2015 | Hartman |
| 2015/0315159 A1 | 11/2015 | Hartman |
| 2015/0368670 A1 | 12/2015 | Quake et al. |
| 2016/0039808 A1 | 2/2016 | Kanouni et al. |
| 2016/0102096 A1 | 4/2016 | Boesen et al. |
| 2016/0122344 A1 | 5/2016 | Han et al. |
| 2016/0137652 A1 | 5/2016 | Beck et al. |
| 2016/0176899 A1 | 6/2016 | Schwitter et al. |
| 2016/0220586 A1 | 8/2016 | Andre et al. |
| 2016/0237090 A1 | 8/2016 | Hu et al. |
| 2016/0289229 A1 | 10/2016 | Aktoudianakis et al. |
| 2017/0044206 A1 | 2/2017 | Altman et al. |
| 2017/0121328 A1 | 5/2017 | Hartman et al. |
| 2017/0121329 A1 | 5/2017 | Hartman et al. |
| 2017/0158724 A1 | 6/2017 | Adams et al. |
| 2017/0334882 A1 | 11/2017 | Hartman et al. |
| 2017/0334898 A9 | 11/2017 | Guo et al. |
| 2018/0030053 A1 | 2/2018 | Fu et al. |
| 2018/0065929 A1 | 3/2018 | Vandyck et al. |
| 2018/0065938 A1 | 3/2018 | Chin et al. |
| 2018/0086755 A1 | 3/2018 | Chin et al. |
| 2019/0017075 A1 | 1/2019 | Bartsevich et al. |
| 2019/0142973 A1 | 5/2019 | Jantz et al. |
| 2019/0284543 A1 | 9/2019 | Jantz et al. |
| 2019/0338263 A1 | 11/2019 | Smith et al. |

FOREIGN PATENT DOCUMENTS

| | | |
|---|---|---|
| JP | 6811857 B2 | 1/2021 |
| WO | WO 93/13120 A1 | 7/1993 |
| WO | WO 2002/012514 A2 | 2/2002 |
| WO | WO 2007/047859 A2 | 4/2007 |
| WO | WO 2008/005555 A1 | 1/2008 |
| WO | WO 2009/001159 A1 | 12/2008 |
| WO | WO 2009/059195 A2 | 5/2009 |
| WO | WO 2009/086558 A1 | 7/2009 |
| WO | WO 2010/136841 A2 | 12/2010 |
| WO | WO 2011/161699 A2 | 12/2011 |
| WO | WO 2012/167192 A2 | 12/2012 |
| WO | WO 2012/168944 A1 | 12/2012 |
| WO | WO 2013/096744 A1 | 6/2013 |
| WO | WO 2013/132317 A1 | 9/2013 |
| WO | WO 2013/144129 A1 | 10/2013 |
| WO | WO 2013/144704 A1 | 10/2013 |
| WO | WO 2013/159109 A1 | 10/2013 |
| WO | WO 2013/173223 A1 | 11/2013 |
| WO | WO 2014/023813 A1 | 2/2014 |
| WO | WO 2014/033167 A1 | 3/2014 |
| WO | WO 2014/033170 A1 | 3/2014 |
| WO | WO 2014/033176 A1 | 3/2014 |
| WO | WO 2014/037480 A1 | 3/2014 |
| WO | WO 2014/056953 A1 | 4/2014 |
| WO | WO 2014/076221 A1 | 5/2014 |
| WO | WO 2014/128189 A1 | 8/2014 |
| WO | WO 2014/131847 A1 | 9/2014 |
| WO | WO 2014/151634 A1 | 9/2014 |
| WO | WO 2014/161888 A1 | 10/2014 |
| WO | WO 2014/164708 A1 | 10/2014 |
| WO | WO 2014/179760 A1 | 11/2014 |
| WO | WO 2014/184350 A1 | 11/2014 |
| WO | WO 2014/184365 A1 | 11/2014 |
| WO | WO 2015/011281 A1 | 1/2015 |
| WO | WO 2015/014815 A1 | 2/2015 |
| WO | WO 2015/019284 A2 | 2/2015 |
| WO | WO 2015/023958 A1 | 2/2015 |
| WO | WO 2015/033299 A1 | 3/2015 |
| WO | WO 2015/033301 A1 | 3/2015 |
| WO | WO 2015/033303 A1 | 3/2015 |
| WO | WO 2015/034820 A1 | 3/2015 |
| WO | WO 2015/036927 A1 | 3/2015 |
| WO | WO 2015/044900 A1 | 4/2015 |
| WO | WO 2015/057655 A1 | 4/2015 |
| WO | WO 2015/057659 A1 | 4/2015 |
| WO | WO 2015/059212 A1 | 4/2015 |
| WO | WO 2015/088045 A1 | 6/2015 |
| WO | WO 2015/095780 A1 | 6/2015 |
| WO | WO 2015/118057 A1 | 8/2015 |
| WO | WO 2015/119944 A1 | 8/2015 |
| WO | WO 2015/134605 A1 | 9/2015 |
| WO | WO 2015/160641 A2 | 10/2015 |
| WO | WO 2015/162075 A1 | 10/2015 |
| WO | WO 2015/168269 A1 | 11/2015 |
| WO | WO 2015/168279 A1 | 11/2015 |
| WO | WO 2015/173164 A1 | 11/2015 |
| WO | WO 2015/179615 A1 | 11/2015 |
| WO | WO 2015/188085 A1 | 12/2015 |
| WO | WO 2016/012470 A1 | 1/2016 |
| WO | WO 2016/019232 A1 | 2/2016 |
| WO | WO 2016/023511 A1 | 2/2016 |
| WO | WO 2016/023877 A1 | 2/2016 |
| WO | WO 2016/029077 A1 | 2/2016 |
| WO | WO 2016/039749 A1 | 3/2016 |
| WO | WO 2016/055553 A1 | 4/2016 |
| WO | WO 2016/057624 A1 | 4/2016 |
| WO | WO 2016/057924 A1 | 4/2016 |
| WO | WO 2016/073738 A2 | 5/2016 |
| WO | WO 2016/075661 A1 | 5/2016 |
| WO | WO 2016/077518 A1 | 5/2016 |
| WO | WO 2016/091698 A1 | 6/2016 |
| WO | WO 2016/096778 A1 | 6/2016 |
| WO | WO 2016/100285 A1 | 6/2016 |
| WO | WO 2016/100608 A1 | 6/2016 |
| WO | WO 2016/102438 A1 | 6/2016 |
| WO | WO 2016/107536 A1 | 7/2016 |
| WO | WO 2016/107832 A1 | 7/2016 |
| WO | WO 2016/107833 A1 | 7/2016 |
| WO | WO 2016/120186 A1 | 8/2016 |
| WO | WO 2016/126646 A1 | 8/2016 |
| WO | WO 2016/128335 A1 | 8/2016 |
| WO | WO 2016/141092 A1 | 9/2016 |
| WO | WO 2016/142250 A1 | 9/2016 |
| WO | WO 2016/142833 A1 | 9/2016 |
| WO | WO 2016/142835 A1 | 9/2016 |
| WO | WO 2016/142852 A1 | 9/2016 |
| WO | WO 2016/142886 A2 | 9/2016 |
| WO | WO 2016/142894 A1 | 9/2016 |
| WO | WO 2016/149351 A1 | 9/2016 |
| WO | WO 2016/161268 A1 | 10/2016 |
| WO | WO 2016/168619 A1 | 10/2016 |
| WO | WO 2016/177655 A1 | 11/2016 |
| WO | WO 2016/180743 A1 | 11/2016 |
| WO | WO 2016/195982 A2 | 12/2016 |
| WO | WO 2017/001307 A1 | 1/2017 |
| WO | WO 2017/001655 A1 | 1/2017 |
| WO | WO 2017/001853 A1 | 1/2017 |
| WO | WO 2017/007701 A1 | 1/2017 |
| WO | WO 2017/013046 A1 | 1/2017 |
| WO | WO 2017/016960 A1 | 2/2017 |
| WO | WO 2017/017042 A1 | 2/2017 |
| WO | WO 2017/017043 A1 | 2/2017 |

(56) References Cited

FOREIGN PATENT DOCUMENTS

| | | |
|---|---|---|
| WO | WO 2017/017624 A1 | 2/2017 |
| WO | WO 2017/027434 A1 | 2/2017 |
| WO | WO 2017/034986 A1 | 3/2017 |
| WO | WO 2017/038909 A1 | 3/2017 |
| WO | WO 2017/040233 A1 | 3/2017 |
| WO | WO 2017/046112 A1 | 3/2017 |
| WO | WO 2017/047769 A1 | 3/2017 |
| WO | WO 2017/048950 A1 | 3/2017 |
| WO | WO 2017/048954 A1 | 3/2017 |
| WO | WO 2017/048962 A1 | 3/2017 |
| WO | WO 2017/061466 A1 | 4/2017 |
| WO | WO 2017/061532 A1 | 4/2017 |
| WO | WO 2017/066227 A1 | 4/2017 |
| WO | WO 2017/070089 A1 | 4/2017 |
| WO | WO 2017/176608 A1 | 4/2017 |
| WO | WO 2017/075477 A1 | 5/2017 |
| WO | WO 2017/076346 A1 | 5/2017 |
| WO | WO 2017/076988 A1 | 5/2017 |
| WO | WO 2017/079669 A1 | 5/2017 |
| WO | WO 2017/087678 A2 | 5/2017 |
| WO | WO 2017/087777 A1 | 5/2017 |
| WO | WO 2017/100108 A1 | 6/2017 |
| WO | WO 2017/106607 A1 | 6/2017 |
| WO | WO 2017/106634 A1 | 6/2017 |
| WO | WO 2017/106740 A1 | 6/2017 |
| WO | WO 2017/112730 A1 | 6/2017 |
| WO | WO 2017/161349 A1 | 9/2017 |
| WO | WO 2017/163264 A1 | 9/2017 |
| WO | WO 2017/184735 A1 | 10/2017 |
| WO | WO 2017/184746 A1 | 10/2017 |
| WO | WO 2017/186711 A1 | 11/2017 |
| WO | WO 2017/190669 A1 | 11/2017 |
| WO | WO 2017/192741 A1 | 11/2017 |
| WO | WO 2017/192961 A1 | 11/2017 |
| WO | WO 2017/198744 A1 | 11/2017 |
| WO | WO 2017/202703 A1 | 11/2017 |
| WO | WO 2017/202704 A1 | 11/2017 |
| WO | WO 2017/202798 A1 | 11/2017 |
| WO | WO 2017/205464 A1 | 11/2017 |
| WO | WO 2017/211791 A1 | 12/2017 |
| WO | WO 2017/214395 A1 | 12/2017 |
| WO | WO 2017/216054 A1 | 12/2017 |
| WO | WO 2017/216685 A1 | 12/2017 |
| WO | WO 2017/216686 A1 | 12/2017 |
| WO | WO 2017/219931 A1 | 12/2017 |
| WO | WO 2017/222976 A1 | 12/2017 |
| WO | WO 2018/001944 A1 | 1/2018 |
| WO | WO 2018/001952 A1 | 1/2018 |
| WO | WO 2018/002319 A1 | 1/2018 |
| WO | WO 2018/004163 A1 | 1/2018 |
| WO | WO 2018/005586 A1 | 1/2018 |
| WO | WO 2018/005881 A1 | 1/2018 |
| WO | WO 2018/005883 A1 | 1/2018 |
| WO | WO 2018/009466 A1 | 1/2018 |
| WO | WO 2018/009505 A1 | 1/2018 |
| WO | WO 2018/011100 A1 | 1/2018 |
| WO | WO 2018/011160 A1 | 1/2018 |
| WO | WO 2018/011162 A1 | 1/2018 |
| WO | WO 2018/011163 A1 | 1/2018 |
| WO | WO 2018/013789 A1 | 1/2018 |
| WO | WO 2018/019297 A1 | 2/2018 |
| WO | WO 2018/022282 A1 | 2/2018 |
| WO | WO 2018/026620 A1 | 2/2018 |
| WO | WO 2018/026971 A1 | 2/2018 |
| WO | WO 2018/031434 A1 | 2/2018 |
| WO | WO 2018/036941 A1 | 3/2018 |
| WO | WO 2018/038877 A1 | 3/2018 |
| WO | WO 2018/043747 A1 | 3/2018 |
| WO | WO 2018/044783 A1 | 3/2018 |
| WO | WO 2018/044963 A1 | 3/2018 |
| WO | WO 2018/045144 A1 | 3/2018 |
| WO | WO 2018/045150 A1 | 3/2018 |
| WO | WO 2018/045911 A1 | 3/2018 |
| WO | WO 2018/046460 A1 | 3/2018 |
| WO | WO 2018/047081 A1 | 3/2018 |
| WO | WO 2018/049089 A1 | 3/2018 |
| WO | WO 2018/051254 A1 | 3/2018 |
| WO | WO 2018/051255 A1 | 3/2018 |
| WO | WO 2018/060323 A1 | 4/2018 |
| WO | WO 2018/065360 A1 | 4/2018 |
| WO | WO 2018/067423 A1 | 4/2018 |
| WO | WO 2018/071849 A2 | 4/2018 |
| WO | WO 2018/073754 A1 | 4/2018 |
| WO | WO 2018/078149 A1 | 5/2018 |
| WO | WO 2018/080903 A1 | 5/2018 |
| WO | WO 2018/085750 A2 | 5/2018 |
| WO | WO 2018/086593 A1 | 5/2018 |
| WO | WO 2018/089695 A1 | 5/2018 |
| WO | WO 2018/095426 A1 | 5/2018 |
| WO | WO 2018/098203 A1 | 5/2018 |
| WO | WO 2018/100558 A2 | 6/2018 |
| WO | WO 2018/118664 A1 | 6/2018 |
| WO | WO 2018/118665 A1 | 6/2018 |
| WO | WO 2018/118826 A1 | 6/2018 |
| WO | WO 2018/118848 A1 | 6/2018 |
| WO | WO 2018/119013 A1 | 6/2018 |
| WO | WO 2018/119221 A1 | 6/2018 |
| WO | WO 2018/119236 A1 | 6/2018 |
| WO | WO 2018/119263 A1 | 6/2018 |
| WO | WO 2018/119266 A1 | 6/2018 |
| WO | WO 2018/119286 A1 | 6/2018 |

OTHER PUBLICATIONS

PCT/US/2019/027203, Oct. 22, 2020, International Preliminary Report on Patentability.

Invitation to Pay Additional Fees for Application No. PCT/US2017/056638 dated Jan. 31, 2018.

International Search Report and Written Opinion for Application No. PCT/US2017/056638 dated Apr. 9, 2018.

International Preliminary Report on Patentability for Application No. PCT/US2017/056638 dated Apr. 25, 2019.

International Search Report and Written Opinion for Application No. PCT/US2019/027203 dated Jul. 16, 2019.

International Preliminary Report on Patentability for Application No. PCT/US2019/027203 dated Oct. 22, 2020.

Airenne et al., Baculovirus: an insect-derived vector for diverse gene transfer applications. Mol Ther. Apr. 2013;21(4):739-49. doi: 10.1038/mt.2012.286. Epub Feb. 26, 2013.

Altschul et al., Basic local alignment search tool. J Mol Biol. Oct. 5, 1990;215(3):403-10.

Altschul et al., Gapped BLAST and PSI-BLAST: a new generation of protein database search programs. Nucleic Acids Res. Sep. 1, 1997;25(17):3389-402.

Arnould et al., Engineering of large numbers of highly specific homing endonucleases that induce recombination on novel DNA targets. J Mol Biol. Jan. 20, 2006;355(3):443-58. Epub Nov. 15, 2005.

Benoist et al., In vivo sequence requirements of the SV40 early promotor region. Nature. Mar. 26, 1981;290(5804):304-10.

Bloom et al., Inactivation of hepatitis B virus replication in cultured cells and in vivo with engineered transcription activator-like effector nucleases. Mol Ther. Oct. 2013;21(10):1889-97. doi: 10.1038/mt.2013.170. Epub Jul. 25, 2013.

Cahill et al., Mechanisms of eukaryotic DNA double strand break repair. Front Biosci. May 1, 2006;11:1958-76.

Chames et al., In vivo selection of engineered homing endonucleases using double-strand break induced homologous recombination. Nucleic Acids Res. Nov. 23, 2005;33(20):e178.

Chang et al., Inducible retroviral vectors regulated by lac repressor in mammalian cells. Gene. Dec. 12, 1996;183(1-2):137-42.

Chen et al., A novel adenoviral vector carrying an all-in-one Tet-On system with an autoregulatory loop for tight, inducible transgene expression. BMC Biotechnol. Feb. 13, 2015;15:4. doi: 10.1186/s12896-015-0121-4.

Chen, Exploiting the Intron-splicing Mechanism of Insect Cells to Produce Viral Vectors Harboring Toxic Genes for Suicide Gene Therapy. Mol Ther Nucleic Acids. Nov. 27, 2012;1:e57. doi: 10.1038/mtna.2012.48.

(56) References Cited

OTHER PUBLICATIONS

Cheng et al., Dendrimers as drug carriers: applications in different routes of drug administration. J Pharm Sci. Jan. 2008;97(1):123-43.
Cheng et al., Multifactorial heterogeneity of virus-specific T cells and association with the progression of human chronic hepatitis B infection. Sci Immunol. Feb. 8, 2019; 4(32). pii: eaau6905. doi: 10.1126/sciimmunol.aau6905.
Chevalier et al., Homing endonucleases: structural and functional insight into the catalysts of intron/intein mobility. Nucleic Acids Res. Sep. 15, 2001;29(18):3757-74.
Cots et al., Helper dependent adenovirus vectors: progress and future prospects. Curr Gene Ther. Oct. 2013;13(5):370-81.
Deshayes et al., Cell-penetrating peptides: tools for intracellular delivery of therapeutics. Cell Mol Life Sci. Aug. 2005;62(16):1839-49.
Deshayes et al., Primary amphipathic cell-penetrating peptides: structural requirements and interactions with model membranes. Biochemistry. Jun. 22, 2004;43(24):7698-706.
Dinda et al., Nanobiotechnology-based drug delivery in brain targeting. Curr Pharm Biotechnol. 2013;14(15):1264-74.
Dingermann et al., Establishment of a system for conditional gene expression using an inducible tRNA suppressor gene. Mol Cell Biol. Sep. 1992;12(9):4038-45.
Gao et al., Efficient gene delivery into mammalian cells mediated by a recombinant baculovirus containing a whispovirus ie1 promoter, a novel shuttle promoter between insect cells and mammalian cells. J Biotechnol. Aug. 31, 2007;131(2):138-43. Epub Jun. 19, 2007.
Gish et al., Identification of protein coding regions by database similarity search. Nat Genet. Mar. 1993;3(3):266-72.
Grizot et al., Efficient targeting of a SCID gene by an engineered single-chain homing endonuclease. Nucleic Acids Res. Sep. 2009;37(16):5405-19. doi: 10.1093/nar/gkp548. Epub Jul. 7, 2009.
Haase et al., Generation of a tumor- and tissue-specific episomal non-viral vector system. BMC Biotechnol. Jun. 4, 2013;13:49. doi: 10.1186/1472-6750-13-49.
Hudecz et al., Medium-sized peptides as built in carriers for biologically active compounds. Med Res Rev. Nov. 2005;25(6):679-736.
Jacox et al., Tissue-specific and ubiquitous expression patterns from alternative promoters of human genes. PLoS One. Aug. 18, 2010;5(8):e12274. doi: 10.1371/journal.pone.0012274.
Jearawiriyapaisam et al., Sustained dystrophin expression induced by peptide-conjugated morpholino oligomers in the muscles of mdx mice. Mol Ther. Sep. 2008;16(9):1624-9. doi: 10.1038/mt.2008.120. Epub Jun. 10, 2008.
Jiang et al., Cationic core-shell liponanoparticles for ocular gene delivery. Biomaterials. Oct. 2012;33(30):7621-30. doi: 10.1016/j.biomaterials.2012.06.079. Epub Jul. 11, 2012.
Kang Derwent et al., Thermoresponsive hydrogels as a new ocular drug delivery platform to the posterior segment of the eye. Trans Am Ophthalmol Soc. 2008;106:206-13; discussion 213-4.
Kang et al., Harnessing the capacity of cell-penetrating peptides for drug delivery to the central nervous system. Curr Pharm Biotechnol. 2014;15(3):220-30.
Kramer et al., In vitro and in vivo comparative study of chimeric liver-specific promoters. Mol Ther. Mar. 2003;7(3):375-85.
Kunkel et al., Rapid and efficient site-specific mutagenesis without phenotypic selection. Methods Enzymol. 1987;154:367-82.
Kunkel, Rapid and efficient site-specific mutagenesis without phenotypic selection. Proc Natl Acad Sci U S A. Jan. 1985;82(2):488-92.
Ladner et al., Inducible expression of human hepatitis B virus (HBV) in stably transfected hepatoblastoma cells: a novel system for screening potential inhibitors of HBV replication. Antimicrob Agents Chemother. Aug. 1997; 41(8):1715-20.
Lentz et al., Viral vectors for gene delivery to the central nervous system. Neurobiol Dis. Nov. 2012;48(2):179-88. doi: 10.1016/j.nbd.2011.09.014. Epub Oct. 7, 2011.
Li et al., Generation of single-chain LAGLIDADG homing endonucleases from native homodimeric precursor proteins. Nucleic Acids Res. Apr. 2009;37(5):1650-62. doi: 10.1093/nar/gkp004. Epub Jan. 19, 2009.
Lin et al., The CRISPR/Cas9 system facilitates clearance of the intrahepatic HBV templates in vivo. Mol Ther Nucleic Acids. Aug. 19, 2014;3(8):e186. doi: 10.1038/mtna.2014.38.
Liu et al., Therapeutic levels of factor IX expression using a muscle-specific promoter and adeno-associated virus serotype 1 vector. Hum Gene Ther. Aug. 2004;15(8):783-92.
Low et al., Binding of TCR multimers and a TCR-like antibody with distinct fine-specificities is dependent on the surface density of HLA complexes. PLoS One. 2012; 7(12):e51397. doi: 10.1371/journal.pone.0051397. Epub Dec. 10, 2012.
Madden et al., Applications of network BLAST server. Methods Enzymol. 1996;266:131-41.
Martin et al., Gene delivery to the eye using adeno-associated viral vectors. Methods. Oct. 2002;28(2):267-75.
Mastorakos et al., Hydroxyl PAMAM dendrimer-based gene vectors for transgene delivery to human retinal pigment epithelial cells. Nanoscale. Mar. 7, 2015;7(9):3845-56. doi: 10.1039/c4nr04284k.
McCall et al., Pathogen-inspired drug delivery to the central nervous system. Tissue Barriers. Aug. 8, 2014;2(4):e944449. doi: 10.4161/21688362.2014.944449. eCollection 2014.
McCarty et al., Self-complementary recombinant adeno-associated virus (scAAV) vectors promote efficient transduction independently of DNA synthesis. Gene Ther. Aug. 2001;8(16):1248-54.
Mishra et al., Recent applications of liposomes in ophthalmic drug delivery. J Drug Deliv. 2011;2011:863734. doi: 10.1155/2011/863734. Epub Mar. 1, 2011.
Qian et al., Improved brain uptake of peptide-based CNS drugs via alternative routes of administrations of its nanocarrier delivery systems: a promising strategy for CNS targeting delivery of peptides. Expert Opin Drug Metab Toxicol. Nov. 2014;10(11):1491-508. doi: 10.1517/17425255.2014.956080. Epub Sep. 6, 2014.
Sands, AAV-mediated liver-directed gene therapy. Methods Mol Biol. 2011;807:141-57. doi: 10.1007/978-1-61779-370-7_6.
Sastry et al., Targeting hepatitis B virus-infected cells with a T-cell receptor-like antibody. J Virol. Mar. 2011; 85(5):1935-42. doi: 10.1128/JVI.01990-10. Epub Dec. 15, 2010.
Seligman et al., Mutations altering the cleavage specificity of a homing endonuclease. Nucleic Acids Res. Sep. 1, 2002;30(17):3870-9.
Sharma et al., Formulation and optimization of polymeric nanoparticles for intranasal delivery of lorazepam using Box-Behnken design: in vitro and in vivo evaluation. Biomed Res Int. 2014;2014:156010. doi: 10.1155/2014/156010. Epub Jul. 14, 2014.
Shen et al., Frequency and reactivity of antigen-specific T cells were concurrently measured through the combination of artificial antigen-presenting cell, MACS and ELISPOT. Sci Rep. Nov. 27, 2017; 7(1):16400. doi: 10.1038/s41598-017-16549-1.
Simeoni et al., Insight into the mechanism of the peptide-based gene delivery system MPG: implications for delivery of siRNA into mammalian cells. Nucleic Acids Res. Jun. 1, 2003;31(11):2717-24.
Sowa et al., In vitro and in vivo testing of a novel regulatory system for gene therapy for intervertebral disc degeneration. Spine (Phila Pa 1976). May 1, 2011;36(10):E623-8. doi: 10.1097/BRS.0b013e3181ed11c1.
Stoddard, Homing endonuclease structure and function. Q Rev Biophys. Feb. 2005;38(1):49-95. Epub Dec. 9, 2005.
Sussman et al., Isolation and characterization of new homing endonuclease specificities at individual target site positions. J Mol Biol. Sep. 3, 2004;342(1):31-41.
Tamboli et al., Polymeric vectors for ocular gene delivery. Ther Deliv. Apr. 2011;2(4):523-36. doi: 10.4155/tde.11.20. Author manuscript.
Thomsen et al., Promoter-regulatory region of the major immediate early gene of human cytomegalovirus. Proc Natl Acad Sci U S A. Feb. 1984;81(3):659-63.
Tong et al., Eye drop delivery of nano-polymeric micelle formulated genes with cornea-specific promoters. J Gene Med. Nov. 2007;9(11):956-66.

(56) References Cited

OTHER PUBLICATIONS

Vannucci et al., Viral vectors: a look back and ahead on gene transfer technology. New Microbiol. Jan. 2013;36(1):1-22. Epub Jan. 1, 2013.

Weber et al., AAV-mediated delivery of zinc finger nucleases targeting hepatitis B virus inhibits active replication. PLoS One. May 14, 2014;9(5):e97579. doi: 10.1371/journal.pone.0097579.

Yuasa et al., Adeno-associated virus vector-mediated gene transfer into dystrophin-deficient skeletal muscles evokes enhanced immune response against the transgene product. Gene Ther. Dec. 2002;9(23):1576-88.

Zhang et al., A greedy algorithm for aligning DNA sequences. J Comput Biol. Feb.-Apr. 2000;7(1-2):203-14.

Zhao et al., Nonstimulatory peptide-MHC enhances human T-cell antigen-specific responses by amplifying proximal TCR signaling. Nat Commun. Jul. 13, 2018; 9(1):2716. doi: 10.1038/s41467-018-05288-0.

Zhu et al., Quantum dot/pMHC multimers vs. phycoerythrin/pMHC tetramers for identification of HLA-A*0201-restricted pHBV core antigen18-27-specific T cells. Mol Med Rep. Dec. 2017; 16(6):8605-8612. doi: 10.3892/mmr.2017.7126. Epub Aug. 1, 2017.

Zischewski et al., Detection of on-target and off-target mutations generated by CRISPR/Cas9 and other sequence-specific nucleases. Biotechnol Adv. Jan.-Feb. 2017;35(1):95-104. doi: 10.1016/j.biotechadv.2016.12.003. Epub Dec. 21, 2016.

Zuris et al., Cationic lipid-mediated delivery of proteins enables efficient protein-based genome editing in vitro and in vivo. Nat Biotechnol. Jan. 2015;33(1):73-80. doi: 10.1038/nbt.3081. Epub Oct. 30, 2014.

Silva et al., Meganucleases and Other Tools for Targeted Genome Engineering: Perspectives and Challenges for Gene Therapy. Curr Gene Ther. Feb. 2011;11(1):11-27. doi: 10.2174/156652311794520111.

```
                       HBV11           HBV12
                     Half-Site       Half-Site
HBV 11-12            TGCCGATCCATAC TGCGGAACT     SEQ ID NO:10
Recognition Sequence ACGGCTAGG TATGACGCCTTGA     SEQ ID NO:11
```

FIGURE 2

| HBV 11-12 | 1259-1280 of SEQ ID NO: 3 | SEQ ID NO: |
|---|---|---|
| Genotype A | TGCCGATCCATACTGCGGAACT | 10 |
| Genotype B | TGCCGATCCATACTGCGGAACT | 10 |
| Genotype C | TGCCGATCCATACTGCGGAACT | 10 |
| Genotype D | TGCCGATCCATACTGCGGAACT | 10 |
| Genotype E | TGCCGATCCATACTGCGGAACT | 10 |
| Genotype F | TGCCGATCCATACTGCGGAACT | 10 |
| Genotype G | TGCCGATCCATACTGCGGAACT | 10 |

1. Mock
2. HBV 11-12L.26
3. HBV 11-12L.188
4. HBV 11-12L.363
5. HBV 11-12L.367
6. HBV 11-12x.26

OPTIMIZED ENGINEERED MEGANUCLEASES HAVING SPECIFICITY FOR A RECOGNITION SEQUENCE IN THE HEPATITIS B VIRUS GENOME

RELATED APPLICATIONS

This application claims the benefit under 35 U.S.C. § 119(e) of U.S. provisional application No. 62/656,831, filed Apr. 12, 2018, which is incorporated by reference herein in its entirety.

FIELD OF THE INVENTION

The invention relates to the field of oncology, molecular biology and recombinant nucleic acid technology. In particular, the invention relates to optimized engineered meganucleases having specificity for a recognition sequence within the genome of genotypes A-G of the Hepatitis B virus. Such engineered meganucleases are useful in methods for treating Hepatitis B virus infections and hepatocellular carcinoma caused by Hepatitis B virus.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Apr. 11, 2019, is named P1090.70029US01-SEQ-MJT, and is 52 kilobytes in size.

BACKGROUND OF THE INVENTION

The Hepatitis B virus (HBV) is a major health problem worldwide and more than 350 million people are chronic carriers. HBV infection is a serious and common infectious disease of the liver. Chronic infection is associated with an increased risk to develop severe liver diseases, including liver cirrhosis and hepatocellular carcinoma (HCC), one of the most common forms of human cancer. The estimated risk of HCC in chronic HBV carriers is approximately 100 times greater than in uninfected individuals. About a third of the world population has been infected at one point in their lives, including 240 million to 350 million who have chronic infections. Over 750,000 people die of hepatitis B each year. About 300,000 of these are due to liver cancer. Currently available anti-HBV drugs have limitations. For example, interferon alpha administration is associated with severe adverse reactions. Nucleoside analogues are virostatic and require long-term administration.

The HBV genome exhibits genetic variability with an estimated rate of $1.4$-$3.2 \times 10^{-5}$ nucleotide substitutions per site per year. A large number of virus variants arise during replication as a result of nucleotide misincorporations in the absence of any proof reading capacity by the viral polymerase. This variability has resulted in well-recognized subtypes of the virus. HBV has been classified into well-defined genotypes on the basis of an inter-group divergence of 8% or more in the complete genomic sequence, each having a distinct geographical distribution. For example, Genotype A is widespread in sub-Saharan Africa, Northern Europe, and Western Africa; genotypes B and C are common in Asia; genotype C is primarily observed in Southeast Asia; genotype D is dominant in Africa, Europe, Mediterranean countries, and India; genotype G is reported in France, Germany, and the United States; and genotype H is commonly encountered in Central and South America. Genotype I has recently been reported in Vietnam and Laos. The newest HBV genotype, genotype J, has been identified in the Ryukyu Islands in Japan.

HBV is an enveloped DNA virus that belongs to the Hepadnaviridae family. It contains a small, partially double-stranded (DS), relaxed-circular DNA (rcDNA) genome that replicates by reverse transcription of an RNA intermediate, the pregenomic RNA (pgRNA). The circular DNA genome of HBV is unusual because the DNA is not fully double-stranded. One end of the full length strand is linked to the viral DNA polymerase. The genome is approximately 3020-3320 nucleotides long (for the full-length strand) and 1700-2800 nucleotides long (for the short length-strand). The negative-sense (non-coding) is complementary to the viral mRNA.

There are four known genes encoded by the genome, referred to as C, X, P, and S. The core protein is coded for by gene C (HBcAg), and its start codon is preceded by an upstream in-frame AUG start codon from which the pre-core protein is produced. The HBeAg is produced by proteolytic processing of the pre-core protein. The DNA polymerase is encoded by gene P. Gene S codes for the surface antigen (HBsAg). The HBsAg gene is one long open reading frame but contains three in frame "start" (ATG) codons that divide the gene into three sections: pre-S1, pre-S2, and S. Because of the multiple start codons, polypeptides of three different sizes called Large (the order from surface to the inside: pre-S1/pre-S2/S), Middle (pre-S2/S), and Small (S) are produced. The function of the protein coded for by gene X is not fully understood but it is associated with the development of liver cancer. It stimulates genes that promote cell growth and inactivates growth regulating molecules.

The viral DNA is found in the nucleus soon after infection of the cell. The partially double-stranded DNA is rendered fully double-stranded by completion of the (+) sense strand and removal of a protein molecule from the (−) sense strand and a short sequence of RNA from the (+) sense strand. Non-coding bases are removed from the ends of the (−) sense strand and the ends are rejoined.

The HBV life cycle begins when the virus attaches to the host cell and is internalized. Recent studies have demonstrated that sodium-taurocholate co-transporting polypeptide (NTCP) is a functional receptor in HBV infection. The virion relaxed circular DNA (rcDNA) is delivered to the nucleus, where it is repaired to form a covalently closed-circular DNA (cccDNA). The episomal cccDNA serves as the template for the transcription of the pregenomic RNA (pgRNA) and the other viral mRNAs by the host RNA polymerase II. The transcripts are then exported to the cytoplasm, where translation of the viral proteins occurs. Reverse transcriptase (RT) binds to pgRNA and triggers assembly of the core proteins into immature, RNA-containing nucleocapsids. The immature nucleocapsids then undergo a process of maturation whereby pgRNA is reversed transcribed by RT to make the mature rcDNA. A unique feature of hepadnavirus reverse transcription is the RT primed initiation of minus-strand DNA synthesis, which leads to the covalent linkage of RT to the 5' end of the minus-strand DNA.

The mature, rcDNA-containing nucleocapsids are then enveloped by the viral surface proteins and secreted as virions (secretion pathway) or, alternatively, are recycled back to the nucleus to further amplify the pool of cccDNA (recycling pathway). Persistence of cccDNA in hepatocytes plays a key role in viral persistence, reactivation of viral replication after cessation of antiviral therapy, and resistance to therapy.

Homing endonucleases are a group of naturally-occurring nucleases which recognize 15-40 base-pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), Q. Rev. Biophys. 38: 49-95). Homing endonucleases are commonly grouped into four families: the LAGLIDADG (SEQ ID NO: 2) family, the GIY-YIG family, the His-Cys box family and the HNH family. These families are characterized by structural motifs, which affect catalytic activity and recognition sequence. For instance, members of the LAGLIDADG (SEQ ID NO: 2) family are characterized by having either one or two copies of the conserved LAGLIDADG (SEQ ID NO: 2) motif (see Chevalier et al. (2001), Nucleic Acids Res. 29(18): 3757-3774). The LAGLIDADG (SEQ ID NO: 2) homing endonucleases with a single copy of the LAGLIDADG (SEQ ID NO: 2) motif form homodimers, whereas members with two copies of the LAGLIDADG (SEQ ID NO: 2) motif are found as monomers. Methods for producing homing endonucleases are known in the art.

I-CreI (SEQ ID NO: 1) is a member of the LAGLIDADG (SEQ ID NO: 2) family of homing endonucleases which recognizes and cuts a 22 basepair recognition sequence in the chloroplast chromosome of the algae *Chlamydomonas reinhardtii*. Genetic selection techniques have been used to modify the wild-type I-CreI cleavage site preference (Sussman et al. (2004), J. Mol. Biol. 342: 31-41; Chames et al. (2005), Nucleic Acids Res. 33: e178; Seligman et al. (2002), Nucleic Acids Res. 30: 3870-9, Arnould et al. (2006), J. Mol. Biol. 355: 443-58). Methods for rationally-designing mono-LAGLIDADG (SEQ ID NO: 2) homing endonucleases were described which are capable of comprehensively redesigning I-CreI and other homing endonucleases to target widely-divergent DNA sites, including sites in mammalian, yeast, plant, bacterial, and viral genomes (see, e.g., WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (see also Li et al. (2009), Nucleic Acids Res. 37:1650-62; Grizot et al. (2009), Nucleic Acids Res. 37:5405-19). Thus, a functional "single-chain" meganuclease can be expressed from a single transcript.

The use of engineered meganucleases for treatment of HBV infections has been suggested. For example, WO 2010/136841 suggests the use of engineered meganucleases for cleaving the genome of non-genomically integrating viruses. Such meganucleases include variants of I-CreI targeting 22 base pair meganuclease recognition sequences which differ from those disclosed herein, and which are only present in a few HBV genotypes.

Applicants previously disclosed in PCT/US2017/56638 a number of first-generation engineered meganucleases having specificity for recognition sequences present in the HBV genome, including the HBV 11-12 recognition sequence (SEQ ID NO: 10) which is advantageously present in the genome of at least HBV genotypes A-G (SEQ ID NOs: 3-9).

The present invention improves upon the engineered meganucleases previously described in the art in a number of aspects. When generating an endonuclease for therapeutic administration to a patient, it is critical that on-target specificity is enhanced (i.e., increased) while reducing or eliminating off-target cutting within the target cell genome. Here, Applicants have developed second-generation engineered meganucleases which target the HBV 11-12 recognition sequence. The meganucleases of the present invention have novel and unique sequences which were generated through extensive experimentation. Additionally, these second-generation meganucleases have a number of improved and unexpected properties when compared to the previously disclosed first-generation nucleases, including a significant reduction in off-target cutting in the host cell genome and enhanced (i.e., increased) formation of indels (i.e., insertions or deletions within the HBV genome at the cleavage site, indicative of on-target cutting) in cell lines comprising an integrated copy of the HBV genome. Thus, the meganucleases of the invention advance the art in a number of ways that are necessary for development of a clinical product targeting HBV infection and HBV-related hepatocellular carcinoma.

SUMMARY OF THE INVENTION

The present invention provides second-generation engineered meganucleases that recognize and cleave a recognition sequence conserved across multiple genotypes of Hepatitis B viruses. Cleavage at the recognition sequence by an engineered meganuclease disclosed herein can disrupt expression of one or more viral proteins due to non-homologous end joining (NHEJ) at the cleavage site. NHEJ can result in insertions, deletions, or result in a frameshift mutation that can interfere with gene expression. Alternatively, a "suicide gene" can be introduced into a Hepatitis B virus (HBV) genome via homologous recombination. In another embodiment, the HBV genome or cccDNA may be degraded following cleavage at the HBV 11-12 recognition sequence. Accordingly, by interrupting normal gene expression, the infection and proliferation of HBV can be reduced or eliminated according to the methods disclosed herein. Such meganucleases are, therefore, useful for treating or reducing the proliferation of HBV in infected individuals worldwide.

Suppression or eradication of the replication of HBV in the liver leads to improved liver pathology and decreased progression to liver cirrhosis and hepatocellular carcinoma (HCC). Thus, the present invention also provides pharmaceutical compositions and methods for treatment of a subject having HBV or HCC which utilize an engineered meganuclease having specificity for a recognition sequence comprising SEQ ID NO: 10 within a Hepatitis B virus genome. The present invention further provides methods of delivering the engineered meganucleases disclosed herein, or a nucleic acid encoding the same, to a subject infected with HBV in order to reduce the level of HBV virus or HBV cccDNA and/or reduce the symptoms associated with an HBV infection.

In some embodiments, the presently disclosed engineered meganucleases exhibit at least one optimized characteristic in comparison to the first-generation meganuclease HBV 11-12x.26. Such optimized characteristics include improved (i.e., increased) specificity resulting in reduced off-target cutting, and enhanced (i.e., increased) efficiency of cleavage and indel formation at the HBV 11-12 recognition sequence, for example in cells comprising an integrated copy of the HBV genome.

Thus, in one aspect, the invention provides an engineered meganuclease that recognizes and cleaves the HBV 11-12 recognition sequence (SEQ ID NO: 10) within a Hepatitis B virus genome. The engineered meganuclease comprises a first subunit and a second subunit, wherein the first subunit binds to a first recognition half-site of the recognition sequence and comprises a first hypervariable (HVR1) region, wherein the second subunit binds to a second recognition half site of the recognition sequence and comprises a second hypervariable (HVR2) region, and wherein said HVR1 has at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to an amino acid sequence corresponding to residues 215-270 of the presently disclosed HBV 11-12L.363 meganuclease (the amino acid sequence of which is set forth as SEQ ID NO: 12) or the presently disclosed HBV 11-12L.367 meganuclease (the amino acid sequence of which is set forth as SEQ ID NO: 13).

In certain embodiments, the HVR1 region comprises an amino acid sequence corresponding to residues 215-270 of SEQ ID NOs: 12 or 13 with up to 1, 2, 3, 4, 5, 6, or 7 amino acid substitutions.

In some embodiments, the HVR1 region comprises residues corresponding to residues 223, 233, 239, 241, 259, 263, 264, and 268 of SEQ ID NO: 12. In some embodiments, the HVR1 region comprises residues corresponding to residues 223, 233, 241, 259, 262, 263, 264, and 268 of SEQ ID NO: 13.

In some embodiments, the HVR1 region comprises residues corresponding to residues 215, 217, 219, 221, 223, 224, 229, 231, 233, 235, 237, 259, 261, 266, and 268 of SEQ ID NO: 12 or 13.

In some embodiments, the HVR1 region comprises residues corresponding to residues 239, 241, 263, and 264 of SEQ ID NO: 12.

In some embodiments, the HVR1 region comprises residues corresponding to residues 241, 262, 263, and 264 of SEQ ID NO: 13.

In some embodiments, the HVR1 region comprises residues corresponding to residues 215, 217, 219, 221, 223, 224, 229, 231, 233, 235, 237, 239, 241, 259, 261, 262, 263, 264, 266, and 268 of SEQ ID NO: 12 or 13.

In certain embodiments, the HVR1 region comprises Y, R, K, or D at a residue corresponding to residue 257 of SEQ ID NO: 12 or 13.

In certain embodiments, the HVR1 region comprises residues 215-270 of SEQ ID NO: 12 or 13.

In particular embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 198-344 of SEQ ID NO: 12 or 13. In certain embodiments, the first subunit comprises an amino acid sequence having at least 94% sequence identity to residues 198-344 of SEQ ID NO: 12 or 13. In some embodiments, the first subunit comprises an amino acid sequence corresponding to residues 198-344 of SEQ ID NOs: 12 or 13 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions.

In certain embodiments, the first subunit comprises G, S, or A at a residue corresponding to residue 210 of SEQ ID NO: 12 or 13.

In certain embodiments, the first subunit comprises E, Q, or K at a residue corresponding to residue 271 of SEQ ID NO: 12 or 13.

In certain embodiments, the first subunit comprises a residue corresponding to residue 271 of SEQ ID NO: 12 or 13.

In particular embodiments, the first subunit comprises residues 198-344 of SEQ ID NO: 12 or 13.

In some such embodiments, the HVR2 region comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 24-79 of SEQ ID NO: 12 or 13. In certain embodiments, the HVR2 region comprises an amino acid sequence corresponding to residues 24-79 of SEQ ID NOs: 12 or 13 with up to 1, 2, 3, 4, 5, 6, 7, 8, 9, 10, or 11 amino acid substitutions.

In certain embodiments, the HVR2 region comprises residues corresponding to residues 26 and 77 of SEQ ID NO: 12 or 13.

In certain embodiments, the HVR2 region comprises residues corresponding to residues 24, 26, 28, 30, 32, 33, 38, 40, 42, 44, 46, 68, 70, 75, and 77 of SEQ ID NO: 12 or 13.

In certain embodiments, the HVR2 region comprises Y, R, K, or D at a residue corresponding to residue 66 of SEQ ID NO: 12 or 13.

In particular embodiments, the HVR2 region comprises residues 24-79 of SEQ ID NO: 12 or 13.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 7-153 of SEQ ID NO: 12 or 13. In certain embodiments, the second subunit comprises an amino acid sequence having at least 99% sequence identity to an amino acid sequence corresponding to residues 7-153 of SEQ ID NO: 12 or 13. In particular embodiments, the second subunit comprises an amino acid sequence corresponding to residues 7-153 of SEQ ID NOs: 12 or 13 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions.

In certain embodiments, the second subunit comprises G, S, or A at a residue corresponding to residue 19 of SEQ ID NO: 12 or 13.

In certain embodiments, the second subunit comprises E, Q, or K at a residue corresponding to residue 80 of SEQ ID NO: 12 or 13.

In certain embodiments, the second subunit comprises a residue corresponding to residue 80 of SEQ ID NO: 12 or 13.

In particular embodiments, the second subunit comprises residues 7-153 of SEQ ID NO: 12 or 13.

In some embodiments, the first subunit of the engineered meganuclease has at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 198-344 of SEQ ID NO: 12 or 13, and the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 7-153 of SEQ ID NO: 12 or 13. In particular embodiments, the first subunit of the engineered meganuclease has at least 94% sequence identity to an amino acid sequence corresponding to residues 198-344 of SEQ ID NO: 12 or 13, and the second subunit comprises an amino acid sequence having at least 99% sequence identity to an amino acid sequence corresponding to residues 7-153 of SEQ ID NO: 12 or 13. In certain embodiments, the first subunit and/or the second subunit can comprise up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions relative to residues 198-344 and residues 7-153, respectively, of SEQ ID NOs: 12 and 13.

In certain embodiments, the engineered meganuclease comprises a linker, wherein the linker covalently joins the first subunit and the second subunit.

In some embodiments, the engineered meganuclease comprises an amino acid sequence having at least about 90%, about 91%, about 92%, about 93%, about 94%, about 95%, about 96%, about 97%, about 98%, or about 99% sequence identity to the amino acid sequence of SEQ ID NO: 12 or 13. In certain embodiments, the engineered meganuclease comprises an amino acid sequence having at least 97% sequence identity to the amino acid sequence of SEQ ID NO: 12.

In particular embodiments, the engineered meganuclease comprises the amino acid sequence of SEQ ID NO: 12 or 13.

In another aspect, the invention provides a polynucleotide comprising a nucleic acid sequence encoding an engineered meganuclease described herein.

In certain embodiments, the polynucleotide is an mRNA.

In further embodiments, the mRNA is a polycistronic mRNA encoding one or more engineered meganucleases described herein. In certain embodiments, the polycistronic mRNA encodes at least one of the presently disclosed engineered meganucleases which recognizes and cleaves a recognition sequence comprising SEQ ID NO: 10, and a second engineered meganuclease which recognizes and cleaves a second recognition sequence which is present in a Hepatitis B virus genome but differs from SEQ ID NO: 10. In some of these embodiments, the second recognition sequence comprises the HBV 5-6 recognition sequence (which is set forth as SEQ ID NO: 21).

In further embodiments, a polycistronic mRNA of the invention can encode one or more engineered meganucleases described herein and one or more additional proteins that induce a therapeutically beneficial effect in an HBV-infected cell and/or HBV-infected subject.

In another aspect, the invention provides a recombinant DNA construct comprising a polynucleotide described herein. In some embodiments, the recombinant DNA construct comprises a cassette comprising a promoter and a nucleic acid sequence encoding an engineered meganuclease described herein. In other embodiments, the recombinant DNA construct comprises at least a first cassette and a second cassette, wherein the first cassette comprises a promoter and a nucleic acid sequence encoding an engineered meganuclease described herein, and wherein the second cassette comprises a promoter and a nucleic acid sequence encoding a second engineered meganuclease which recognizes and cleaves a second recognition sequence which is present in a Hepatitis B virus genome but differs from SEQ ID NO: 10. In some of these embodiments, the second recognition sequence comprises SEQ ID NO: 21.

In other embodiments, the recombinant DNA construct comprises a cassette comprising a promoter and a polycistronic nucleic acid sequence, wherein the promoter drives expression of the polycistronic nucleic acid sequence to generate a polycistronic mRNA described herein in a target cell.

In certain embodiments, the recombinant DNA construct encodes a viral vector comprising a nucleic acid sequence encoding an engineered meganuclease disclosed herein. In particular embodiments, the viral vector is a recombinant AAV vector.

In another aspect, the invention provides a viral vector comprising a nucleic acid sequence encoding an engineered meganuclease described herein. In particular embodiments, the viral vector is a recombinant AAV vector.

In some embodiments, the viral vector comprises a cassette comprising a promoter and a nucleic acid sequence encoding an engineered meganuclease described herein. In other embodiments, the viral vector comprises at least a first cassette and a second cassette, wherein the first cassette comprises a promoter and a nucleic acid sequence encoding an engineered meganuclease described herein, and wherein the second cassette comprises a promoter and a nucleic acid sequence encoding a second engineered meganuclease which recognizes and cleaves a second recognition sequence which is present in a Hepatitis B virus genome but differs from SEQ ID NO: 10. In some of these embodiments, the second recognition sequence comprises SEQ ID NO: 21.

In other embodiments, the viral vector comprises one cassette comprising a promoter and a polycistronic nucleic acid sequence, wherein the promoter drives expression of the polycistronic nucleic acid sequence to generate a polycistronic mRNA described herein in a target cell.

In another aspect, the invention provides a pharmaceutical composition for treatment of a subject having Hepatitis B virus or hepatocellular carcinoma caused by Hepatitis B virus, the pharmaceutical composition comprising a pharmaceutically acceptable carrier and: (a) a nucleic acid encoding an engineered meganuclease described herein; or (b) an engineered meganuclease described herein.

In one embodiment, the nucleic acid sequence of the pharmaceutical composition encoding an engineered meganuclease disclosed herein is an mRNA described herein. In some such embodiments, the mRNA can be a polycistronic mRNA described herein, such that an engineered meganuclease described herein is expressed in the target cell in vivo, along with a second engineered meganuclease which recognizes and cleaves a second recognition sequence which is present in a Hepatitis B virus genome but differs from SEQ ID NO: 10. In some of these embodiments, the second recognition sequence comprises SEQ ID NO: 21.

In another embodiment, the pharmaceutical composition comprises a recombinant DNA construct described herein comprising the nucleic acid sequence encoding an engineered meganuclease disclosed herein. In some such embodiments, the recombinant DNA construct comprises a cassette comprising a promoter and a nucleic acid sequence encoding an engineered meganuclease of the invention. In other embodiments, the recombinant DNA construct of the pharmaceutical composition comprises at least a first cassette and a second cassette, wherein the first cassette comprises a promoter and a nucleic acid sequence encoding an engineered meganuclease described herein, and wherein the second cassette comprises a promoter and a nucleic acid sequence encoding a second engineered meganuclease which recognizes and cleaves a second recognition sequence which is present in a Hepatitis B virus genome but differs from SEQ ID NO: 10. In some of these embodiments, the second recognition sequence comprises SEQ ID NO: 21.

In other embodiments, the recombinant DNA construct of the pharmaceutical composition comprises a cassette comprising a promoter and a polycistronic nucleic acid sequence, wherein the promoter drives expression of the polycistronic nucleic acid sequence to generate a polycistronic mRNA described herein in the target cell in vivo.

In another embodiment, the pharmaceutical composition comprises a viral vector comprising the nucleic acid sequence encoding an engineered meganuclease disclosed herein. In one such embodiment, the viral vector can be a retrovirus, a lentivirus, an adenovirus, or an AAV. In a particular embodiment, the viral vector can be a recombinant AAV vector.

In some such embodiments, the viral vector comprises a cassette comprising a promoter and a nucleic acid sequence encoding an engineered meganuclease described herein. In other embodiments, the viral vector comprises at least a first cassette and a second cassette, wherein the first cassette comprises a promoter and a nucleic acid sequence encoding an engineered meganuclease described herein, and wherein the second cassette comprises a promoter and a nucleic acid sequence encoding a second engineered meganuclease which recognizes and cleaves a second recognition sequence which is present in a Hepatitis B virus genome but differs from SEQ ID NO: 10. In some of these embodiments, the second recognition sequence comprises SEQ ID NO: 21.

In other such embodiments, the viral vector comprises one cassette comprising a promoter and a polycistronic nucleic acid sequence, wherein the promoter drives expression of the polycistronic nucleic acid sequence to generate a polycistronic mRNA described herein in the target cell in vivo.

In other embodiments, the pharmaceutical composition comprises an engineered meganuclease described herein. In various embodiments, the pharmaceutical composition comprises an engineered meganuclease described herein and a second engineered meganuclease which recognizes and cleaves a second recognition sequence which is present in a Hepatitis B virus genome but differs from SEQ ID NO: 10. In some of these embodiments, the second recognition sequence comprises SEQ ID NO: 21.

In still other embodiments, the pharmaceutical composition comprises a nucleic acid encoding an engineered meganuclease described herein and a nucleic acid encoding a second engineered meganuclease which recognizes and cleaves a second recognition sequence which is present in a Hepatitis B virus genome but differs from SEQ ID NO: 10. In some of these embodiments, the second recognition sequence comprises SEQ ID NO: 21. In such embodiments, the two nucleic acids may be comprised by mRNAs described herein, recombinant DNA constructs described herein, and/or viral vectors described herein.

In some embodiments, the pharmaceutical composition can comprise one or more mRNAs described herein encapsulated within lipid nanoparticles. In particular embodiments, the lipid nanoparticles of the pharmaceutical composition can comprise at least a first mRNA and at least a second mRNA, wherein the first mRNA encodes an engineered meganuclease described herein, and the second mRNA encodes a second engineered meganuclease which recognizes and cleaves a second recognition sequence which is present in a Hepatitis B virus genome but differs from SEQ ID NO: 10. In some of these embodiments, the second recognition sequence comprises SEQ ID NO: 21. In other embodiments, the lipid nanoparticles of the pharmaceutical composition can comprise one or more polycistronic mRNAs described herein, wherein the polycistronic mRNA encodes an engineered meganuclease described herein and a second engineered meganuclease which recognizes and cleaves a second recognition sequence which is present in a Hepatitis B virus genome but differs from SEQ ID NO: 10. In some of these embodiments, the second recognition sequence comprises SEQ ID NO: 21. In some embodiments, the lipid nanoparticles have a composition which enhances delivery and uptake in the liver, and specifically within hepatocytes.

In another aspect, the invention provides a lipid nanoparticle, or a lipid nanoparticle formulation, comprising mRNA encoding at least one engineered meganuclease described herein.

In particular embodiments, the lipid nanoparticles can comprise at least a first mRNA and at least a second mRNA, wherein the first mRNA encodes an engineered meganuclease described herein, and the second mRNA encodes a second engineered meganuclease which recognizes and cleaves a second recognition sequence which is present in a Hepatitis B virus genome but differs from SEQ ID NO: 10. In some of these embodiments, the second recognition sequence comprises SEQ ID NO: 21.

In other embodiments, the lipid nanoparticles of the pharmaceutical composition can comprise one or more polycistronic mRNAs described herein, wherein the polycistronic mRNA encodes an engineered meganuclease described herein and a second engineered meganuclease which recognizes and cleaves a second recognition sequence which is present in a Hepatitis B virus genome but differs from SEQ ID NO: 10. In some of these embodiments, the second recognition sequence comprises SEQ ID NO: 21.

In some embodiments, the lipid nanoparticles have a composition which enhances delivery and uptake in the liver, and specifically within hepatocytes.

In another aspect, the invention provides a method for treating a subject having HBV or hepatocellular carcinoma caused by HBV. Likewise, provided herein is a method for reducing the level and/or proliferation of HBV, or reducing the symptoms associated with HBV. The methods comprise delivering to a target cell in the subject: (a) a therapeutically effective amount of a nucleic acid encoding an engineered meganuclease described herein, wherein the engineered meganuclease is expressed in the target cell in vivo; or (b) a therapeutically effective amount of an engineered meganuclease protein described herein; wherein the engineered meganuclease recognizes and cleaves a recognition sequence comprising SEQ ID NO: 10 within the HBV genome in the target cell. The method can reduce or eliminate the infection and/or proliferation of HBV in the subject.

In certain embodiments, the methods reduce circulating HBsAg levels, circulating HBeAg levels, circulating HBV DNA levels, and/or hepatic cccDNA levels.

In another aspect, the invention provides a method for treating a subject having HCC caused by HBV. The methods comprise delivering to a target cell in the subject: (1) (a) a nucleic acid encoding an engineered meganuclease described herein, wherein the engineered meganuclease is expressed in the target cell in vivo; or (b) an engineered meganuclease protein; and (2) a nucleic acid comprising a polynucleotide sequence encoding a suicide gene and sequences homologous to sequences flanking the meganuclease cleavage site; wherein the engineered meganuclease recognizes and cleaves a recognition sequence comprising SEQ ID NO: 10 within the Hepatitis B virus genome, thus cleaving the HBV genome in the target cell; wherein the suicide gene is inserted into the cleaved HBV genome by homologous recombination; and wherein expression of the suicide gene kills the target cell.

In some embodiments, the suicide gene is directly lethal to the target cell. In some such embodiments, the directly lethal suicide gene encodes a toxic polypeptide or a pro-apoptotic protein. In some embodiments, the suicide gene is indirectly lethal to the target cell, and directs the subject's own immune system to kill the target cell. In some such embodiments, the indirectly lethal suicide gene encodes a cell surface protein which is recognized as foreign by the subject's immune system and is targeted by a humoral or cellular immune response. In other such embodiments, the indirectly lethal suicide gene encodes a polypeptide which is presented by an MHC Class I molecule, is recognized as foreign by the subject's immune system, and is targeted by a cytotoxic immune response.

In further embodiments, the methods of treatment for HBV infection or HCC comprise administering to the subject any pharmaceutical composition of the invention described herein which comprises, at least, a pharmaceutically acceptable carrier and (a) a nucleic acid encoding an engineered meganuclease described herein, wherein the engineered meganuclease is expressed in a target cell in vivo; or (b) an engineered meganuclease protein described herein.

In some embodiments of the methods of treatment for HBV infection or HCC, the engineered meganuclease, or the nucleic acid encoding the engineered meganuclease, can be delivered to a target hepatocyte cell. In particular embodiments, an effective amount of the engineered meganuclease, or the nucleic acid encoding the engineered meganuclease, can be delivered to a target hepatocyte cell.

In certain embodiments, the methods reduce circulating HBsAg levels, circulating HBeAg levels, circulating HBV DNA levels, and/or hepatic cccDNA levels.

In particular embodiments, delivery to a hepatocyte cell occurs ex vivo, wherein an effective amount of the hepatocyte cells having been delivered the engineered meganuclease, or the nucleic acid encoding the engineered meganuclease, are administered to a subject.

In some embodiments, a hepatotoxic protein, or a nucleic acid or AAV encoding a hepatotoxic protein, is administered with the pharmaceutical compositions disclosed herein.

In particular embodiments of the methods, the engineered meganuclease comprises the amino acid sequence of SEQ ID NO: 12 or 13.

In particular embodiments of the methods, the subject can be a mammal, such as a human.

In another aspect, the invention provides an engineered meganuclease described herein for use as a medicament. The invention further provides the use of an engineered meganuclease, described herein in the manufacture of a medicament for treating HBV, for reducing the level or proliferation of HBV, reducing the symptoms associated with HBV, or treating HCC.

In another aspect, the invention provides an isolated polynucleotide for use as a medicament, wherein the isolated polynucleotide comprises a nucleic acid sequence encoding an engineered meganuclease disclosed herein. The invention further provides the use of an isolated polynucleotide in the manufacture of a medicament for treating HBV, for reducing the level or proliferation of HBV, reducing the symptoms associated with HBV, or treating HCC.

In another aspect, the invention provides a recombinant AAV vector for use as a medicament, wherein the recombinant AAV vector comprises a polynucleotide, and wherein the polynucleotide comprises a nucleic acid sequence encoding an engineered meganuclease disclosed herein. The invention further provides the use of a recombinant AAV vector in the manufacture of a medicament for treating HBV, for reducing the level or proliferation of HBV, reducing the symptoms associated with HBV, or treating HCC, wherein the recombinant AAV vector comprises a polynucleotide, and wherein the polynucleotide comprises a nucleic acid sequence encoding an engineered meganuclease disclosed herein.

BRIEF DESCRIPTION OF THE FIGURES

FIG. 2. HBV 11-12 recognition sequence in the HBV genome. The HBV 11-12 recognition sequence, targeted by engineered meganucleases of the invention, comprises two recognition half-sites. Each recognition half-site comprises 9 base pairs, separated by a 4 base pair central sequence. The HBV 11-12 recognition sequence (SEQ ID NO: 10) comprises two recognition half-sites referred to as HBV11 and HBV12.

FIG. 3. Alignment of HBV recognition sequences in HBV genotypes A-G. The HBV 11-12 recognition sequence targeted by engineered meganucleases of the invention is conserved across multiple HBV genotypes. The HBV 11-12 recognition sequence spans residues 1259-1280 of HBV genotype A set forth in SEQ ID NO: 3, and this recognition sequence is fully conserved in genotypes B, C, D, E, F, and G (SEQ ID NOs: 4-9).

BRIEF DESCRIPTION OF THE SEQUENCES

Figure 1:
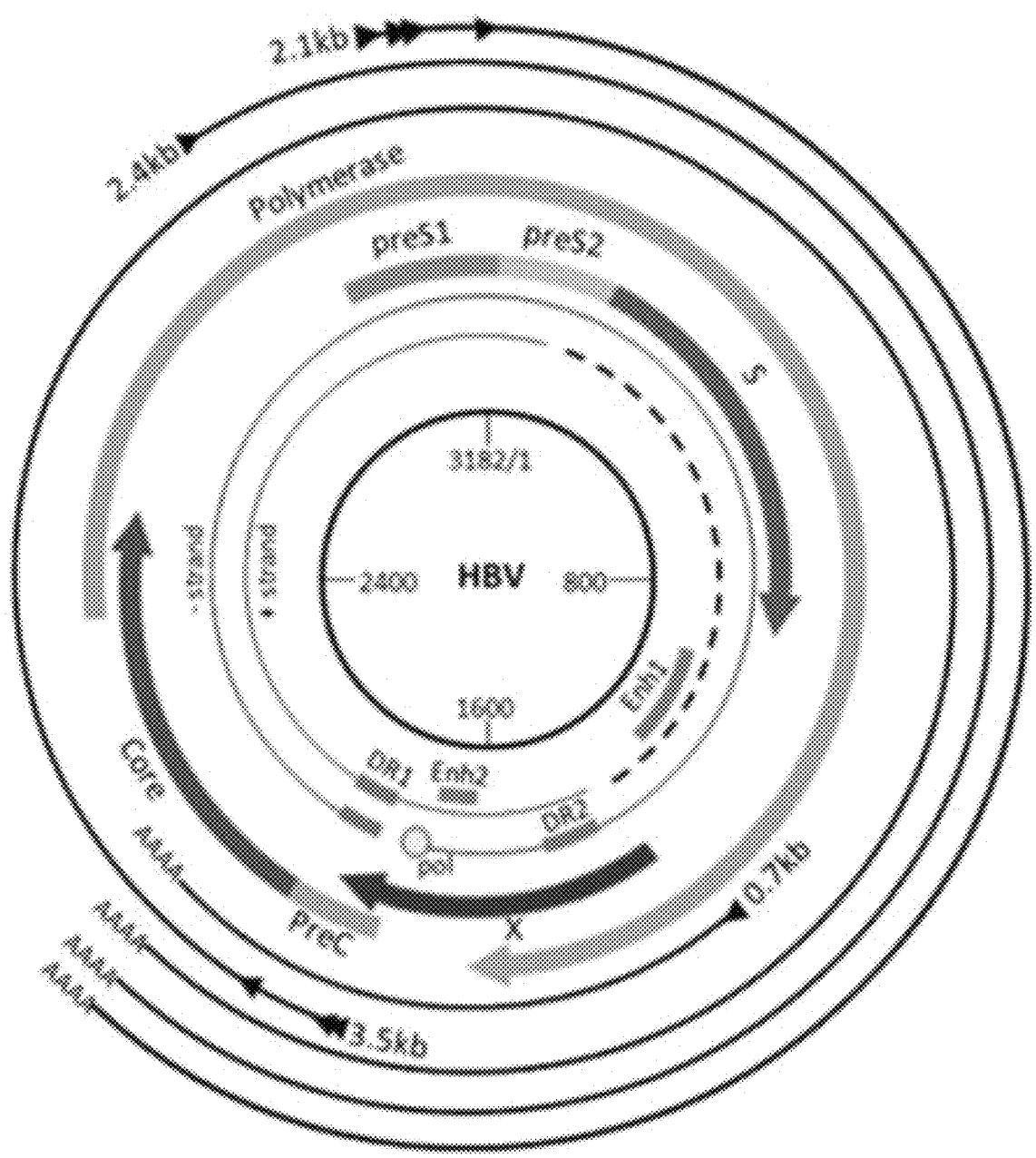
FIG. 1 shows a genomic map of the HBV genome and identifies all ORFs. Virus particles have a partially double-stranded genome (indicated by a dashed line) with a cohesive overlap that spans the 5' regions of each strand and that is flanked by direct repeat sequences (DR1 and DR2). The gene S encodes the major hepatitis B surface antigen (HBsAg) protein and its glycosylated partner, which are transmembrane proteins in the virus envelope. In-frame sequences upstream from the S gene encode the pre-S domains, which are translated with the S sequences to make the pre-S and S polypeptides (middle and large proteins) that contain the virus receptor for infection of hepatocytes. Gene C encodes the hepatitis B core antigen (HBcAg) which forms the nucleocapsid of the virus. The P region encodes the virus reverse transcriptase that also has DNA-dependent DNA polymerase activity and RNase H activity required for virus replication. Although HBV is a DNA virus, it replicates through a pre-genomic RNA intermediate. Finally, the X gene encodes the small regulatory protein of the virus, the hepatitis Bx(HBx) antigen. HBx is a transactivating protein that stimulates virus gene expression and replication, protects virus-infected cells against immune-mediated destruction and contributes to the development of hepatocellular carcinoma.
Figure 4:
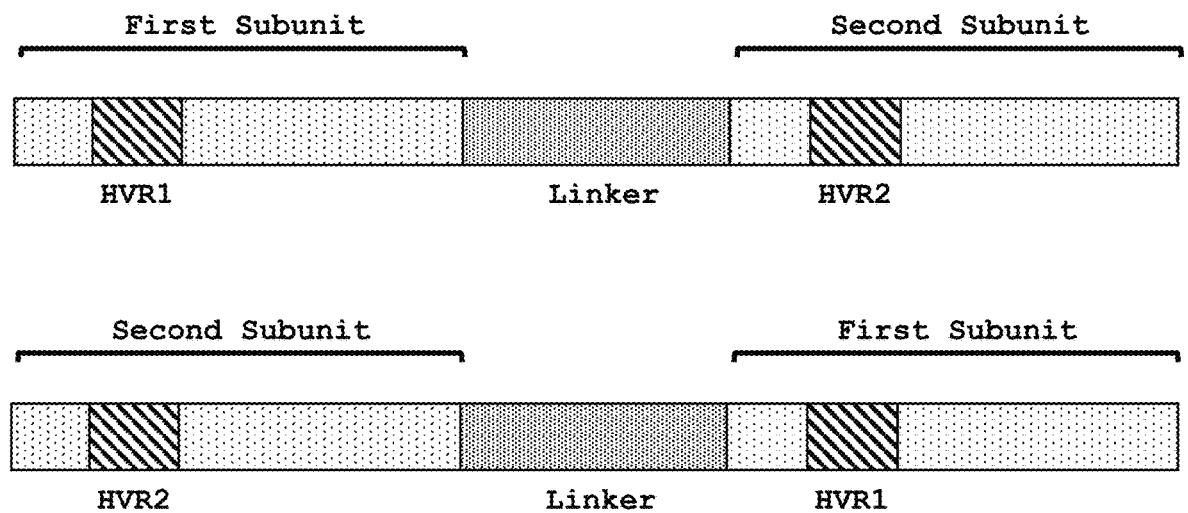
FIG. 4. The engineered meganucleases of the invention comprise two subunits, wherein the first subunit comprising the HVR1 region binds to a first recognition half-site (e.g., HBV11) and the second subunit comprising the HVR2 region binds to a second recognition half-site (e.g., HBV12). In embodiments where the engineered meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.

SEQ ID NO: 1 sets forth the amino acid sequence of the wild-type I-CreI meganuclease from *Chlamydomonas reinhardtii*.

SEQ ID NO: 2 sets forth the amino acid sequence of the LAGLIDADG motif.

SEQ ID NO: 3 sets forth the nucleic acid sequence of HBV genotype A.

SEQ ID NO: 4 sets forth the nucleic acid sequence of HBV genotype B.

SEQ ID NO: 5 sets forth the nucleic acid sequence of HBV genotype C.

SEQ ID NO: 6 sets forth the nucleic acid sequence of HBV genotype D.

SEQ ID NO: 7 sets forth the nucleic acid sequence of HBV genotype E.

SEQ ID NO: 8 sets forth the nucleic acid sequence of HBV genotype F.

SEQ ID NO: 9 sets forth the nucleic acid sequence of HBV genotype G.

SEQ ID NO: 10 sets forth the nucleic acid sequence of the sense strand of the HBV 11-12 recognition sequence.

SEQ ID NO: 11 sets forth the nucleic acid sequence of the antisense strand of the HBV 11-12 recognition sequence.

SEQ ID NO: 12 sets forth the amino acid sequence of the HBV 11-12L.363 meganuclease.

SEQ ID NO: 13 sets forth the amino acid sequence of the HBV 11-12L.367 meganuclease.

SEQ ID NO: 14 sets forth the amino acid sequence of the HBV 11-12x.26 meganuclease.

SEQ ID NO: 15 sets forth the amino acid sequence of the HBV 11-12L.363 meganuclease HBV11-binding subunit.

SEQ ID NO: 16 sets forth the amino acid sequence of the HBV 11-12L.367 meganuclease HBV11-binding subunit.

SEQ ID NO: 17 sets forth the amino acid sequence of the HBV 11-12x.26 meganuclease HBV11-binding subunit.

SEQ ID NO: 18 sets forth the amino acid sequence of the HBV 11-12L.363 meganuclease HBV12-binding subunit.

SEQ ID NO: 19 sets forth the amino acid sequence of the HBV 11-12L.367 meganuclease HBV12-binding subunit.

SEQ ID NO: 20 sets forth the amino acid sequence of the HBV 11-12x.26 meganuclease HBV12-binding subunit.

SEQ ID NO: 21 sets forth the nucleic acid sequence of the HBV 5-6 recognition sequence (sense).

SEQ ID NO: 22 sets forth the nucleic acid sequence of the HBV 5-6 recognition sequence (antisense).

SEQ ID NO: 23 sets forth the nucleic acid sequence of the HBV11 Off recognition sequence.

SEQ ID NO: 24 sets forth the nucleic acid sequence of the HBV12 Off recognition sequence.

SEQ ID NO: 25 sets forth the nucleic acid sequence of the P1 PCR primer.

SEQ ID NO: 26 sets forth the nucleic acid sequence of the P2 PCR primer.

SEQ ID NO: 27 sets forth the nucleic acid sequence of the P3 PCR primer.

SEQ ID NO: 28 sets forth the nucleic acid sequence of the P4 PCR primer.

SEQ ID NO: 29 sets forth the nucleic acid sequence of the T1 PCR primer.

SEQ ID NO: 30 sets forth the nucleic acid sequence of the T2 PCR primer.

SEQ ID NO: 31 sets forth the nucleic acid sequence of the AD38-F1012 primer.

SEQ ID NO: 32 sets forth the nucleic acid sequence of the AD38-R1479 primer.

SEQ ID NO: 33 sets froth the amino acid sequence of a polypeptide linker.

DETAILED DESCRIPTION OF THE INVENTION 1.1 References and Definitions

The patent and scientific literature referred to herein establishes knowledge that is available to those of skill in the art. The issued US and non-US patents, allowed applications, published US, non-US, and PCT application, co-owned and co-pending unpublished US patent applications, published foreign applications, and scientific, technical, and medical references, including GenBank database sequences, public genetic and protein database accession numbers or codes (and the nucleic acid and/or amino acid sequences associated therewith), which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood as of the priority date by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the terms "nuclease" and "endonuclease" refers to enzymes which cleave a phosphodiester bond within a polynucleotide chain.

As used herein with respect to double-stranded DNA, the terms "cleave" or "cleavage" refer to the endonuclease-mediated hydrolysis of phosphodiester bonds within the backbone of a recognition sequence within a target sequence that results in a double-stranded break within the target sequence, referred to herein as a "cleavage site". Depending upon the endonuclease, cleavage can result in double-stranded fragments with blunt ends or fragments with 5' or 3' base overhangs.

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI, and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g. WO 2007/047859, incorporated by reference in its entirety). A meganuclease as used herein binds to double-stranded DNA as a heterodimer. A meganuclease may also be a "single-chain meganuclease" in which a pair of DNA-binding domains is joined into a single polypeptide using a peptide linker. The term "homing endonuclease" is synonymous with the term "meganuclease." Meganucleases of the present disclosure are substantially non-toxic when expressed in the targeted cells as described herein such that cells can be transfected and maintained at 37° C. without observing substantial deleterious effects on overall cell viability or significant reductions in meganuclease cleavage activity when measured using the methods described herein.

As used herein, the term "single-chain meganuclease" refers to a polypeptide comprising a pair of nuclease subunits joined by a linker such that the subunits interact functionally like a heterodimer to cleave a double-stranded recognition site. A single-chain meganuclease has the organization: N-terminal subunit—Linker—C-terminal subunit. The two meganuclease subunits will generally be non-identical in amino acid sequence and will recognize non-identical DNA half-sites within a recognition sequence. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two meganuclease subunits into a single polypeptide. A linker may have a sequence that is found in natural proteins, or may be an artificial sequence that is not found in any natural protein. A linker may be flexible and lacking in secondary structure or may have a propensity to form a specific three-dimensional structure under physiological conditions. A linker can include, without limitation, any of those encompassed by U.S. Pat. Nos. 8,445,251, 9,340,777, 9,434,931, and 10,041,053, each of which is incorporated by reference in its entirety. In some embodiments, a linker may have at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 33, which sets forth residues 154-195 of any one of SEQ ID NOs: 12-14. In some embodiments, a linker may have an amino acid sequence comprising SEQ ID NO:33, which sets forth residues 154-195 of any one of SEQ ID NOs: 12-14.

As used herein, with respect to a protein, the term "recombinant" or "engineered" means having an altered amino acid sequence as a result of the application of genetic engineering techniques to nucleic acids which encode the protein, and cells or organisms which express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers to a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein with respect to recombinant proteins, the term "modification" means any insertion, deletion, or substitution of an amino acid residue in the recombinant sequence relative to a reference sequence (e.g., a wild-type or a native sequence).

As used herein, the terms "recognition sequence" or "recognition site" refer to a DNA sequence that is bound and cleaved by an endonuclease. In the case of a meganuclease, a recognition sequence comprises a pair of inverted, 9 basepair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' "overhangs". "Overhangs," or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence.

As used herein, the term "target site" or "target sequence" refers to a region of the chromosomal DNA of a cell comprising a recognition sequence for a nuclease.

As used herein, the term "DNA-binding affinity" or "binding affinity" means the tendency of a meganuclease to non-covalently associate with a reference DNA molecule (e.g., a recognition sequence or an arbitrary sequence). Binding affinity is measured by a dissociation constant, Kd. As used herein, a nuclease has "altered" binding affinity if the Kd of the nuclease for a reference recognition sequence is increased or decreased by a statistically significant percent change, or biologically significant amount (e.g., at least 2×, or 2× to 10×), relative to a reference nuclease.

As used herein, the term "specificity" means the ability of a nuclease to recognize and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific nuclease is capable of cleaving only one or a very few recognition sequences. Specificity can be determined by any method known in the art.

As used herein, a meganuclease has "altered" specificity if it binds to and cleaves a recognition sequence which is not bound to and cleaved by a reference meganuclease (e.g., a wild-type) under physiological conditions, or if the rate of cleavage of a recognition sequence is increased or decreased by a biologically significant amount (e.g., at least 2×, or 2×-10×) relative to a reference meganuclease.

In some embodiments, the presently disclosed engineered meganucleases have improved (i.e., increased) specificity for the target recognition sequence that comprises SEQ ID NO: 10 (i.e., HBV 11-12) as compared to the HBV 11-12×.26 meganuclease (the amino acid sequence of which is set forth as SEQ ID NO: 14). Thus, in certain embodiments, the presently disclosed engineered meganucleases exhibit reduced off-target cleavage as compared to the HBV 11-12×.26 meganuclease. Off-target cleavage by a meganuclease can be measured using any method known in the art, including for example, oligo capture analysis as described here, a T7 endonuclease (T7E) assay as described herein, digital PCR as described herein, targeted sequencing of particular off-target sites, exome sequencing, whole genome sequencing, direct in situ breaks labeling enrichment on streptavidin and next-generation sequencing (BLESS), genome-wide, unbiased identification of DSBs enabled by sequencing (GUIDE-seq), and linear amplification-mediated high-throughput genome-wide translocation sequencing (LAM-HTGTS) (see, e.g., Zischewski et al. (2017), Biotechnology Advances 35(1):95-104, which is incorporated by reference in its entirety).

As used herein, the term "homologous recombination" or "HR" refers to the natural, cellular process in which a double-stranded DNA-break is repaired using a homologous DNA sequence as the repair template (see, e.g. Cahill et al. (2006), Front. Biosci. 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), Front. Biosci. 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered meganucleases can be used to effectively knock-out a gene in a population of cells.

As used herein, "homology arms" or "sequences homologous to sequences flanking a meganuclease cleavage site" refer to sequences flanking the 5' and 3' ends of a nucleic acid molecule which promote insertion of the nucleic acid molecule into a cleavage site generated by a meganuclease. In general, homology arms can have a length of at least 50 base pairs, preferably at least 100 base pairs, and up to 2000 base pairs or more, and can have at least 90%, preferably at least 95%, or more, sequence homology to their corresponding sequences in the genome.

As used herein with respect to both amino acid sequences and nucleic acid sequences, the terms "percent identity," "sequence identity," "percentage similarity," "sequence similarity" and the like refer to a measure of the degree of similarity of two sequences based upon an alignment of the sequences which maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information, and are described in, for example, Altschul et al. (1990), J. Mol. Biol. 215:403-410; Gish and States (1993), Nature Genet. 3:266-272; Madden et al. (1996), Meth. Enzymol. 266:131-141; Altschul et al. (1997), Nucleic Acids Res. 25:33 89-3402); Zhang et al. (2000), J. Comput. Biol. 7(1-2):203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm:

word size=11; gap opening penalty=−5; gap extension penalty=−2; match reward=1; and mismatch penalty=−3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first protein corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the term "recognition half-site," "recognition sequence half-site," or simply "half-site" means a nucleic acid sequence in a double-stranded DNA molecule which is recognized by a monomer of a homodimeric or heterodimeric meganuclease, or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of SEQ ID NO: 12 or 13. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In particular embodiments, a hypervariable region comprises between about 15-20 residues that exhibit variability and can be modified to influence base preference and/or DNA-binding affinity.

In some embodiments, variable residues within a hypervariable region correspond to one or more of positions 24, 26, 28, 30, 32, 33, 38, 40, 42, 44, 46, 68, 70, 75, and 77 of SEQ ID NO: 12 or 13.

In some embodiments, variable residues within a hypervariable region correspond to one or more of positions 215, 217, 219, 221, 223, 224, 229, 231, 233, 235, 237, 261, 266, and 268 of SEQ ID NO: 12 or 13. In some embodiments, variable residues within a hypervariable region further correspond to one or more of positions 239, 241, 263, and 264 of SEQ ID NO: 12, or one or more of positions 241, 262, 263, and 264 of SEQ ID NO: 13. In other embodiments, variable residues within a hypervariable region correspond to one or more of positions In other embodiments, variable residues within a hypervariable region correspond to one or more of positions 215, 217, 219, 221, 223, 224, 229, 231, 233, 235, 237, 239, 241, 259, 261, 262, 263, 264, 266, and 268 of SEQ ID NO: 12 or 13.

The terms "recombinant DNA construct," "recombinant construct," "expression cassette," "expression construct," "chimeric construct," "construct," and "recombinant DNA fragment" are used interchangeably herein and are single or double-stranded polynucleotides. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used then the choice of vector is dependent upon the method that will be used to transform host cells as is well known to those skilled in the art. Vectors can include, without limitation, plasmid vectors and recombinant viral vectors (e.g., AAV vectors), or any other vector known in that art suitable for delivering a gene encoding a meganuclease of the invention to a target cell. The skilled artisan is well aware of the genetic elements that must be present on the vector in order to successfully transform, select and propagate host cells comprising any of the isolated nucleotides or nucleic acid sequences of the invention.

As used herein, a "vector" can also refer to a viral vector. Viral vectors can include, without limitation, retroviral vectors, lentiviral vectors, adenoviral vectors, and adeno-associated viral vectors (AAV).

As used herein, a "polycistronic" mRNA refers to a single messenger RNA that comprises two or more coding sequences (i.e., cistrons) and encodes more than one protein. A polycistronic mRNA can comprise any element known in the art to allow for the translation of two or more genes from the same mRNA molecule including, but not limited to, an IRES element, a T2A element, a P2A element, an E2A element, and an F2A element.

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions or stimuli or further genetic modifications that would induce expression of altered genotype or phenotype.

As used herein, the terms "treatment" or "treating a subject" refers to the administration of an engineered meganuclease of the invention, or a nucleic acid encoding an engineered meganuclease of the invention to a subject infected with HBV for the purpose of slowing or stopping the rate of HBV proliferation of the virus by cleaving the genome of at least one HBV particle. Such treatment reduces or prevents transfection and replication of HBV in the subject, and provides either partial or complete relief of one or more symptoms of HBV in the subject. Means to assess alleviation of symptoms of HBV infection may include measurement of liver functions by determining levels of the enzyme alanine aminotransferase (ALT) or by measuring sero conversion, namely disappearance and/or reduction of the circulating HBeAg and/or HBsAg levels. Further, alleviation or reduction of symptoms of HBV can be determined by examining liver biopsies and measuring the level of tissue fibrosis by methods well known in the art. The number of circulating viral particles can be determined for example by measuring HBV DNA levels using PCR or by detecting HBsAg levels in the blood. The terms "treatment" or "treating a subject" can further refer to the administration of a cell (e.g., hepatocyte cell) comprising a nucleic acid encoding an engineered meganuclease, wherein the cell is delivered to a target tissue (e.g., liver) and produces the engineered meganuclease in an amount sufficient to treat an HBV infection in the subject, thereby resulting in either partial or complete relief of one or more symptoms of HBV. In some aspects, an engineered meganuclease of the invention, a nucleic acid encoding the same, or a genetically-modified cell or population of genetically-modified cells described herein is administered during treatment in the form of a pharmaceutical composition of the invention.

The term "Hepatitis B Virus infection" refers to any condition related to or resulting from infection with a Hepatitis B virus, such as chronic liver diseases/disorders, inflammations, fibrotic conditions and proliferative disorders, such as liver cancers. Chronic persistent HBV infection can cause fatigue, liver damage, cirrhosis of the liver, and hepatocellular carcinoma, a primary liver cancer.

The terms "proliferating" and "proliferation" as used herein refer to HBV viruses or HBV cccDNA actively dividing and/or infecting human cells. Thus, reduction in proliferation refers to any decrease in the proliferation of HBV including reduction of at least 1%, 2%, 3%, 4%, 5%, 10%, 15%, 20%, 25%, 30%, 40%, 50%, 60%, 70%, 80%, 90%, 91%, 92%, 93%, 94%, 95%, 96%, 97%, 98%, 99%, or 100% when compared to an appropriate control not having been administered the engineered meganuclease, or nucleic acid encoding the engineered meganuclease, disclosed herein. Throughout this application, the term "proliferative disorder" refers to any disease/disorder marked by unwanted or aberrant proliferation of cells or tissue. As used herein, the term "proliferative disorder" also refers to conditions in which the unregulated and/or abnormal growth of cells can lead to the development of an unwanted condition or disease, which can be cancerous or non-cancerous.

The term "effective amount" or "therapeutically effective amount" refers to an amount sufficient to effect beneficial or desirable biological and/or clinical results. The therapeutically effective amount will vary depending on the formulation or composition used, the disease and its severity and the age, weight, physical condition and responsiveness of the subject to be treated. In specific embodiments, an effective amount of the engineered meganuclease or pharmaceutical compositions disclosed herein reduces the level or proliferation of HBV or reduces at least one symptom of HBV in a subject with an HBV infection.

The term "gc/kg" or "gene copies/kilogram" refers to the number of copies of a nucleic acid encoding an engineered meganuclease described herein per weight in kilograms of a subject that is administered the nucleic acid encoding the engineered meganuclease.

The term "lipid nanoparticle" refers to a lipid composition having a typically spherical structure with an average diameter between 10 and 1000 nanometers. In some formulations, lipid nanoparticles can comprise at least one cationic lipid, at least one non-cationic lipid, and at least one conjugated lipid. Lipid nanoparticles known in the art that are suitable for encapsulating nucleic acids, such as mRNA, are contemplated for use in the invention.

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values $\geq 0$ and $\leq 2$ if the variable is inherently continuous.

2.1 Principle of the Invention

The present invention is based, in part, on the discovery of second-generation HBV 11-12 meganucleases which have improved properties when compared to first-generation HBV 11-12 meganucleases, such as improved (i.e., increased) specificity resulting in reduced off-target cutting, and enhanced (i.e., increased) efficiency of cleavage and indel formation at the HBV 11-12 recognition sequence, particularly in cells comprising an integrated copy of the HBV genome.

Like the first-generation HBV11-12×.26 meganuclease, the optimized, second-generation meganucleases of the invention recognize the HBV 11-12 recognition sequence (SEQ ID NO: 10) in the P gene of the Hepatitis B virus that encodes the viral DNA polymerase. The HBV 11-12 recognition sequence is conserved across at least HBV genotypes A-G (SEQ ID NOs: 3-9), which advantageously allows for the presently disclosed engineered meganucleases to target HBV infections around the globe.

Cleavage at the HBV 11-12 recognition sequence can allow for non-homologous end joining (NHEJ) at the cleavage site and can disrupt expression of one or more viral proteins (e.g., viral DNA polymerase) due to NHEJ at the cleavage site that results in insertions, deletions, or frameshift mutations. Alternatively, cleavage of the HBV genome at the HBV 11-12 recognition sequence may promote degradation of the HBV genome and/or HBV cccDNA. Disruption of the expression of the viral protein(s) can reduce or eliminate the infection and/or proliferation of HBV.

Additionally, cleavage at the HBV 11-12 recognition sequence can further allow for homologous recombination of exogenous nucleic acid sequences directly into the HBV genome to disrupt the expression of one or more viral proteins. For example, a "suicide gene" can be introduced into a HBV genome via homologous recombination.

Thus, the present invention encompasses engineered meganucleases which recognize and cleave the HBV 11-12 recognition sequence within a HBV genome. The present invention also encompasses methods of using such engineered meganucleases in a pharmaceutical composition and in methods for treating HBV infection. Further, the invention encompasses pharmaceutical compositions comprising engineered meganuclease proteins, or nucleic acids encoding engineered meganucleases, and the use of such compositions for the treatment of HBV infection and hepatocellular carcinoma (HCC).

2.2 Optimized Meganucleases that Recognize and Cleave the HBV 11-12 Recognition Sequence within the Genome of HBV It is known in the art that it is possible to use a site-specific nuclease to make a DNA break in the genome of a virus, and that such a DNA break can result in permanent modification of the genome via NHEJ such that the HBV virion can no longer divide/replicate or infect human cells. Thus, in some embodiments, the invention can be practiced using engineered meganucleases.

In particular embodiments, the nucleases used to practice the invention are single-chain meganucleases. A single-chain meganuclease comprises an N-terminal subunit and a C-terminal subunit joined by a linker peptide. Each of the two domains recognizes half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

The engineered meganucleases of the invention have been engineered to recognize and cleave the HBV 11-12 recognition sequence (SEQ ID NO: 10). The HBV 11-12 recognition sequence is positioned within the P protein ORF of multiple HBV genotypes. The HBV 11-12 recognition sequence can at least be found in the genome of multiple HBV genotypes, including genotypes A, B, C, D, E, F, and G (e.g., SEQ ID NOs: 3-9, respectively).

Engineered meganucleases of the invention comprise a first subunit, comprising a first hypervariable (HVR1) region, and a second subunit, comprising a second hypervariable (HVR2) region. Further, the first subunit binds to a first recognition half-site in the recognition sequence (i.e., the HBV11 half-site), and the second subunit binds to a second recognition half-site in the recognition sequence (i.e., the HBV12 half-site). In embodiments where the engineered meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit. Exemplary engineered meganucleases that recognize and cleave the HBV 11-12 recognition sequence are provided in Table 1.

nucleases, when delivered to a population of HBV-infected target cells, is able to generate a greater percentage of virions or cells with a cleavage and/or indel in the HBV genome (either incorporated or unincorporated). In some of these embodiments, the population of HBV or target cells comprises at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or more of HBV or target cells comprising a cleavage and/or indel in the HBV genome (either incorporated or unincorporated). Cleavage and/or indel formation by a meganuclease can be measured using any method known in the art, including T7E assay, digital PCR, mismatch detection assays, mismatch cleavage assay, high-resolution melting analysis (HRMA), heteroduplex mobility assay, sequencing, and fluorescent PCR capillary gel electrophoresis (see, e.g., Zischewski et al. (2017) Biotechnology Advances 35(1):95-104, which is incorporated by reference in its entirety).

2.3 Methods for Delivering and Expressing Optimized Meganucleases

Disclosed herein are methods for treating an HBV infection or HCC in a subject. Likewise, methods are provided for reducing the symptoms of an HBV infection and reducing the amount of HBV, reducing the rate of proliferation of HBV or treating HCC in a subject comprising administering a pharmaceutical composition comprising a pharmaceutically acceptable carrier and an engineered meganuclease disclosed herein (or a nucleic acid encoding the engineered meganuclease or a cell expressing the engineered meganuclease). In the methods of the invention, an engineered meganuclease disclosed herein can be delivered to and/or expressed from DNA/RNA in target cells that can provide the engineered meganuclease to the HBV genome.

Engineered meganucleases disclosed herein can be delivered into a cell in the form of protein or, preferably, as a nucleic acid encoding the engineered meganuclease. Such nucleic acid can be DNA (e.g., circular or linearized plasmid DNA or PCR products) or RNA (e.g., mRNA). For embodiments in which the engineered meganuclease coding sequence is delivered in DNA form, it should be operably linked to a promoter to facilitate transcription of the nucle-

TABLE 1

Exemplary engineered meganucleases which recognize and cleave the HBV 11-12 recognition sequence (SEQ ID NO: 10).

| Meganuclease | AA SEQ ID | HBV11 Subunit Residues | HBV11 Subunit SEQ ID | HVR1 Residues | *HVR1 % | HBV12 Subunit Residues | HBV12 Subunit SEQ ID | HVR2 Residues | *HVR2 % |
|---|---|---|---|---|---|---|---|---|---|
| HBV 11-12L.363 | 12 | 198-344 | 15 | 215-270 | 85.71 | 7-153 | 18 | 24-79 | 96.43 |
| HBV 11-12L.367 | 13 | 198-344 | 16 | 215-270 | 85.71 | 7-153 | 19 | 24-79 | 96.43 |
| HBV 11-12x.26 | 14 | 198-344 | 17 | 215-270 | 100 | 7-153 | 20 | 24-79 | 100 |

*"HVR1 %" and "HVR2 %" represent the amino acid sequence identity between the HVR1 and HVR2 regions, respectively, of each meganuclease and the HVR1 and HVR2 regions, respectively, of the HBV 11-12x.26 meganuclease.

In some embodiments, the presently disclosed engineered meganucleases exhibit at least one optimized characteristic in comparison to the first-generation meganuclease HBV 11-12x.26. Such optimized characteristics include improved (i.e. increased) specificity resulting in reduced off-target cutting, and enhanced (i.e., increased) efficiency of cleavage and indel (i.e., insertion or deletion) formation at the HBV 11-12 recognition sequence, particularly in cells comprising an integrated copy of the HBV genome. Thus, in particular embodiments, the presently disclosed engineered megaase gene. Mammalian promoters suitable for the invention include constitutive promoters such as the cytomegalovirus early (CMV) promoter (Thomsen et al. (1984), Proc Natl Acad Sci USA. 81(3):659-63) or the SV40 early promoter (Benoist and Chambon (1981), Nature. 290(5804):304-10) as well as inducible promoters such as the tetracycline-inducible promoter (Dingermann et al. (1992), Mol Cell Biol. 12(9):4038-45). An engineered meganuclease of the invention can also be operably linked to a synthetic promoter. Synthetic promoters can include, without limitation, the JeT promoter (WO 2002/012514). In specific embodiments, a nucleic acid sequence encoding an engineered meganuclease as disclosed herein can be operably linked to a liver-specific promoter. Examples of liver-specific promoters include, without limitation, human alpha-1 antitrypsin promoter, hybrid liver-specific promoter (hepatic locus control region from ApoE gene (ApoE-HCR) and a liver-specific alpha1-antitrypsin promoter), human thyroxine binding globulin (TBG) promoter, and apolipoprotein A-II promoter.

In specific embodiments, a nucleic acid sequence encoding at least one engineered meganuclease is delivered on a recombinant DNA construct or expression cassette. For example, the recombinant DNA construct can comprise an expression cassette (i.e., "cassette") comprising a promoter and a nucleic acid sequence encoding an engineered meganuclease described herein. In other embodiments, the recombinant DNA construct comprises at least a first cassette and a second cassette, wherein the first cassette comprises a promoter and a nucleic acid sequence encoding an engineered meganuclease described herein, and wherein the second cassette comprises a promoter and a nucleic acid sequence encoding a second engineered meganuclease which recognizes and cleaves a second recognition sequence which is present in a Hepatitis B virus genome but differs from SEQ ID NO: 10. Non-limiting examples of other recognition sequences within the genome of a Hepatitis B virus include the HBV 5-6 recognition sequence (set forth as SEQ ID NO: 21).

In other embodiments, the recombinant DNA construct comprises a cassette comprising a promoter and a polycistronic nucleic acid sequence, wherein the promoter drives expression of the polycistronic nucleic acid sequence to generate a polycistronic mRNA described herein in a target cell.

In some embodiments, mRNA encoding an engineered meganuclease is delivered to a cell because this reduces the likelihood that the gene encoding the engineered meganuclease will integrate into the genome of the cell. Such mRNA encoding an engineered meganuclease can be produced using methods known in the art such as in vitro transcription. In some embodiments, the mRNA is 5' capped using 7-methyl-guanosine, anti-reverse cap analogs (ARCA) (U.S. Pat. No. 7,074,596), CleanCap® analogs such as Cap 1 analogs (Trilink, San Diego, Calif.), or enzymatically capped using vaccinia capping enzyme or similar. In some embodiments, the mRNA may be polyadenylated. The mRNA may contain various 5' and 3' untranslated sequence elements to enhance expression the encoded engineered meganuclease and/or stability of the mRNA itself. Such elements can include, for example, posttranslational regulatory elements such as a woodchuck hepatitis virus posttranslational regulatory element. The mRNA may contain nucleoside analogs or naturally-occurring nucleosides, such as pseudouridine, 5-methylcytidine, N6-methyladenosine, 5-methyluridine, or 2-thiouridine. Additional nucleoside analogs include, for example, those described in U.S. Pat. No. 8,278,036.

In particular embodiments, an mRNA encoding an engineered nuclease of the invention can be a polycistronic mRNA encoding two or more of the presently disclosed meganucleases which are simultaneously expressed in a cell. In some embodiments, a polycistronic mRNA can encode at least a first and a second engineered meganuclease, wherein the first engineered meganuclease is an engineered meganuclease described herein, and wherein the second engineered meganuclease recognizes and cleaves a second recognition sequence in the HBV genome that differs from SEQ ID NO: 10 (e.g., the HBV 5-6 recognition sequence), such that the HBV genome is cleaved at multiple sites. In some embodiments, a polycistronic mRNA can encode an engineered meganuclease described herein and at least one additional protein which induces a therapeutically beneficial effect in the cell. A polycistronic mRNA of the invention can comprise any element known in the art to allow for the translation of two or more genes from the same mRNA molecule including, but not limited to, an IRES element, a T2A element, a P2A element, an E2A element, and an F2A element.

In another particular embodiment, a nucleic acid encoding an endonuclease of the invention can be introduced into the cell using a single-stranded DNA template. The single-stranded DNA can further comprise a 5' and/or a 3' AAV inverted terminal repeat (ITR) upstream and/or downstream of the sequence encoding the engineered meganuclease. In other embodiments, the single-stranded DNA can further comprise a 5' and/or a 3' homology arm upstream and/or downstream of the sequence encoding the engineered meganuclease.

In another particular embodiment, genes encoding an endonuclease of the invention can be introduced into a cell using a linearized DNA template. In some examples, a plasmid DNA encoding an endonuclease can be digested by one or more restriction enzymes such that the circular plasmid DNA is linearized prior to being introduced into a cell.

In some embodiments, the methods comprise delivering an engineered meganuclease described herein (or a nucleic acid encoding the same) and a nucleic acid comprising a polynucleotide sequence encoding a suicide gene and sequences homologous to sequences flanking the meganuclease cleavage site, wherein the engineered meganuclease recognizes and cleaves a recognition sequence comprising SEQ ID NO: 10 within the Hepatitis B virus genome, thus cleaving the HBV genome, wherein the suicide gene is inserted into the cleaved HBV genome by homologous recombination.

A suicide gene is a nucleic acid that encodes a product that causes cell death by itself or in the presence of other compounds. A representative example of such a suicide gene is one that encodes thymidine kinase of herpes simplex virus. Additional examples are genes that encode thymidine kinase of varicella zoster virus and the bacterial gene cytosine deaminase that can convert 5-fluorocytosine to the highly toxic compound 5-fluorouracil. Suicide genes also include as non-limiting examples genes that encode caspase-9, caspase-8, or cytosine deaminase. In some examples, caspase-9 can be activated using a specific chemical inducer of dimerization (CID). In some embodiments, the suicide gene is directly lethal to the HBV or a target cell (e.g., HCC cell). In some such embodiments, the directly lethal suicide gene encodes a toxic polypeptide or a pro-apoptotic protein. In some embodiments, the suicide gene is indirectly lethal to the target cell, and directs the subject's own immune system to kill the target cell. In some such embodiments, the indirectly lethal suicide gene encodes a cell surface protein which is recognized as foreign by the subject's immune system and is targeted by a humoral or cellular immune response. In other such embodiments, the indirectly lethal suicide gene encodes a polypeptide which is presented by an MHC Class I molecule, is recognized as foreign by the subject's immune system, and is targeted by a cytotoxic immune response.

Purified meganuclease proteins can be delivered into cells to cleave genomic DNA by a variety of different mechanisms known in the art, including those further detailed herein below.

The target tissue(s) for delivery of engineered meganucleases of the invention include, without limitation, cells of the liver, such as a hepatocyte cell or preferably a primary hepatocyte, more preferably a human hepatocyte or a human primary hepatocyte, a HepG2.2.15 or a HepG2-hNTCP cell. As discussed, meganucleases of the invention can be delivered as purified protein or as RNA or DNA encoding the meganuclease. In one embodiment, meganuclease proteins, or mRNA, or DNA vectors encoding meganucleases, are supplied to target cells (e.g., cells in the liver) via injection directly to the target tissue. Alternatively, meganuclease protein, mRNA, DNA, or cells expressing meganucleases can be delivered systemically via the circulatory system.

In some embodiments, meganuclease proteins, DNA/mRNA encoding meganucleases, or cells expressing meganuclease proteins are formulated for systemic administration, or administration to target tissues, in a pharmaceutically acceptable carrier in accordance with known techniques. See, e.g., Remington, The Science And Practice of Pharmacy (21st ed., Philadelphia, Lippincott, Williams & Wilkins, 2005). In the manufacture of a pharmaceutical formulation according to the invention, proteins/RNA/mRNA/cells are typically admixed with a pharmaceutically acceptable carrier. The carrier must, of course, be acceptable in the sense of being compatible with any other ingredients in the formulation and must not be deleterious to the patient. The carrier can be a solid or a liquid, or both, and can be formulated with the compound as a unit-dose formulation.

In some embodiments, about $1\times10^{10}$ gc/kg to about $1\times10^{14}$ gc/kg (e.g., $1\times10^{10}$ gc/kg, $1\times10^{11}$ gc/kg, $1\times10^{12}$ gc/kg, $1\times10^{13}$ gc/kg, or $1\times10^{14}$ gc/kg) of a nucleic acid encoding the engineered meganuclease is administered to the subject. In some embodiments, at least about $1\times10^{10}$ gc/kg, at least about $1\times10^{11}$ gc/kg, at least about $1\times10^{12}$ gc/kg, at least about $1\times10^{13}$ gc/kg, or at least about $1\times10^{14}$ gc/kg of a nucleic acid encoding the engineered meganuclease is administered to the subject. In some embodiments, about $1\times10^{10}$ gc/kg to about $1\times10^{11}$ gc/kg, about $1\times10^{11}$ gc/kg to about $1\times10^{12}$ gc/kg, about $1\times10^{12}$ gc/kg to about $1\times10^{13}$ gc/kg, or about $1\times10^{13}$ gc/kg to about $1\times10^{14}$ gc/kg of a nucleic acid encoding the engineered meganuclease is administered to the subject.

In some embodiments, the subject is administered a lipid nanoparticle formulation with about 0.1 mg/kg to about 3 mg/kg of mRNA encoding an engineered meganuclease. In some embodiments, the subject is administered a lipid nanoparticle formulation with at least about 0.1 mg/kg, at least about 0.25 mg/kg, at least about 0.5 mg/kg, at least about 0.75 mg/kg, at least about 1.0 mg/kg, at least about 1.5 mg/kg, at least about 2.0 mg/kg, at least about 2.5 mg/kg, or at least about 3.0 mg/kg of mRNA encoding an engineered meganuclease. In some embodiments, the subject is administered a lipid nanoparticle formulation within about 0.1 mg/kg to about 0.25 mg/kg, about 0.25 mg/kg to about 0.5 mg/kg, about 0.5 mg/kg to about 0.75 mg/kg, about 0.75 mg/kg to about 1.0 mg/kg, about 1.0 mg/kg to about 1.5 mg/kg, about 1.5 mg/kg to about 2.0 mg/kg, about 2.0 mg/kg to about 2.5 mg/kg, or about 2.5 mg/kg to about 3.0 mg/kg of mRNA encoding and engineered meganuclease.

In some embodiments, meganuclease proteins, or DNA/mRNA encoding the meganuclease, are coupled to a cell penetrating peptide or targeting ligand to facilitate cellular uptake. Examples of cell penetrating peptides known in the art include poly-arginine (Jearawiriyapaisarn, et al. (2008) Mol Ther. 16:1624-9), TAT peptide from the HIV virus (Hudecz et al. (2005), Med. Res. Rev. 25: 679-736), MPG (Simeoni, et al. (2003) Nucleic Acids Res. 31:2717-2724), Pep-1 (Deshayes et al. (2004) Biochemistry 43: 7698-7706, and HSV-1 VP-22 (Deshayes et al. (2005) Cell Mol Life Sci. 62:1839-49. In an alternative embodiment, meganuclease proteins, or DNA/mRNA encoding meganucleases, are coupled covalently or non-covalently to an antibody that recognizes a specific cell-surface receptor expressed on target cells such that the meganuclease protein/DNA/mRNA binds to and is internalized by the target cells. Alternatively, meganuclease protein/DNA/mRNA can be coupled covalently or non-covalently to the natural ligand (or a portion of the natural ligand) for such a cell-surface receptor. (McCall, et al. (2014) Tissue Barriers. 2(4):e944449; Dinda, et al. (2013) Curr Pharm Biotechnol. 14:1264-74; Kang, et al. (2014) Curr Pharm Biotechnol. 15(3):220-30; Qian et al. (2014) Expert Opin Drug Metab Toxicol. 10(11):1491-508).

In some embodiments, meganuclease proteins, or DNA/mRNA encoding meganucleases, are encapsulated within biodegradable hydrogels for injection or implantation within the desired region of the liver (e.g., in proximity to hepatic sinusoidal endothelial cells or hematopoietic endothelial cells, or progenitor cells which differentiate into the same). Hydrogels can provide sustained and tunable release of the therapeutic payload to the desired region of the target tissue without the need for frequent injections, and stimuli-responsive materials (e.g., temperature- and pH-responsive hydrogels) can be designed to release the payload in response to environmental or externally applied cues (Kang Derwent et al. (2008) Trans Am Ophthalmol Soc. 106:206-214).

In some embodiments, meganuclease proteins, or DNA/mRNA encoding meganucleases, are coupled covalently or, preferably, non-covalently to a nanoparticle or encapsulated within such a nanoparticle using methods known in the art (Sharma, et al. (2014) Biomed Res Int. 2014). A nanoparticle is a nanoscale delivery system whose length scale is <1 □m, preferably <100 nm. Such nanoparticles may be designed using a core composed of metal, lipid, polymer, or biological macromolecule, and multiple copies of the meganuclease proteins, mRNA, or DNA can be attached to or encapsulated with the nanoparticle core. This increases the copy number of the protein/mRNA/DNA that is delivered to each cell and, so, increases the intracellular expression of each meganuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) Biomaterials. 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the meganuclease proteins or DNA/mRNA encoding the meganucleases are encapsulated within liposomes or complexed using cationic lipids (see, e.g., LIPOFECTAMINE transfection reagent, Life Technologies Corp., Carlsbad, Calif.; Zuris et al. (2015) Nat Biotechnol. 33: 73-80; Mishra et al. (2011) J Drug Deliv. 2011:863734). The liposome and lipoplex formulations can protect the payload from degradation, enhance accumulation and retention at the target site, and facilitate cellular uptake and delivery efficiency through fusion with and/or disruption of the cellular membranes of the target cells.

In some embodiments, meganuclease proteins, or DNA/mRNA encoding meganucleases, are encapsulated within polymeric scaffolds (e.g., PLGA) or complexed using cationic polymers (e.g., PEI, PLL) (Tamboli et al. (2011) Ther Deliv. 2(4): 523-536). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, meganuclease proteins, or DNA/mRNA encoding engineered meganucleases, are combined with amphiphilic molecules that self-assemble into micelles (Tong et al. (2007) J Gene Med. 9(11): 956-66). Polymeric micelles may include a micellar shell formed with a hydrophilic polymer (e.g., polyethyleneglycol) that can prevent aggregation, mask charge interactions, and reduce nonspecific interactions.

In some embodiments, meganuclease proteins, or DNA/mRNA encoding meganucleases, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in U.S. Pat. Nos. 6,015,832, 6,506,803, 6,635,676, 6,559,189, and 7,767,216, each of which is incorporated herein by reference in its entirety.

In some embodiments, meganuclease proteins, or DNA/mRNA encoding meganucleases, are covalently attached to, or non-covalently associated with, multifunctional polymer conjugates, DNA dendrimers, and polymeric dendrimers (Mastorakos et al. (2015) Nanoscale. 7(9): 3845-56; Cheng et al. (2008) J Pharm Sci. 97(1): 123-43). The dendrimer generation can control the payload capacity and size, and can provide a high drug payload capacity. Moreover, display of multiple surface groups can be leveraged to improve stability, reduce nonspecific interactions, and enhance cell-specific targeting and drug release.

In some embodiments, genes encoding a meganuclease are delivered using a viral vector. Such vectors are known in the art and include retroviral vectors, lentiviral vectors, adenoviral vectors, and adeno-associated virus (AAV) vectors (reviewed in Vannucci, et al. (2013 New Microbiol. 36:1-22). In some embodiments, the viral vectors are injected directly into target tissues (e.g., liver tissue). In alternative embodiments, the viral vectors are delivered systemically via the circulatory system. It is known in the art that different AAV vectors tend to localize to different tissues. In liver target tissues, effective transduction of hepatocytes has been shown, for example, with AAV serotypes 2, 8, and 9 (Sands (2011) Methods Mol. Biol. 807: 141-157). AAV vectors can also be self-complementary such that they do not require second-strand DNA synthesis in the host cell (McCarty, et al. (2001) Gene Ther. 8:1248-54).

If the meganuclease genes are delivered in DNA form (e.g. plasmid) and/or via a viral vector (e.g. AAV) they must be operably linked to a promoter. In some embodiments, this can be a viral promoter such as endogenous promoters from the viral vector (e.g. the LTR of a lentiviral vector) or the well-known cytomegalovirus- or SV40 virus-early promoters. In a preferred embodiment, meganuclease genes are operably linked to a promoter that drives gene expression preferentially in the target cells. Examples of liver-specific promoters include, without limitation, human alpha-1 antitrypsin promoter, hybrid liver-specific promoter (hepatic locus control region from ApoE gene (ApoE-HCR) and a liver-specific alpha1-antitrypsin promoter), human thyroxine binding globulin (TBG) promoter, and apolipoprotein A-II promoter.

In particular embodiments, the viral vector comprises a cassette comprising a promoter and a nucleic acid sequence encoding an engineered meganuclease described herein. The viral vector could also comprise two or more cassettes, wherein at least a first cassette comprises a promoter and a nucleic acid sequence encoding an engineered meganuclease described herein, and wherein at least a second cassette comprises a promoter and a nucleic acid sequence encoding an engineered meganuclease that has specificity for a different HBV recognition sequence other than the HBV 11-12 recognition sequence. In some embodiments, the viral vector comprises one cassette comprising a promoter and a polycistronic nucleic acid sequence, wherein the promoter drives expression of the polycistronic nucleic acid sequence to generate a polycistronic mRNA, such as polycistronic mRNA encoding an engineered meganuclease, described herein in a target cell.

Methods and compositions are provided for delivering a meganuclease disclosed herein to the liver of a subject infected with HBV. In one embodiment, native hepatocytes which have been removed from the mammal can be transduced with a vector which encodes the engineered meganuclease. Alternatively, native hepatocytes of the HBV-infected subject can be transduced ex vivo with an adenoviral vector (i.e., an AAV vector) which encodes the engineered meganuclease and/or a molecule that stimulates liver regeneration, such as a hepatotoxin. Preferably the hepatotoxin is uPA, and has been modified to inhibit its secretion from the hepatocyte once expressed by the viral vector. In another embodiment, the vector encodes tPA, which can stimulate hepatocyte regeneration de novo. The transduced hepatocytes which have been removed from the mammal can then be returned to the mammal, where conditions are provided which are conducive to expression of the engineered meganuclease. Typically the transduced hepatocytes can be returned to the patient by infusion through the spleen or portal vasculature, and administration may be single or multiple over a period of 1 to 5 or more days.

In an in vivo aspect of the methods of the invention, a retroviral, pseudotype or adenoviral associated vector (i.e., an AAV vector) is constructed which encodes the engineered meganuclease and is administered to the subject. Administration of a vector encoding the engineered meganuclease can occur with administration of an adenoviral vector that encodes a secretion-impaired hepatotoxin, or encodes tPA, which stimulates hepatocyte regeneration without acting as a hepatotoxin.

Appropriate doses will depend, among other factors, on the specifics of any AAV vector chosen (e.g., serotype, etc.), on the route of administration, on the subject being treated (i.e., age, weight, sex, and general condition of the subject), and the mode of administration. Thus, the appropriate dosage may vary from patient to patient. An appropriate effective amount can be readily determined by one of skill in the art. Dosage treatment may be a single dose schedule or a multiple dose schedule. Moreover, the subject may be administered as many doses as appropriate. One of skill in the art can readily determine an appropriate number of doses. The dosage may need to be adjusted to take into consideration an alternative route of administration, or balance the therapeutic benefit against any side effects.

2.4 Pharmaceutical Compositions

In some embodiments, the invention provides a pharmaceutical composition comprising a pharmaceutically acceptable carrier and an engineered meganuclease of the invention, or a pharmaceutically acceptable carrier and a polynucleotide comprising a nucleic acid encoding an engineered meganuclease of the invention. In other embodiments, the invention provides a pharmaceutical composition comprising a pharmaceutically acceptable carrier and a cell of the invention which can be delivered to a target tissue where the cell expresses the engineered meganuclease as disclosed herein. Pharmaceutical compositions of the invention can be useful for treating a subject having HBV, reducing the level or proliferation of HBV, reducing at least one symptom of HBV, or treating HCC.

Pharmaceutical compositions can be designed or selected according to the genotype of the target HBV strain. As described in detail herein, the meganucleases of the invention have been engineered to recognize and cleave a recognition sequence in specific genotypes of HBV. HBV 11-12 meganucleases (e.g., SEQ ID NOs: 12 and 13), recognize and cleave the HBV 11-12 recognition sequence that is at least found in the genome of HBV genotypes A, B, C, D, E, F, and G (e.g., SEQ ID NOs: 3-9, respectively). Further, recognition sequences of the engineered meganucleases disclosed herein can be found in isolates of HBV genotypes A, B, C, D, E, F, and G that do not share 100% sequence identity to the respective genotype examples provided in SEQ ID NOs: 3-9. As used herein, HBV "isolates" can share at least 80%, at least 85%, at least 90%, at least 91%, at least 92%, at least 93%, at least 94%, at least 95%, at least 96%, at least 97%, at least 98%, at least 99%, or more sequence identity with the corresponding genotype example provided in any of SEQ ID NOs: 3-9. In some embodiments, the pharmaceutical compositions disclosed herein can be administered to a subject having any genotype of HBV comprising a recognition sequence set forth in SEQ ID NO: 10.

Such pharmaceutical compositions can be prepared in accordance with known techniques. See, e.g., Remington, The Science And Practice of Pharmacy (21st ed., Philadelphia, Lippincott, Williams & Wilkins, 2005). In the manufacture of a pharmaceutical formulation according to the invention, meganuclease polypeptides (or DNA/RNA encoding the same or cells expressing the same) are typically admixed with a pharmaceutically acceptable carrier and the resulting composition is administered to a subject. The carrier must, of course, be acceptable in the sense of being compatible with any other ingredients in the formulation and must not be deleterious to the subject. In some embodiments, pharmaceutical compositions of the invention can further comprise one or more additional agents or biological molecules useful in the treatment of a disease in the subject. Likewise, the additional agent(s) and/or biological molecule(s) can be co-administered as a separate composition.

Given that the presently disclosed engineered meganucleases can have improved (i.e., increased) specificity resulting in reduced off-target cutting, and enhanced (i.e., increased) efficiency of cleavage and indel formation, particularly in cells comprising an integrated copy of the HBV genome, as compared to the HBV11-12×.26 meganuclease, in some embodiments, the presently disclosed pharmaceutical compositions comprising optimized engineered meganucleases, nucleic acid sequences encoding the same, or cells expressing the same, also have improved (i.e., increased) efficacy in treating HBV, reducing the level or proliferation of HBV, reducing at least one symptom of HBV, or treating HCC in a subject, when compared to the administration of pharmaceutical compositions comprising the HBV11-12×.26 meganuclease.

In particular embodiments, pharmaceutical compositions of the invention can include combinations of the engineered meganucleases described herein (or nucleic acids encoding engineered meganucleases or cells expressing engineered meganucleases). In other embodiments, pharmaceutical compositions of the invention can include at least two engineered meganucleases (or nucleic acids encoding engineered meganucleases or cells expressing engineered meganucleases), wherein at least a first engineered meganuclease is one described herein that recognizes and cleaves the HBV 11-12 recognition sequence, and wherein at least a second engineered meganuclease recognizes and cleaves a second recognition sequence in the HBV genome other than the HBV 11-12 recognition sequence, such that a single pharmaceutical composition is broadly useful for the treatment of a wide array of HBV genotypes and/or genotype isolates in a subject. Likewise, in other embodiments, pharmaceutical compositions of the invention can include polycistronic mRNAs (or recombinant DNA constructs or viral vectors having cassettes which, when expressed, produce polycistronic mRNAs) that encode multiple engineered meganucleases described herein. In other embodiments, pharmaceutical compositions of the invention can include polycistronic mRNAs (or recombinant DNA constructs or viral vectors having cassettes which, when expressed, produce polycistronic mRNAs) that encode at least two engineered meganucleases, wherein at least a first engineered meganuclease is one described herein that recognizes and cleaves the HBV 11-12 recognition sequence, and wherein at least a second engineered meganuclease recognizes and cleaves a second recognition sequence in the HBV genome other than the HBV 11-12 recognition sequence. Such pharmaceutical compositions are also broadly useful for the treatment of a wide array of HBV genotypes and/or genotype isolates in a subject. In either case, such pharmaceutical compositions can be useful as a single treatment when the specific HBV genotype or isolate is known or unknown in the subject.

For example, pharmaceutical compositions comprising multiple different engineered meganucleases (including at least one of the engineered meganucleases disclosed herein) or comprising nucleic molecules encoding multiple different engineered meganucleases (including at least one of the engineered meganucleases disclosed herein) that target recognition sequences within the HBV genome, can be administered to a patient infected with multiple genotypes of HBV, or infected with unknown genotypes of HBV. Accordingly, providing pharmaceutical compositions with multiple different engineered meganucleases or comprising nucleic molecules encoding multiple different engineered meganucleases affords a flexible option for treatment and control of HBV infection where resources do not allow for accurate genotyping HBV and where fast and broad treatment solutions are desired.

In particular embodiments of the invention, the pharmaceutical composition can comprise one or more mRNAs described herein encapsulated within lipid nanoparticles, which are described elsewhere herein. In particular embodiments, lipid nanoparticles can comprise two or more mRNAs described herein. In other embodiments, lipid nanoparticles can comprise at least two mRNAs, wherein at least a first mRNA is an mRNA described herein that encodes an engineered meganuclease described herein that recognizes and cleaves the HBV 11-12 recognition sequence, and wherein at least a second mRNA encodes a second engineered meganuclease that recognizes and cleaves a recognition sequence within an HBV genome other than the HBV 11-12 recognition sequence. In other embodiments, lipid nanoparticles can comprise one or more polycistronic mRNAs described herein, wherein each polycistronic mRNA encodes two or more engineered meganucleases, wherein at least one engineered meganuclease is an engineered meganuclease described herein that recognizes and cleaves the HBV 11-12 recognition sequence, and wherein at least a second engineered meganuclease recognizes and cleaves a recognition sequence within a HBV genome other than the HBV 11-12 recognition sequence.

Some lipid nanoparticles contemplated for use in the invention comprise at least one cationic lipid, at least one non-cationic lipid, and at least one conjugated lipid. In more particular examples, lipid nanoparticles can comprise from about 50 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology. In other particular examples, lipid nanoparticles can comprise from about 40 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology.

Cationic lipids can include, for example, one or more of the following: palmitoyi-oleoyl-nor-arginine (PONA), MPDACA, GUADACA, ((6Z,9Z,28Z,31Z)-heptatriaconta-6,9,28,31-tetraen-19-yl 4-(dimethylamino)butanoate) (MC3), LenMC3, CP-LenMC3, γ-LenMC3, CP-γ-LenMC3, MC3MC, MC2MC, MC3 Ether, MC4 Ether, MC3 Amide, Pan-MC3, Pan-MC4 and Pan MC5, 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N-(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2 (spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy) propane (CpLinDMA), N,N-dimethyl-3,4-dioleyloxybenzylamine (DMOB A), 1,2-N,N'-dioleylcarbamyl-3-dimethylaminopropane (DOcarbDAP), 1,2-N,N'-dilinoleylcarbamyl-3-dimethylaminopropane (DLincarbDAP), or mixtures thereof. The cationic lipid can also be DLinDMA, DLin-K-C2-DMA ("XTC2"), MC3, LenMC3, CP-LenMC3, γ-LenMC3, CP-γ-LenMC3, MC3MC, MC2MC, MC3 Ether, MC4 Ether, MC3 Amide, Pan-MC3, Pan-MC4, Pan MC5, or mixtures thereof.

In various embodiments, the cationic lipid may comprise from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 50 mol % to about 60 mol % of the total lipid present in the particle.

In other embodiments, the cationic lipid may comprise from about 40 mol % to about 90 mol %, from about 40 mol % to about 85 mol %, from about 40 mol % to about 80 mol %, from about 40 mol % to about 75 mol %, from about 40 mol % to about 70 mol %, from about 40 mol % to about 65 mol %, or from about 40 mol % to about 60 mol % of the total lipid present in the particle.

The non-cationic lipid may comprise, e.g., one or more anionic lipids and/or neutral lipids. In particular embodiments, the non-cationic lipid comprises one of the following neutral lipid components: (1) cholesterol or a derivative thereof; (2) a phospholipid; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoylphosphatidylethanolamine (SOPE), egg phosphatidylcholine (EPC), and mixtures thereof. In certain embodiments, the phospholipid is DPPC, DSPC, or mixtures thereof.

In some embodiments, the non-cationic lipid (e.g., one or more phospholipids and/or cholesterol) may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cholesterol or a cholesterol derivative, the mixture may comprise up to about 40, 50, or 60 mol % of the total lipid present in the particle.

The conjugated lipid that inhibits aggregation of particles may comprise, e.g., one or more of the following: a polyethyleneglycol (PEG)-lipid conjugate, a polyamide (ATTA)-lipid conjugate, a cationic-polymer-lipid conjugates (CPLs), or mixtures thereof. In one preferred embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-di lauryloxypropyl (C12), a PEG-dimyristyloxypropyl (C14), a PEG-dipalmityloxypropyl (C16), a PEG-distearyloxypropyl (C18), or mixtures thereof.

Additional PEG-lipid conjugates suitable for use in the invention include, but are not limited to, mPEG2000-1,2-di-O-alkyl-sn3-carbomoylglyceride (PEG-C-DOMG). The synthesis of PEG-C-DOMG is described in PCT Application No. PCT/US08/88676. Yet additional PEG-lipid conjugates suitable for use in the invention include, without limitation, 1-[8'-(1,2-dimyristoyl-3-propanoxy)-carboxamido-3',6'-dioxaoctanyl]carbamoyl-w-methyl-poly(ethylene glycol) (2KPEG-DMG). The synthesis of 2KPEG-DMG is described in U.S. Pat. No. 7,404,969.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

In other embodiments, the composition may comprise amphoteric liposomes, which contain at least one positive and at least one negative charge carrier, which differs from the positive one, the isoelectric point of the liposomes being between 4 and 8. This objective is accomplished owing to the fact that liposomes are prepared with a pH-dependent, changing charge.

Liposomal structures with the desired properties are formed, for example, when the amount of membrane-forming or membrane-based cationic charge carriers exceeds that of the anionic charge carriers at a low pH and the ratio is reversed at a higher pH. This is always the case when the ionizable components have a pKa value between 4 and 9. As the pH of the medium drops, all cationic charge carriers are charged more and all anionic charge carriers lose their charge.

Cationic compounds useful for amphoteric liposomes include those cationic compounds previously described herein above. Without limitation, strongly cationic compounds can include, for example: DC-Choi 3-β-[N-(N',N'-dimethylmethane) carbamoyl] cholesterol, TC-Choi 3-β-[N-(N',N',N'-trimethylaminoethane) carbamoyl cholesterol, B GSC bisguanidinium-spermidine-cholesterol, BGTC bisguadinium-tren-cholesterol, DOTAP (1,2-dioleoyloxypropyl)-N,N,N-trimethylammonium chloride, DOSPER (1,3-dioleoyloxy-2-(6-carboxy-spermyl)-propylarnide, DOTMA (1,2-dioleoyloxypropyl)-N,N,N-trimethylamronium chloride) (Lipofectin®), DORIE 1,2-dioleoyloxypropyl)-3-dimethylhydroxyethylammonium bromide, DOSC (1,2-dioleoyl-3-succinyl-sn-glyceryl choline ester), DOGSDSO (1,2-dioleoyl-sn-glycero-3-succinyl-2-hydroxyethyl disulfide omithine), DDAB dimethyldioctadecylammonium bromide, DOGS ((C18)2GlySper3+) N,N-dioctadecylamidoglycol-spermin (Transfectam®) (C18)2Gly+ N,N-dioctadecylamido-glycine, CTAB cetyltrimethylarnmonium bromide, CpyC cetylpyridinium chloride, DOEPC 1,2-dioleoly-sn-glycero-3-ethylphosphocholine or other O-alkyl-phosphatidylcholine or ethanolamines, amides from lysine, arginine or ornithine and phosphatidyl ethanolamine.

Examples of weakly cationic compounds include, without limitation: His-Chol (histaminyl-cholesterol hemisuccinate), Mo-Chol (morpholine-N-ethylamino-cholesterol hemisuccinate), or histidinyl-PE.

Examples of neutral compounds include, without limitation: cholesterol, ceramides, phosphatidyl cholines, phosphatidyl ethanolamines, tetraether lipids, or diacyl glycerols.

Anionic compounds useful for amphoteric liposomes include those non-cationic compounds previously described herein. Without limitation, examples of weakly anionic compounds can include: CHEMS (cholesterol hemisuccinate), alkyl carboxylic acids with 8 to 25 carbon atoms, or diacyl glycerol hemisuccinate. Additional weakly anionic compounds can include the amides of aspartic acid, or glutamic acid and PE as well as PS and its amides with glycine, alanine, glutamine, asparagine, serine, cysteine, threonine, tyrosine, glutamic acid, aspartic acid or other amino acids or aminodicarboxylic acids. According to the same principle, the esters of hydroxycarboxylic acids or hydroxydicarboxylic acids and PS are also weakly anionic compounds.

In some embodiments, amphoteric liposomes may contain a conjugated lipid, such as those described herein above. Particular examples of useful conjugated lipids include, without limitation, PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Particularly preferred are PEG-modified diacylglycerols and dialkylglycerols.

In some embodiments, the neutral lipids may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

Considering the total amount of neutral and conjugated lipids, the remaining balance of the amphoteric liposome can comprise a mixture of cationic compounds and anionic compounds formulated at various ratios. The ratio of cationic to anionic lipid may selected in order to achieve the desired properties of nucleic acid encapsulation, zeta potential, pKa, or other physicochemical property that is at least in part dependent on the presence of charged lipid components.

In some embodiments, the lipid nanoparticles have a composition which specifically enhances delivery and uptake in the liver, and specifically within hepatocytes.

In some embodiments, pharmaceutical compositions of the invention can further comprise one or more additional agents useful in the treatment of HBV infection or HCC in the subject.

The present disclosure also provides engineered meganucleases described herein (or nucleic acids encoding the same or cells expressing the engineered meganucleases) for use as a medicament. The present disclosure further provides the use of an engineered meganuclease described herein (or a nucleic acid encoding the same or cells expressing an engineered meganuclease) in the manufacture of a medicament for treating HBV, for reducing the level or proliferation of HBV, reducing the symptoms associated with HBV, or treating HCC.

2.5 Methods for Producing Recombinant Viral Vectors

In some embodiments, the invention provides viral vectors (e.g., recombinant AAV vectors) for use in the methods of the invention. Recombinant AAV vectors are typically produced in mammalian cell lines such as HEK-293. Because the viral cap and rep genes are removed from the vector to prevent its self-replication to make room for the therapeutic gene(s) to be delivered (e.g. the meganuclease gene), it is necessary to provide these in trans in the packaging cell line. In addition, it is necessary to provide the "helper" (e.g. adenoviral) components necessary to support replication (Cots et al. (2013), Curr. Gene Ther. 13(5): 370-81). Frequently, recombinant AAV vectors are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically produced (manufactured) in cells, precautions must be taken in practicing the current invention to ensure that the engineered meganuclease is not expressed in the packaging cells. Because the viral genomes of the invention may comprise a recognition sequence for the meganuclease, any meganuclease expressed in the packaging cell line may be capable of cleaving the viral genome before it can be packaged into viral particles. This will result in reduced packaging efficiency and/or the packaging of fragmented genomes. Several approaches can be used to prevent meganuclease expression in the packaging cells, including:

The meganuclease can be placed under the control of a tissue-specific promoter that is not active in the packaging cells. For example, if a viral vector is developed for delivery of (a) meganuclease gene(s) to muscle tissue, a muscle-specific promoter can be used. Examples of muscle-specific promoters include C5-12 (Liu, et al. (2004) Hum Gene Ther. 15:783-92), the muscle-specific creatine kinase (MCK) promoter (Yuasa, et al. (2002) Gene Ther. 9:1576-88), or the smooth muscle 22 (SM22) promoter (Haase, et al. (2013) BMC Biotechnol. 13:49-54). Examples of CNS (neuron)-specific promoters include the NSE, Synapsin, and MeCP2 promoters (Lentz, et al. (2012) Neurobiol Dis. 48:179-88). Examples of liver-specific promoters include albumin promoters (such as Palb), human al-antitrypsin (such as Pa1AT), and hemopexin (such as Phpx) (Kramer et al., (2003) Mol. Therapy 7:375-85), hybrid liver-specific promoter (hepatic locus control region from ApoE gene (ApoE-HCR) and a liver-specific alpha1-antitrypsin promoter), human thyroxine binding globulin (TBG) promoter, and apolipoprotein A-II promoter. Examples of eye-specific promoters include opsin, and corneal epithelium-specific K12 promoters (Martin et al. (2002) Methods (28): 267-75) (Tong et al., (2007) J Gene Med, 9:956-66). These promoters, or other tissue-specific promoters known in the art, are not highly-active in HEK-293 cells and, thus, will not be expected to yield significant levels of meganuclease gene expression in packaging cells when incorporated into viral vectors of the present invention. Similarly, the viral vectors of the present invention contemplate the use of other cell lines with the use of incompatible tissue specific promoters (i.e., the well-known HeLa cell line (human epithelial cell) and using the liver-specific hemopexin promoter). Other examples of tissue specific promoters include: synovial sarcomas PDZD4 (cerebellum), C6 (liver), ASBS (muscle), PPP1R12B (heart), SLC5A12 (kidney), cholesterol regulation APOM (liver), ADPRHL1 (heart), and monogenic malformation syndromes TP73L (muscle). (Jacox et al., (2010), PLoS One v. 5(8):e12274).

Alternatively, the vector can be packaged in cells from a different species in which the meganuclease is not likely to be expressed. For example, viral particles can be produced in microbial, insect, or plant cells using mammalian promoters, such as the well-known cytomegalovirus- or SV40 virus-early promoters, which are not active in the non-mammalian packaging cells. In a preferred embodiment, viral particles are produced in insect cells using the baculovirus system as described by Gao, et al. (Gao et al. (2007), J. Biotechnol. 131(2):138-43). A meganuclease under the control of a mammalian promoter is unlikely to be expressed in these cells (Airenne et al. (2013), Mol. Ther. 21(4):739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of a meganuclease. Because these introns are not spliced efficiently from pre-mRNA transcripts in insect cells, insect cells will not express a functional meganuclease and will package the full-length genome. In contrast, mammalian cells to which the resulting recombinant AAV particles are delivered will properly splice the pre-mRNA and will express functional meganuclease protein. Haifeng Chen has reported the use of the HGH and SV40 large T antigen introns to attenuate expression of the toxic proteins barnase and diphtheria toxin fragment A in insect packaging cells, enabling the production of recombinant AAV vectors carrying these toxin genes (Chen, H (2012) Mol Ther Nucleic Acids. 1(11): e57).

The meganuclease gene can be operably linked to an inducible promoter such that a small-molecule inducer is required for meganuclease expression. Examples of inducible promoters include the Tet-On system (Clontech; Chen et al. (2015), BMC Biotechnol. 15(1):4)) and the RheoSwitch system (Intrexon; Sowa et al. (2011), Spine, 36(10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Practicing the current invention using such ligand-inducible transcription activators includes: 1) placing the meganuclease gene under the control of a promoter that responds to the corresponding transcription factor, the meganuclease gene having (a) binding site(s) for the transcription factor; and 2) including the gene encoding the transcription factor in the packaged viral genome The latter step is necessary because the meganuclease will not be expressed in the target cells or tissues following recombinant AAV delivery if the transcription activator is not also provided to the same cells. The transcription activator then induces meganuclease gene expression only in cells or tissues that are treated with the cognate small-molecule activator. This approach is advantageous because it enables meganuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

In another preferred embodiment, recombinant AAV particles are produced in a mammalian cell line that expresses a transcription repressor that prevents expression of the meganuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the meganuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or it can be stably integrated into the genome of the packaging cell such that it is expressed constitutively. Methods to modify common mammalian promoters to incorporate transcription repressor sites are known in the art. For example, Chang and Roninson modified the strong, constitutive CMV and RSV promoters to comprise operators for the Lac repressor and showed that gene expression from the modified promoters was greatly attenuated in cells expressing the repressor (Chang and Roninson (1996), Gene 183:137-42). The use of a non-human transcription repressor ensures that transcription of the meganuclease gene will be repressed only in the packaging cells expressing the repressor and not in target cells or tissues transduced with the resulting recombinant AAV vector.

2.6 Engineered Meganuclease Variants

Embodiments of the invention encompass the engineered meganucleases described herein, and variants thereof. Further embodiments of the invention encompass polynucleotides comprising a nucleic acid sequence encoding the meganucleases described herein, and variants of such polynucleotides.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to recognize and cleave the HBV 11-12 recognition sequence (SEQ ID NO: 10) within the genome of a Hepatitis B virus, and in some embodiments, exhibit at least one improved property over the first-generation HBV 11-12x.26 meganuclease, such as improved (i.e., increased) specificity and enhanced (i.e., increased) efficiency of cleavage and indel formation. Such variants may result, for example, from human manipulation. Biologically active variants of a native polypeptide of the embodiments (e.g., SEQ ID NOs: 12 and 13), or biologically active variants of the recognition half-site binding subunits described herein, will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide or native subunit, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

In some embodiments, engineered meganucleases of the invention can comprise variants of the HVR1 and HVR2 regions disclosed herein. Parental HVR regions can comprise, for example, residues 24-79 or residues 215-270 of the exemplified engineered meganucleases. Thus, variant HVRs can comprise an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 24-79 or residues 215-270 of the engineered meganucleases exemplified herein, such that the variant HVR regions maintain the biological activity of the engineered meganuclease (i.e., binding to and cleaving the recognition sequence). Further, in some embodiments of the invention, a variant HVR1 region or variant HVR2 region can comprise residues corresponding to the amino acid residues found at specific positions within the parental HVR. In this context, "corresponding to" means that an amino acid residue in the variant HVR is the same amino acid residue (i.e., a separate identical residue) present in the parental HVR sequence in the same relative position (i.e., in relation to the remaining amino acids in the parent sequence). By way of example, if a parental HVR sequence comprises a serine residue at position 26, a variant HVR that "comprises a residue corresponding to" residue 26 will also comprise a serine at a position that is relative (i.e., corresponding) to parental position 26.

In particular embodiments, engineered meganucleases of the invention comprise an HVR1 region that has at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 215-270 of SEQ ID NO: 12 or 13.

In certain embodiments, engineered meganucleases of the invention comprise an HVR2 region that has at least 80%, at least 85%, at least 90%, at least 91%, at least 92%, at least 93%, at least 94%, at least 95%, at least 96%, at least 97%, at least 98%, at least 99%, or more sequence identity to an amino acid sequence corresponding to residues 24-79 of SEQ ID NO: 12 or 13.

In other particular embodiments, engineered meganucleases of the invention comprise an HVR1 region that has at least 86% sequence identity to an amino acid sequence corresponding to residues 215-270 of SEQ ID NO: 12 or 13 and an HVR2 region that has at least 97% sequence identity to an amino acid sequence corresponding to residues 24-79 of SEQ ID NO: 12 or 13.

A substantial number of amino acid modifications to the DNA recognition domain of the wild-type I-CreI meganuclease have previously been identified (e.g., U.S. Pat. No. 8,021,867) which, singly or in combination, result in engineered meganucleases with specificities altered at individual bases within the DNA recognition sequence half-site, such that the resulting rationally-designed meganucleases have half-site specificities different from the wild-type enzyme. Table 2 provides potential substitutions that can be made in an engineered meganuclease monomer or subunit to enhance specificity based on the base present at each half-site position (−1 through −9) of a recognition half-site.

TABLE 2

| | Favored Sense-Strand Base | | | | | | | | | |
|---|---|---|---|---|---|---|---|---|---|---|
| Posn. | A | C | G | T | A/T | A/C | A/G | C/T | G/T | A/G/T | A/C/G/T |
| −1 | Y75 | R70* | K70 | Q70* | | | | T46* | | | G70 |
| | L75* | H75* | E70* | C70 | | | | | | | A70 |
| | C75* | R75* | E75* | L70 | | | | | | | S70 |
| | Y139* | H46* | E46* | Y75* | | | | | | | G46* |
| | C46* | K46* | D46* | Q75* | | | | | | | |
| | A46* | R46* | | H75* | | | | | | | |
| | | | | H139 | | | | | | | |
| | | | | Q46* | | | | | | | |
| | | | | H46* | | | | | | | |
| −2 | Q70 | E70 | H70 | Q44* | C44* | | | | | | |
| | T44* | D70 | D44* | | | | | | | | |
| | A44* | K44* | E44* | | | | | | | | |
| | V44* | R44* | | | | | | | | | |
| | I44* | | | | | | | | | | |
| | L44* | | | | | | | | | | |
| | N44* | | | | | | | | | | |
| −3 | Q68 | E68 | R68 | M68 | | H68 | | | Y68 | K68 | |
| | C24* | F68 | | C68 | | | | | | | |

TABLE 2-continued

| | | | | | Favored Sense-Strand Base | | | | | |
|---|---|---|---|---|---|---|---|---|---|---|
| Posn. | A | C | G | T | A/T | A/C | A/G | C/T | G/T | A/G/T | A/C/G/T |
| | I24* | K24* | | L68 | | | | | | | |
| | | R24* | | F68 | | | | | | | |
| −4 | A26* | E77 | R77 | | | | | S77 | | | S26* |
| | Q77 | K26* | E26* | | | | | Q26* | | | |
| −5 | | E42 | R42 | | | | K28* | C28* | | | M66 |
| | | | | | | | | Q42 | | | K66 |
| −6 | Q40 | E40 | R40 | C40 | A40 | | | | | | S40 |
| | C28* | R28* | | I40 | A79 | | | | | | S28* |
| | | | | V40 | A28* | | | | | | |
| | | | | C79 | H28* | | | | | | |
| | | | | I79 | | | | | | | |
| | | | | V79 | | | | | | | |
| | | | | Q28* | | | | | | | |
| −7 | N30* | E38 | K38 | I38 | | | C38 | | | | H38 |
| | Q38 | K30* | R38 | L38 | | | | | | | N38 |
| | | R30* | E30* | | | | | | | | Q30* |
| −8 | F33 | E33 | F33 | L33 | | R32* | R33 | | | | |
| | Y33 | D33 | H33 | V33 | | | | | | | |
| | | | | I33 | | | | | | | |
| | | | | F33 | | | | | | | |
| | | | | C33 | | | | | | | |
| −9 | | E32 | R32 | L32 | | | | | D32 | | S32 |
| | | | K32 | V32 | | | | | I32 | | N32 |
| | | | | A32 | | | | | | | H32 |
| | | | | C32 | | | | | | | Q32 |
| | | | | | | | | | | | T32 |

Bold entries are wild-type contact residues and do not constitute "modifications" as used herein.
An asterisk indicates that the residue contacts the base on the antisense strand.

Although the effects of multiple amino substitutions in the HVR regions are not independent, the data of Table 2 provides possible substitutions in the disclosed HVR regions of SEQ ID NO: 12 and 13 which can be relatively conservative in their effects on specificity. For example, in the HVR1 regions of both SEQ ID NO: 12 and 13, the R residue corresponding to I-CreI position 46, which contacts an A at position −1 of the recognition half-site of SEQ ID NO: 11, could be replaced with C46 or A46 (which have a preference for contacting A), or G46 (which is relatively neutral in preference); the W residue corresponding to I-CreI position 70, which contacts an A at position −1 of the recognition half-site of SEQ ID NO: 11, could be replaced with G70, A70 or S70 (which are relatively neutral in preference); the N residue corresponding to I-CreI position 44, which contacts a C at position −2 of the recognition half-site of SEQ ID NO: 11, could be replaced with K44 or R44 (which have a preference for contacting C); the I residue corresponding to I-CreI position 68, which contacts a G at position −3 of the recognition half-site of SEQ ID NO: 11, could be replaced with R68 (which has a preference for contacting G), or K68 (which has a preference for contacting G or T); the S residue corresponding to I-CreI position 26, which contacts a C at position −4 of the recognition half-site of SEQ ID NO: 11, could be replaced with K26 (which has a preference for contacting A), Q26 (which has a preference for C or T), or S26 (which is relatively neutral in preference); the I residue corresponding to I-CreI position 42, which contacts a C at position −5 of the recognition half-site of SEQ ID NO: 11, could be replaced with E42 (which has a preference for contacting C); the R residue corresponding to I-CreI position 28, which contacts a T at position −6 of the recognition half-site of SEQ ID NO: 11, could be replaced with Q28 (which has a preference for contacting T), or S28 (which is relatively neutral in preference); the E residue corresponding to I-CreI position 40, which contacts a T at position −6 of the recognition half-site of SEQ ID NO: 11, could be replaced with C40, 140 or V40 (which have a preference for T), or A40 (which has a preference for A or T) or S40 (which is relatively neutral in preference); the R residue corresponding to I-CreI position 30, which contacts a T at position-7 of the recognition half-site of SEQ ID NO: 11, could be replaced with Q30 (which is relatively neutral in preference); the A residue corresponding to I-CreI position 33, which contacts a G at position-8 of the recognition half-site of SEQ ID NO: 11, could be replaced with H33 (which has a preference for contacting G), F33 (which has a preference for contacting A, G or T), or R33 (which has a preference for contacting A or G); and the H residue corresponding to I-CreI position 32, which contacts an A at position-9 of the recognition half-site of SEQ ID NO: 11, could be replaced with S32, N32, Q32 or T32 (which are relatively neutral in preference).

Similarly, in the HVR2 regions of both SEQ ID NO: 12 and 13, the G residue corresponding to I-CreI position 46, which contacts a C at position-1 of the recognition half-site of SEQ ID NO: 10, could be replaced with H46, K46 or R46 (which have a preference for contacting C), or T46 (which has a preference for contacting contacts C or T); the N residue corresponding to I-CreI position 70, which contacts a C at position-1 of the recognition half-site of SEQ ID NO: 10, could be replaced with R70, which has a preference for contacting C), or G70, A70 or S70 (which are relatively neutral in preference); the E residue corresponding to I-CreI position 44, which contacts a C at position −2 of the recognition half-site of SEQ ID NO: 10, could be replaced with the similarly negative residue D44 (which has a preference for contacting G) or K44 or R44 (which are positive residues that have a preference for contacting C); the Y residue corresponding to I-CreI position 68, which contacts a T at position −3 of the recognition half-site of SEQ ID NO: 10, could be replaced with M68, C68, L68 or F68 (which have a preference for contacting T), or K68 (which has a preference for contacting G or T); the Q residue corresponding to I-CreI position 26, which contacts an A at position −4 of the recognition half-site of SEQ ID NO: 10, could be replaced with A26 (which has a preference for contacting A) or S26 (which is relatively neutral in preference); the R residue corresponding to I-CreI position 42, which contacts a G at position −5 of the recognition half-site of SEQ ID NO: 10, could be replaced with Q42 (which has a preference for contacting A or G); the A residue corresponding to I-CreI position 28, which contacts a C at position −6 of the recognition half-site of SEQ ID NO: 10, could be replaced with R28 (which has a preference for C), or S28 (which is relatively neutral in preference); the K residue corresponding to I-CreI position 40, which contacts a C at position −6 of the recognition half-site of SEQ ID NO: 10, could be replaced with S40 (which is relatively neutral in preference); the R residue corresponding to I-CreI position 30, which contacts a C at position −7 of the recognition half-site of SEQ ID NO: 10, could be replaced with K30 (which has a preference for contacting C) or Q30 (which is relatively neutral in preference); the F residue corresponding to I-CreI position 33, which contacts a G at position-8 of the recognition half-site of SEQ ID NO: 10, could be replaced with H33 (which has a preference for contacting G) or R33 (which has a preference for contacting A or G); and the S residue corresponding to I-CreI position 32, which contacts a T at position −9 of the recognition half-site of SEQ ID NO: 10, could be replaced with L32, V32, A32, C32 (which have a preference for contacting T), D32 or I32 (which have a preference for contacting C or T) or N32, H32, Q32 or T32 (which are relatively neutral in preference).

These variants can be tested alone and/or in combination to select variants with desired specificity and/or activity using methods described herein and known in the art. Such variants are within the scope of the invention, although the preferred embodiments are disclosed in SEQ ID NO: 12 and 13.

In addition, modifications can be made in an engineered meganuclease monomer or subunit to modulate DNA-binding affinity and/or activity. For example, an engineered meganuclease monomer or subunit described herein can comprise a G, S, or A at a residue corresponding to position 19 of I-CreI or SEQ ID NO: 12 or 13 (WO 2009/001159), a Y, R, K, or D at a residue corresponding to position 66 of I-CreI or SEQ ID NO: 12 or 13, and/or an E, Q, or K at a residue corresponding to position 80 of I-CreI or SEQ ID NO: 12 or 13 (U.S. Pat. No. 8,021,867).

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode a recombinant nuclease of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the variant protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide for its ability to preferentially recognize and cleave the HBV 11-12 recognition sequence within the genome of a Hepatitis B virus.

2.7 Combination Therapy for HBV

In certain embodiments, a method for treating or preventing an HBV infection in a human having or at risk of having the infection is provided, comprising administering to the human a therapeutically effective amount of an engineered meganuclease disclosed herein, or a nucleic acid encoding the same, in combination with a therapeutically effective amount of one or more (e.g., one, two, three, four, one or two, one to three, or one to four) additional therapeutic agents. In one embodiment, a method for treating an HBV infection in a human having or at risk of having the infection is provided, comprising administering to the human a therapeutically effective amount of an engineered meganuclease disclosed herein, or a nucleic acid encoding the same, in combination with a therapeutically effective amount of one or more (e.g., one, two, three, four, one or two, one to three, or one to four) additional therapeutic agents.

In certain embodiments, the present disclosure provides a method for treating an HBV infection, comprising administering to a patient in need thereof a therapeutically effective amount of an engineered meganuclease disclosed herein, or a nucleic acid encoding the same, in combination with a therapeutically effective amount of one or more (e.g., one, two, three, four, one or two, one to three, or one to four) additional therapeutic agents which are suitable for treating an HBV infection.

In certain embodiments, an engineered meganuclease disclosed herein, or a nucleic acid encoding the same, is combined with one, two, three, four, or more additional therapeutic agents. In certain embodiments, an engineered meganuclease disclosed herein, or a nucleic acid encoding the same, is combined with two additional therapeutic agents. In other embodiments, an engineered meganuclease disclosed herein, or a nucleic acid encoding the same, is combined with three additional therapeutic agents. In further embodiments, an engineered meganuclease disclosed herein, or a nucleic acid encoding the same, is combined with four additional therapeutic agents. The one, two, three, four, or more additional therapeutic agents can be different therapeutic agents selected from the same class of therapeutic agents, and/or they can be selected from different classes of therapeutic agents.

Administration of HBV Combination Therapy

In certain embodiments, when an engineered meganuclease disclosed herein, or a nucleic acid encoding the same, is combined with one or more additional therapeutic agents as described above, the components of the composition are administered as a simultaneous or sequential regimen. When administered sequentially, the combination may be administered in two or more administrations.

Co-administration of an engineered meganuclease disclosed herein, or a nucleic acid encoding the same, with one or more additional therapeutic agents generally refers to simultaneous or sequential administration of an engineered meganuclease disclosed herein, or a nucleic acid encoding the same, and one or more additional therapeutic agents, such that therapeutically effective amounts of each agent are present in the body of the patient.

Co-administration includes administration of unit dosages of the compounds disclosed herein before or after administration of unit dosages of one or more additional therapeutic agents. The engineered meganuclease disclosed herein, or a nucleic acid encoding the same, may be administered within seconds, minutes, or hours of the administration of one or more additional therapeutic agents. For example, in some embodiments, a unit dose of an engineered meganuclease disclosed herein, or a nucleic acid encoding the same, is administered first, followed within seconds or minutes by administration of a unit dose of one or more additional therapeutic agents. Alternatively, in other embodiments, a unit dose of one or more additional therapeutic agents is administered first, followed by administration of a unit dose of an engineered meganuclease disclosed herein, or a nucleic acid encoding the same, within seconds or minutes. In some embodiments, a unit dose of a an engineered meganuclease disclosed herein, or a nucleic acid encoding the same, is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of an engineered meganuclease disclosed herein, or a nucleic acid encoding the same.

In certain embodiments, an engineered meganuclease disclosed herein, or a nucleic acid encoding the same, is combined with one or more additional therapeutic agents in a unitary dosage form for simultaneous administration to a patient.

HBV Combination Therapy

The engineered meganucleases disclosed herein, or nucleic acids encoding the same, may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARTs®, Duobodies®, Bites®, XmAbs®, TandAbs®, Fab derivatives), an antibody-drug conjugate (ADC), gene modifiers, cell therapies such as CAR-T (chimeric antigen receptor T-cell), and TCR-T (an engineered T cell receptor) agent or any combination thereof.

In certain embodiments, a formulation comprising an engineered meganuclease described herein, or a nucleic acid encoding the same, may optionally contain one or more other compounds useful for treating HBV. In certain embodiments, the formulation can contain another active ingredient for treating HBV, such as 3-dioxygenase (IDO) inhibitors, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, Endonuclease modulator, epigenetic modifiers, Farnesoid X receptor agonist, HBsAg inhibitors, HBsAg secretion or assembly inhibitors, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, OX-40 receptor agonist, PD-1 inhibitors, PD-L1 inhibitors, Peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, and combinations thereof.

HBV Combination Drugs

Examples of combination drugs for the treatment of HBV include TRUVADA® (tenofovir disoproxil fumarate and emtricitabine); ABX-203, lamivudine, and PEG-IFN-alpha; ABX-203 adefovir, and PEG-IFNalpha; and INO-1800 (INO-9112 and RG7944).

Other HBV Drugs

Examples of other drugs for the treatment of HBV include alpha-hydroxytropolones, amdoxovir, antroquinonol, beta-hydroxycytosine nucleosides, AL-034, CCC-0975, elvucitabine, ezetimibe, cyclosporin A, gentiopicrin (gentiopicroside), JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IB PB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2 (HepTcell), TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, VVX-001, and Lm HBV.

Examples of viral vaccines against HBV antigens include, for example, arena virus vaccines (WO 2017076988).

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), JNJ-440,WF-10,AB-452, ribavirin, IL-12, INO-9112, polymer polyethyleneimine (PEI), Gepon, VGV-1, MOR-22, CRV-431, JNJ-0535, TG-1050, ABI-H2158, BMS-936559,GS-9688, RO-7011785, RG-7854, AB-506, RO-6871765, AIC-649, and IR-103.

Toll-Like Receptor (TLR) Modulators

TLR modulators include modulators of TLR1, TLR2, TLR3, TLR4, TLRS, TLR6, TLR7, TLR8, TLR9, TLR10, TLR11, TLR12, and TLR13. Examples of TLR3 modulators include rintatolimod, poly-ICLC, RIBOXXON®, Apoxxim, RIBOXXIM®, IPH-33, MCT-465, MCT-475, and ND-1.1.

Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, D, telratolimod, SP-0509, TMX-30X, TMX-202, RG-7863, RG-7795, LHC-165, RG-7854, and the compounds disclosed in US20100143301 (Gilead Sciences), US20110098248 (Gilead Sciences), and US20090047249 (Gilead Sciences).

Examples of TLR8 modulators include motolimod, resiquimod, 3M-051, 3M-052, MCT-465, IMO-4200, VTX-763, VTX-1463, GS-9688 and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), US20130251673 (Novira Therapeutics), U.S. Pat. No. 9,670,205, US20160289229, U.S. patent application Ser. No. 15/692,161, and U.S. patent application Ser. No. 15/692,093.

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Examples of TLR7, TLR8 and TLR9 modulators include the compounds disclosed in WO2017047769 (Teika Seiyaku), WO2015014815 (Janssen), WO2018045150(Gilead Sciences Inc), WO2018045144 (Gilead Sciences Inc), WO2015162075(Roche), WO2017034986 (University of Kansas), WO2018095426 (Jiangsu Hengrui Medicine Co Ltd), WO2016091698(Roche), WO2016075661 (GlaxoSmithKline Biologicals), WO2016180743 (Roche), WO2018089695 (Dynavax Technologies), WO2016055553 (Roche), WO2015168279 (Novartis), WO2016107536 (Medshine Discovery), WO2018086593 (Livo (Shanghai) Pharmaceutical), WO2017106607(Merck), WO2017061532 (Sumitomo Dainippon Pharma), WO2016023511 (Chia Tai Tianqing Pharmaceutical), WO2017076346 (Chia Tai Tianqing Pharmaceutical), WO2017046112 (Roche), WO2018078149 (Roche), WO2017040233 (3M Co), WO2016141092 (Gilead Sciences), WO2018049089 (BristolMyers Squibb), WO2015057655 (Eisai Co Ltd), WO2017001307 (Roche), WO2018005586 (BristolMyers Squibb), WO201704023(3M Co), WO2017163264 (Council of Scientific and Industrial Research (India)), WO2018046460 (GlaxoSmithKline Biologicals), WO2018047081 (Novartis), WO2016142250 (Roche), WO2015168269 (Novartis), WO201804163 (Roche), WO2018038877 (3M Co), WO2015057659 (Eisai Co Ltd), WO2017202704 (Roche), WO2018026620 (BristolMyers Squibb), WO2016029077 (Janus Biotherapeutics), WO2018033143 (Merck), WO2016096778 (Roche), WO2017190669 (Shanghai De Novo Pharmatech),U.S. Ser. No. 09/884,866 (University of Minnesota), WO2017219931 (Sichuan KelunBiotech Biopharmaceutical), WO2018002319 (Janssen Sciences), WO2017216054 (Roche), WO2017202703 (Roche), WO2017184735 (IFM Therapeutics), WO2017184746 (IFM Therapeutics), WO2015088045 (Takeda Pharmaceutical), WO2017038909 (Takeda Pharmaceutical), WO2015095780 (University of Kansas), WO2015023958 (University of Kansas).

Interferon Alpha Receptor Ligands

Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include AK-074, HBF-0259, PBHBV-001, PBHBV-2-15, PBHBV-2-1, REP-9AC, REP-9C, REP-9, REP-2139, REP-2139-Ca, REP-2165, REP-2055, REP-2163, REP-2165, REP-2053, REP-2031 and REP-006, and REP-9AC'.

Examples of HBsAg secretion inhibitors include BM601.

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-GS K6-LRx, IONIS-HBV-LRx, GS K-3389404, RG-6004.

Short Interfering RNAs (siRNA) and ddRNAi.

Examples of siRNA include TKM-HBV (TKM-HepB), ALN-HBV, SR-008, HepB-nRNA, and ARC-520, ARC-521, ARB-1740, ARB-1467, DCR-HBVS, RG-6217, ALN-HBV-02, and ARO-HBV.

Examples of DNA-directed RNA interference (ddRNAi) include BB-HB-331.

Endonuclease Modulators

Examples of endonuclease modulators include PGN-514.

Ribonucleotide Reductase Inhibitors

Examples of inhibitors of ribonucleotide reductase include Trimidox.

HBV E Antigen Inhibitors

Examples of HBV E antigen inhibitors include wogonin.

Covalently Closed Circular DNA (cccDNA) Inhibitors

Examples of cccDNA inhibitors include BSBI-25, and CHR-101.

Farnesoid X Receptor Agonist

Example of farnesoid x receptor agonist such as EYP-001, GS-9674, EDP-305, MET-409, Tropifexor, AKN-083, RDX-023, BWD-100, LMB-763, INV-3, NTX-023-1, EP-024297 and GS-8670.

HBV Antibodies

Examples of HBV antibodies targeting the surface antigens of the hepatitis B virus include lenvervimab (GC-1102), XTL-17, XTL-19, KN-003, IV Hepabulin SN, and fully human monoclonal antibody therapy (hepatitis B virus infection, Humabs BioMed).

Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Examples of fully human monoclonal antibodies include HBC-34.

Examples of pMHC-HBV antigens and TCR-like antibodies against pMHC-HBV antigens include those disclosed in Zhu et al. (2017), Mol. Med. Rep. 16(6): 8605-8612; Shen et al. (2017) Sci. Rep. 7(1): 16400; Sastry et al. (2011), J. Virol. 85(5): 1935-1942; Low et al. (2012) PLoS One 7(12): e51397; Cheng et al. (2019) Sci. Immunol. 4(32); and Zhao (2018) Nat. Commun. 9(1): 2716.

CCR2 Chemokine Antagonists

Examples of CCR2 chemokine antagonists include propagermanium.

Thymosin Agonists

Examples of thymosin agonists include Thymalfasin, recombinant thymosin alpha 1 (GeneScience).

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Nucleoprotein Modulators

Nucleoprotein modulators may be either HBV core or capsid protein inhibitors. Examples of nucleoprotein modulators include GS-4882, AB-423, AT-130, GLS4, NVR-1221, NVR-3778, AL-3778, BAY 41-4109, morphothiadine mesilate, ARB-168786, ARB-880, JNJ-379, RG-7907, HEC-72702, AB-506, ABI-H0731, JNJ-440, ABI-H2158 and DVR-23.

Examples of capsid inhibitors include the compounds disclosed in US20140275167 (Novira Therapeutics), US20130251673 (Novira Therapeutics), US20140343032 (Roche), WO2014037480 (Roche), US20130267517

(Roche), WO2014131847 (Janssen), WO2014033176 (Janssen), WO2014033170 (Janssen), WO2014033167 (Janssen), WO2015/059212 (Janssen), WO2015118057(Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744(Roche), US 20170334882(Novira), US 20170334898 (Roche), WO2017202798(Roche), WO2017214395(Enanta), WO2018001944 (Roche), WO2018001952(Roche), WO2018005881(Novira), WO2018005883(Novira), WO2018011100(Roche), WO2018011160(Roche), WO2018011162(Roche), WO2018011163(Roche), WO2018036941(Roche), WO2018043747(Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), US20170121329 (Novira).

Examples of transcript inhibitors include the compounds disclosed in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta). WO2017001853 (Redex Pharma), WO2017211791 (Roche), WO2017216685 (Novartis), WO2017216686 (Novartis), WO2018019297 (Ginkgo Pharma), WO2018022282 (Newave Pharma), US20180030053 (Novartis), WO2018045911 (Zhejiang Pharma).

Retinoic Acid-inducible Gene 1 Stimulators

Examples of stimulators of retinoic acid-inducible gene 1 include SB-9200, SB-40, SB-44, ORI-7246, ORI-9350, ORI-7537, ORI-9020, ORI-9198, and ORI-7170, RGT-100.

NOD2 Stimulators

Examples of stimulators of NOD2 include inarigivir soproxil (SB-9200).

Phosphatidylinositol 3-Kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301,TAK-117, HMPL-689, tenalisib, voxtalisib, and CLR-1401.

Indoleamine-2, 3-Dioxygenase (IDO) Pathway Inhibitors

Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

PD-1 Inhibitors

Examples of PD-1 inhibitors include cemiplimab, nivolumab, pembrolizumab, pidilizumab, BGB-108, STI-A1014, SHR-1210, PDR-001, PF-06801591, IBI-308, GB-226, STI-1110, JNJ-63723283, CA-170, durvalumab, atezolizumab and mDX-400, JS-001, Camrelizumab, Sintilimab, Sintilimab, tislelizumab, BCD-100,BGB-A333 JNJ-63723283, GLS-010 (WBP-3055), CX-072, AGEN-2034, GNS-1480 (Epidermal growth factor receptor antagonist; Programmed cell death ligand 1 inhibitor), CS-1001 M-7824 (PD-L1/TGF-β bifunctional fusion protein), Genolimzumab, BMS-936559.

PD-L1 Inhibitors

Examples of PD-L1 inhibitors include atezolizumab, avelumab, AMP-224, MEDI-0680, RG-7446, GX-P2, durvalumab, KY-1003, KD-033, KN-035, MSB-0010718C, TSR-042, ALN-PDL, STI-A1014,GS-4224, CX-072, and BMS-936559.

Examples of PD-1 inhibitors include the compounds disclosed in WO2017112730 (Incyte Corp), WO2017087777(Incyte Corp), WO2017017624, WO2014151634 (BristolMyers Squibb Co), WO201317322 (BristolMyers Squibb Co), WO2018119286 (Incyte Corp), WO2018119266 (Incyte Corp), WO2018119263(Incyte Corp), WO2018119236 (Incyte Corp), WO2018119221(Incyte Corp), WO2018118848 (BristolMyers Squibb Co), WO20161266460(BristolMyers Squibb Co), WO2017087678 (BristolMyers Squibb Co), WO2016149351 (BristolMyers Squibb Co), WO2015033299 (Aurigene Discovery Technologies Ltd), WO2015179615(Eisai Co Ltd; Eisai Research Institute), WO2017066227(BristolMyers Squibb Co), WO2016142886 (Aurigene Discovery Technologies Ltd), WO2016142852(Aurigene Discovery Technologies Ltd), WO2016142835 (Aurigene Discovery Technologies Ltd; Individual), WO2016142833 (Aurigene Discovery Technologies Ltd), WO2018085750 (BristolMyers Squibb Co), WO2015033303 (Aurigene Discovery Technologies Ltd), WO2017205464 (Incyte Corp), WO2016019232 (3M Co; Individual; Texas A&M University System), WO2015160641 (BristolMyers Squibb Co), WO2017079669 (Incyte Corp), WO2015033301 (Aurigene Discovery Technologies Ltd), WO2015034820 (BristolMyers Squibb Co), WO2018073754 (Aurigene Discovery Technologies Ltd), WO2016077518 (BristolMyers Squibb Co), WO2016057624 (BristolMyers Squibb Co), WO2018044783 (Incyte Corp), WO2016100608 (BristolMyers Squibb Co), WO2016100285 (BristolMyers Squibb Co), WO2016039749 (BristolMyers Squibb Co), WO2015019284 (Cambridge Enterprise Ltd), WO2016142894 (Aurigene Discovery Technologies Ltd), WO2015134605 (BristolMyers Squibb Co), WO2018051255 (Aurigene Discovery Technologies Ltd), WO2018051254 (Aurigene Discovery Technologies Ltd), WO2017222976 (Incyte Corp), WO2017070089 (Incyte Corp), WO2018044963 (BristolMyers Squibb Co), WO2013144704 (Aurigene Discovery Technologies Ltd), WO2018013789 (Incyte Corp), WO2017176608 (BristolMyers Squibb Co), WO2018009505 (BristolMyers Squibb Co), WO2011161699 (Aurigene Discovery Technologies Ltd), WO2015119944 (Incyte Corp; Merck Sharp & Dohme Corp), WO2017192961 (Incyte Corp), WO2017106634 (Incyte Corp), WO2013132317 (Aurigene Discovery Technologies Ltd), WO2012168944 (Aurigene Discovery Technologies Ltd), WO2015036927 (Aurigene Discovery Technologies Ltd), WO2015044900 (Aurigene Discovery Technologies Ltd), WO2018026971 (Arising International).

OX-40 Receptor Agonists

Examples of OX-40 receptor agonists include IBI-101

IAP Inhibitors

Examples of IAP inhibitors include APG-1387

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel).

Examples of KDM1 inhibitors include the compounds disclosed in U.S. Pat. No. 9,186,337B2 (Oryzon Genomics), GSK-2879552, and RG-6016.

STING Agonists

Examples of STING agonists include SB-11285, AdVCA0848, STINGVAX, and compounds disclosed in WO 2018065360 ("Biolog Life Science Institute Forschungslabor and Biochemica-Vertrieb GmbH, Germany), WO 2018009466 (Aduro Biotech), WO 2017186711 (InvivoGen), WO 2017161349 (Immune Sensor), WO 2017106740 (Aduro Biotech), US 20170158724 (Glaxo Smithkiline), WO 2017075477 (Aduro Biotech), US 20170044206 (Merck), WO 2014179760 (University of California), WO2018098203 (Janssn), WO2018118665 (Merck), WO2018118664 (Merck), WO2018100558 (Takeda), WO2018067423 (Merck), WO2018060323 (Boehringer).

Examples of NNRTI include the compounds disclosed in WO2018118826 (Merck), WO2018080903(Merck), WO2018119013 (Merck), WO2017100108 (Idenix), WO2017027434 (Merck), WO2017007701 (Merck), WO2008005555 (Gilead).

HBV Replication Inhibitors

Examples of hepatitis B virus replication inhibitors include isothiafludine, IQP-HBV, RM-5038, and Xingantie.

Arginase Inhibitors

Examples of Arginase inhibitors include CB-1158, C-201, and resminostat.

Gene Therapy and Cell Therapy

Gene therapy and cell therapy include the genetic modification to silence a gene, genetic approaches to directly kill the infected cells, the infusion of immune cells designed to replace most of the patient's own immune system to enhance the immune response to infected cells, or activate the patient's own immune system to kill infected cells, or find and kill the infected cells, and/or genetic approaches to modify cellular activity to further alter endogenous immune responsiveness against the infection.

CAR-T Cell Therapy

A population of immune effector cells engineered to express a chimeric antigen receptor (CAR) can be administered, wherein the CAR comprises an HBV antigen-binding domain. The immune effector cell is a T cell or an NK cell. In some embodiments, the T cell is a CD4+ T cell, a CD8+ T cell, or a combination thereof. Cells can be autologous or allogeneic.

TCR-T Cell Therapy

T cells expressing HBV-specific T cell receptors can be administered. TCR-T cells are engineered to target HBV derived peptides presented on the surface of virus-infected cells.

T-Cells expressing HBV surface antigen (HBsAg)-specific TCR can be administered.

TCR-T therapy directed to treatment of HBV, such as LTCR-H2-1, can be administered.

In another specific embodiment, an engineered meganuclease disclosed herein, or a nucleic acid encoding the same, is combined with an HBV DNA polymerase inhibitor, one or two additional therapeutic agents selected from the group consisting of immunomodulators, TLR modulators, HBsAg inhibitors, HBsAg secretion or assembly inhibitors, HB V therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, an engineered meganuclease disclosed herein, or a nucleic acid encoding the same, is combined with an HBV DNA polymerase inhibitor and at least a second additional therapeutic agent selected from the group consisting of: immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, an engineered meganuclease disclosed herein, or a nucleic acid encoding the same, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

In a particular embodiment, an engineered meganuclease disclosed herein, or a nucleic acid encoding the same, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No.

8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), U.S. Publication No. 2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics),U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057(Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085(Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

In certain embodiments, an engineered meganuclease disclosed herein, or a nucleic acid encoding the same, may be combined with one or more (e.g., one, two, three, four, one or two, one to three, or one to four) additional therapeutic agents in any dosage amount of the engineered meganuclease or nucleic acid.

In certain embodiments, an engineered meganuclease disclosed herein, or a nucleic acid encoding the same, is combined with 5-30 mg tenofovir alafenamide fumarate, tenofovir alafenamide hemifumarate, or tenofovir alafenamide. In certain embodiments, an engineered meganuclease disclosed herein, or a nucleic acid encoding the same, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, an engineered meganuclease disclosed herein, or a nucleic acid encoding the same, is combined with 10 mg tenofovir alafenamide fumarate, tenofovir alafenamide hemifumarate, or tenofovir alafenamide. In certain embodiments, an engineered meganuclease disclosed herein, or a nucleic acid encoding the same, is combined with 25 mg tenofovir alafenamide fumarate, tenofovir alafenamide hemifumarate, or tenofovir alafenamide. An engineered meganuclease disclosed herein, or a nucleic acid encoding the same, may be combined with the agents provided herein in any dosage amount of the compound (e.g., from 50 mg to 500 mg of compound) the same as if each combination of dosages were specifically and individually listed.

In certain embodiments, an engineered meganuclease disclosed herein, or a nucleic acid encoding the same, is combined with 100-400 mg tenofovir disoproxil fumarate, tenofovir disoproxil hemifumarate, or tenofovir disoproxil. In certain embodiments, an engineered meganuclease disclosed herein, or a nucleic acid encoding the same, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, an engineered meganuclease disclosed herein, or a nucleic acid encoding the same, is combined with 300 mg tenofovir disoproxil fumarate, tenofovir disoproxil hemifumarate, or tenofovir disoproxil. In certain embodiments, an engineered meganuclease disclosed herein, or a nucleic acid encoding the same, is combined with 250 mg tenofovir disoproxil fumarate, tenofovir disoproxil hemifumarate, or tenofovir disoproxil. In certain embodiments, an engineered meganuclease disclosed herein, or a nucleic acid encoding the same, is combined with 150 mg tenofovir disoproxil fumarate, tenofovir disoproxil hemifumarate, or tenofovir disoproxil. An engineered meganuclease disclosed herein, or a nucleic acid encoding the same, may be combined with the agents provided herein in any dosage amount of the compound (e.g., from 50 mg to 500 mg of compound) the same as if each combination of dosages were specifically and individually listed.

In one embodiment, kits comprising an engineered meganuclease disclosed herein, or a nucleic acid encoding the same, in combination with one or more (e.g., one, two, three, four, one or two, or one to three, or one to four) additional therapeutic agents are provided.

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Characterization of Meganucleases Having Specificity for the HBV 11-12 Recognition Sequence 1. Meganucleases that Recognize and Cleave the HBV 11-12 Recognition Sequence The second-generation HBV 11-12 meganucleases, referred to as HBV 11-12L.363 (SEQ ID NO: 12) and HBV 11-12L.367 (SEQ ID NO: 13), were engineered to recognize and cleave the HBV 11-12 recognition sequence (SEQ ID NO: 10), which is present in multiple Hepatitis B virus genotypes, including genotypes A-G (SEQ ID NOs: 3-9, respectively). Each of these second-generation meganucleases comprises an N-terminal nuclease-localization signal derived from SV40, a first meganuclease subunit, a linker sequence, and a second meganuclease subunit. A first subunit in each HBV 11-12 meganuclease binds to the HBV11 recognition half-site of SEQ ID NO: 10, while a second subunit binds to the HBV12 recognition half-site (see, FIG. 2). HBV11-binding subunits and HBV12-binding subunits each comprise a 56 base pair hypervariable region, referred to as HVR1 and HVR2, respectively.

The HVR1 region of each HBV11-binding subunit consists of residues 215-270 of SEQ ID NOs: 12 and 13. HBV11-binding subunits of HBV 11-12L.363 and HBV 11-12L.367 are identical to one another outside of the HVR1 region. The HVR1 region of each HBV 11-12 meganuclease comprises modifications relative to the wild-type I-CreI sequence (SEQ ID NO: 1) at positions 215, 217, 219, 221, 223, 224, 229, 231, 233, 235, 237, 239, 241, 259, 261, 263, 264, 266, and 268. The glycine at residue 262 is unmodified in HBV 11-12L.363 and modified to an arginine in HBV 11-12L.367. Although not modified relative to wild-type I-CreI in HBV 11-12L.363, this residue is believed to contribute, in combination with the modified HVR1 residues, to specificity of the nuclease. The HVR1 regions of HBV 11-12L.363 and HBV 11-12L.367 each share 85.71% sequence identity to the HVR1 region of the first-generation HBV 11-12x.26 meganuclease.

The HVR2 region of each HBV12-binding subunit consists of residues 24-79 of SEQ ID NOs: 12 and 13. HBV12-binding subunits of HBV 11-12L.363 and HBV 11-12L.367 are identical to one another outside of the HVR2 region. The HVR2 region of each HBV 11-12 meganuclease comprises modifications relative to the wild-type I-CreI sequence (SEQ ID NO: 1) at positions 24, 26, 28, 30, 33, 38, 40, 42, 44, 46, 68, 70, 75, and 77. Although not modified relative to wild-type I-CreI, the serine residue at position 32 of SEQ ID NOs: 12 and 13 is believed to contribute, in combination with the modified HVR2 residues, to specificity of the nuclease. The HVR2 region of HBV 11-12L.363 and HBV 11-12L.367 each share 96.43% sequence identity to the HVR2 region of the first-generation HBV 11-12x.26 meganuclease.

2. Optimization of First-Generation HBV 11-12 Nucleases

The first-generation HBV 11-12x.26 meganuclease was evaluated for sequence specificity using a method very similar to GUIDE-seq (Tsai et al. (2015), Nat Biotechnology 33:187-197) but adjusted to find potential off-target sites for meganucleases. In general, potential off-target sites were identified by capturing a probe oligonucleotide in the double strand DNA break. The HBV nucleases generate a four base pair 3' overhang so the probe oligo also contains randomized four base pair overhangs to improve ligation efficiency at sites more likely created by the nuclease cleavage. Specificity analysis of HBV 11-12x.26 in HEK 293 cells highlighted a number of positions within the protein-DNA interface that were not discriminating the correct sequence adequately. A library to address all of the problem interfaces would be too large to build and screen in our selection system so, instead, half sites were optimized sequentially. The HBV 11-12 single-chain meganuclease has the monomers fused in an orientation where the HBV12-binding subunit is in the N-terminus and the HBV11-binding subunit is in the C-terminus. Optimization of HBV11 began with re-randomizing amino acids in positions that dictate recognition site specificity. The library was sequentially positively and negatively selected against the intended site and the off-target, HBV11 Off: 5'-TtCCtccCCATACTGCGGAACT-3' (SEQ ID NO: 23). Nucleases were evaluated using an integrated iGFFP assay (as described below) to determine on versus off target cleavage. Four promising nucleases, HBV 11-12L.188, L.190, L.206, and L.271, were re-evaluated in the oligo capture assay. Based on the reduction in read count and number of off-targets, L.188 and L.190 were chosen for subsequent library development. Positions in both the HBV11 and HBV12-binding subunits that contribute to recognition site specificity were randomized in this round of optimization. The libraries were simultaneously positively and negatively selected against the intended target site and either HBV11 Off or HBV12 Off: 5'-TGCCGATCCATACT-GatGAAaa-3' (SEQ ID NO: 24). The off-targets were alternated between successive rounds of selection. A 96-well plate of individual answers (i.e., nucleases) was evaluated for each library in the iGFFP assay (described below) against the intended site and both off-target sites. Two nucleases, HBV 11-12L.363 and L.367, were identified for further testing and were confirmed by full iGFFP testing (described below) that looks at toxicity of the nuclease over a 7 day period. These optimized nucleases were also evaluated for off-target specificity in the oligo capture assay. Finally, identified potential off-targets were verified using PCR amplification of the off-target and next generation sequencing to measure the frequency of indels at the potential off-target site.

3. Evaluation of HBV 11-12 Recognition Sequence Cleavage and Off-Target Cutting

Figure 5:
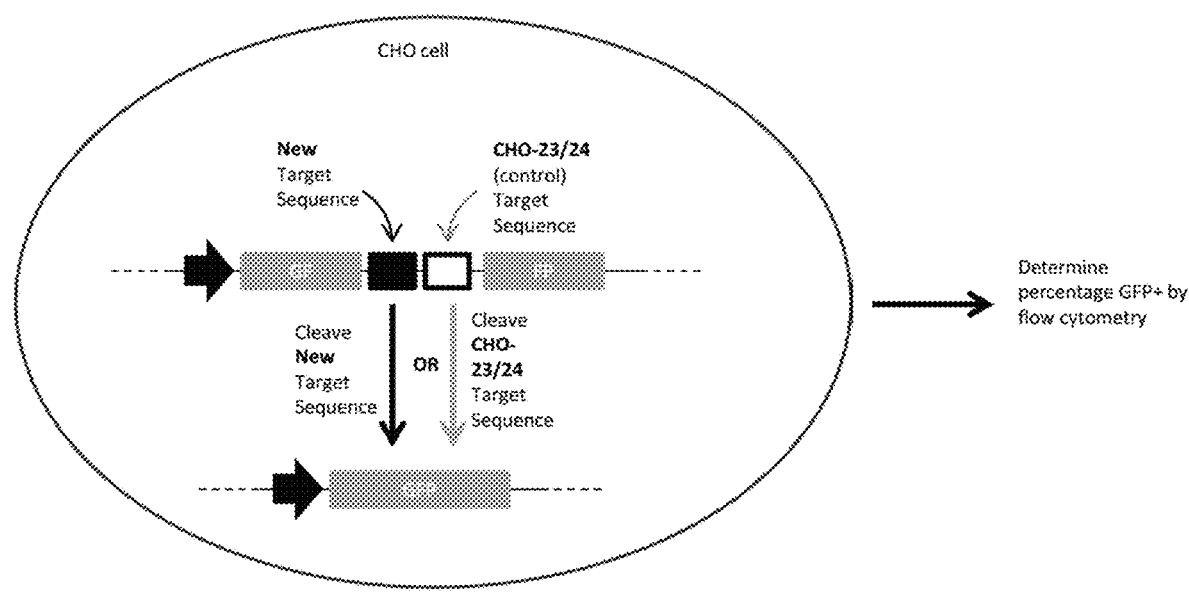
FIG. 5. Schematic of reporter assay in CHO cells for evaluating engineered meganucleases of the invention. A CHO cell line was produced in which a reporter cassette was integrated stably into the genome of the cell. The reporter cassette comprised, in 5' to 3' order: an SV40 Early Promoter; the 5' 2/3 of the GFP gene; the recognition sequence for an engineered meganuclease of the invention (e.g., the HBV 11-12 recognition sequence); the recognition sequence for the CHO 23/24 meganuclease (WO 2012/167192); and the 3' 2/3 of the GFP gene. Cells stably transfected with this cassette did not express GFP in the absence of a DNA break-inducing agent. Meganucleases were introduced by transduction of plasmid DNA or mRNA encoding each meganuclease. When a DNA break was induced at either of the meganuclease recognition sequences, the duplicated regions of the GFP gene recombined with one another to produce a functional GFP gene. The percentage of GFP-expressing cells could then be determined by flow cytometry as an indirect measure of the frequency of genome cleavage by the meganucleases.

To determine whether HBV 11-12 meganucleases could recognize and cleave the HBV 11-12 recognition sequence (SEQ ID NO: 10), each HBV 11-12 meganuclease was evaluated using the CHO cell reporter assay previously described (see WO 2012/167192, FIG. 5). To perform the assay, a pair of CHO cell reporter lines were produced which carried a non-functional Green Fluorescent Protein (GFP) gene expression cassette integrated into the genome of the cell. The GFP gene in each cell line was interrupted by a pair of recognition sequences such that intracellular cleavage of either recognition sequence by a meganuclease would stimulate a homologous recombination event resulting in a functional GFP gene. In both cell lines, one of the recognition sequences was derived from the HBV 11-12 target and the second recognition sequence was specifically recognized by a control meganuclease called "CHO 23/24". CHO reporter cells comprising the HBV 11-12 recognition sequence (SEQ ID NO: 10) and the CHO 23/24 recognition sequence are referred to herein as "HBV 11-12 cells."

Figure 6:
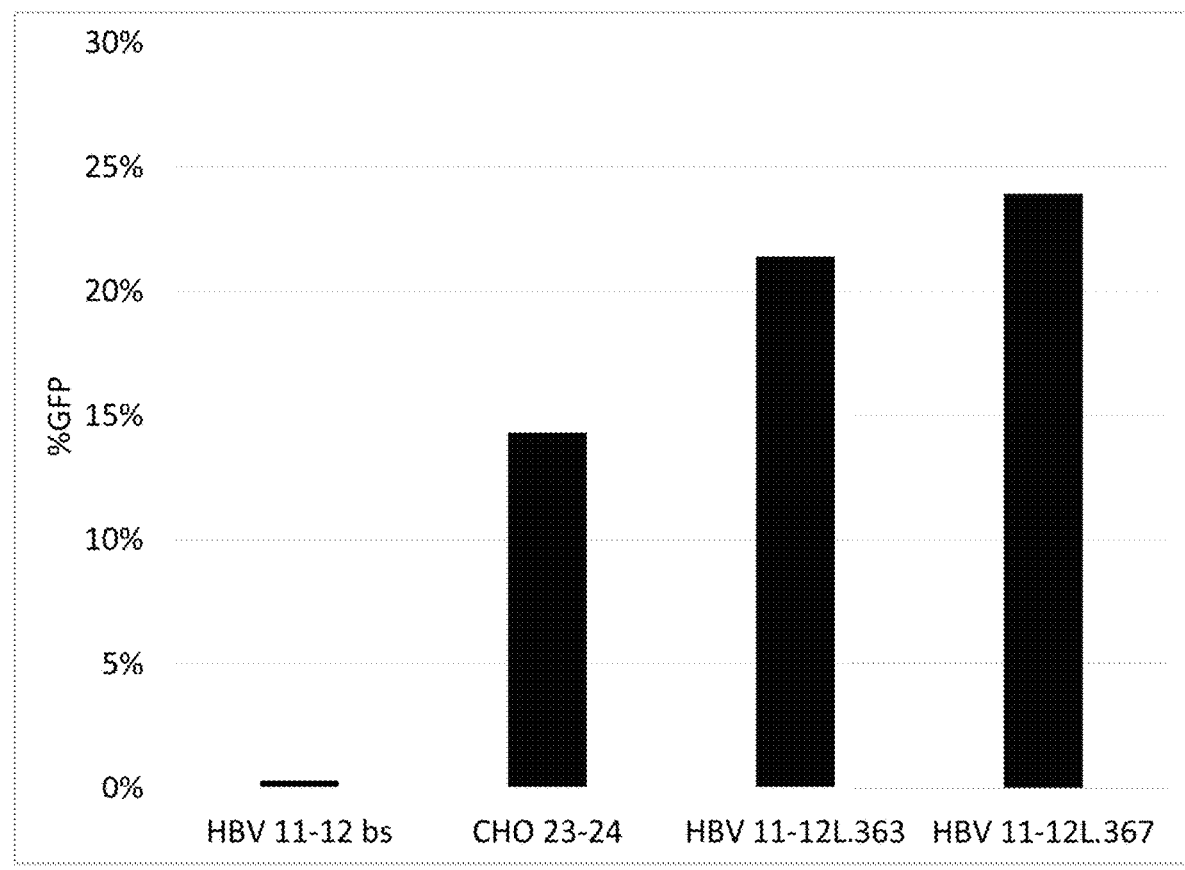
FIG. 6. Efficiency of engineered meganucleases for recognizing and cleaving the HBV 11-12 recognition sequence in a CHO cell reporter assay. The HBV 11-12L.363 and HBV 11-12L.367 meganucleases, set forth in SEQ ID NOs: 12 and 13, respectively, were engineered to target the HBV 11-12 recognition sequence (SEQ ID NO: 10), and were screened for efficacy in the CHO cell reporter assay. The results shown provide the percentage of GFP-expressing cells observed, which indicates the efficacy of each meganuclease for cleaving the target recognition sequence or the CHO 23/24 recognition sequence. A negative control (bs) was further included in the assay.

HBV 11-12 cells were transfected with plasmid DNA encoding HBV 11-12L.363 or HBV 11-12L.367, or encoding the CHO 23/24 meganuclease. $4 \times 10^5$ CHO cells were transfected with 50 ng of plasmid DNA in a 96-well plate using Lipofectamine 2000 (ThermoFisher) according to the manufacturer's instructions. At 48 hours post-transfection, cells were evaluated by flow cytometry to determine the percentage of GFP-positive cells compared to an untransfected negative control (1-2 bs). Both HBV 11-12 meganucleases were found to produce GFP-positive cells in cell lines comprising the HBV 11-12 recognition sequence at frequencies significantly exceeding the negative control and exceeding the CHO 23/24 positive control, indicating that each HBV 11-12 meganuclease was able to efficiently recognize and cleave the intended HBV 11-12 recognition sequence in a cell (see, FIG. 6).

Figure 7:
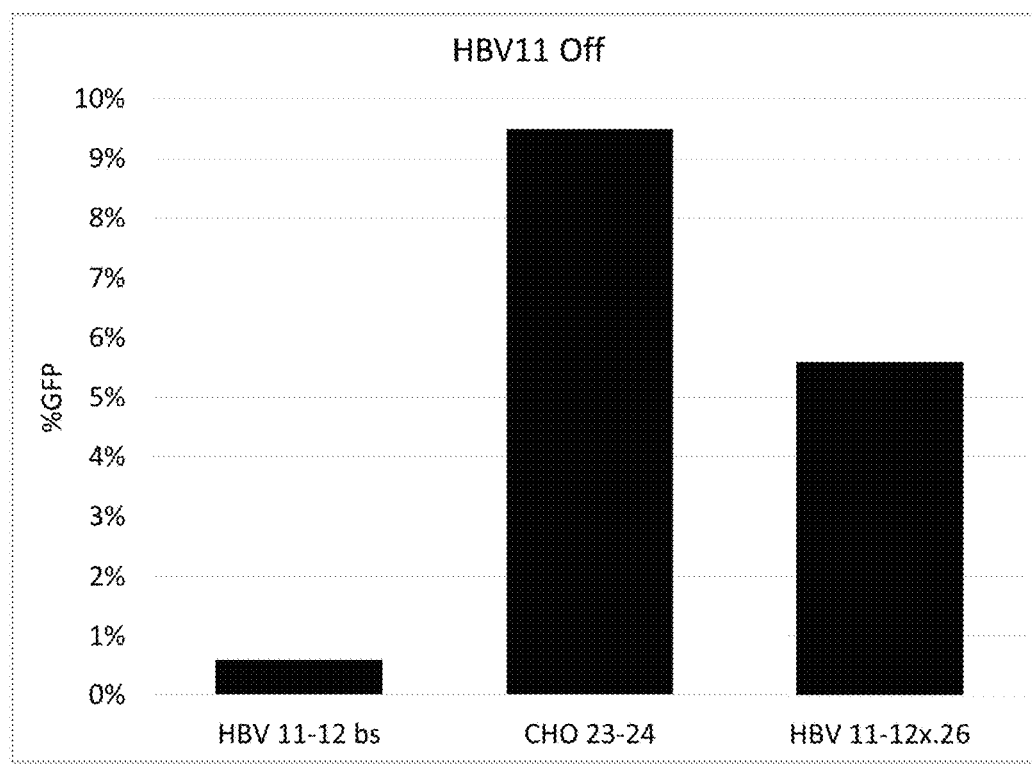
FIG. 7. Efficiency of engineered meganucleases for recognizing and cleaving the HBV11 off-target (HBV11 Off) recognition sequence in a CHO cell reporter assay. Plasmids encoding the HBV 11-12 meganucleases of the invention were transfected into "HBV11 Off" cells which contain the counter selected HBV11 Off recognition sequence (SEQ ID NO: 23) between the GFP direct repeats, as well as a CHO 23-24 recognition sequence. A) Cleavage of the HBV11 Off recognition sequence by the first-generation HBV 11-12×.26 meganuclease. B) Cleavage of the HBV11 Off recognition sequence by the second-generation HBV11-12L.363 and HBV 11-12L.367 meganucleases.
Figure 7:
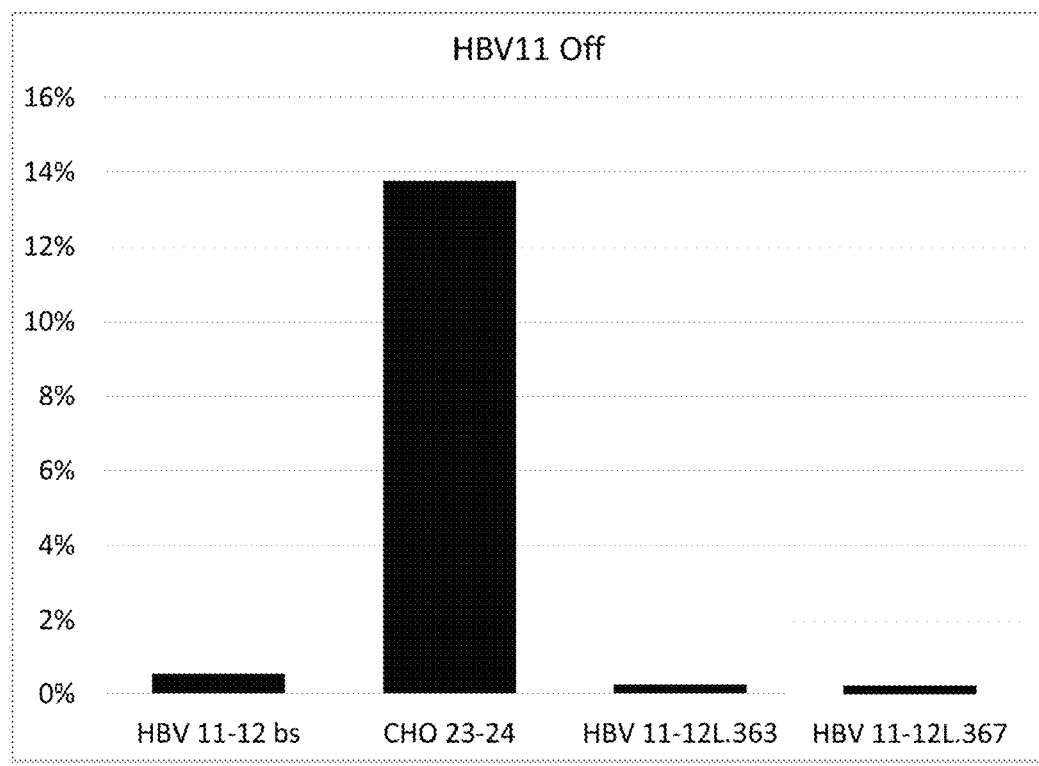
Figure 8:
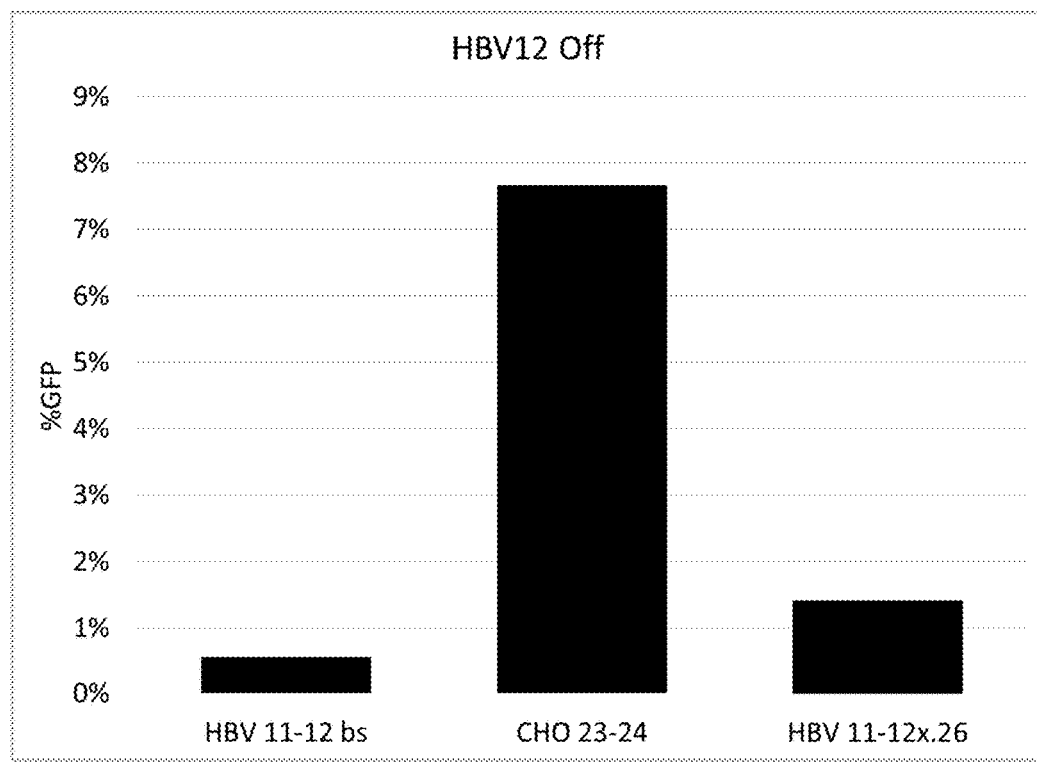
FIG. 8. Efficiency of engineered meganucleases for recognizing and cleaving the HBV12 off-target (HBV12 Off) recognition sequence in a CHO cell reporter assay. Plasmids encoding The HBV 11-12 meganucleases of the invention were transfected into "HBV12 Off" cells which contain the counter selected HBV12 Off recognition sequence (SEQ ID NO: 24) between the GFP direct repeats, as well as a CHO 23-24 recognition sequence. A) Cleavage of the HBV12 Off recognition sequence by the first-generation HBV 11-12×.26 meganuclease. B) Cleavage of the HBV12 Off recognition sequence by the second-generation HBV11-12L.363 and HBV 11-12L.367 meganucleases.
Figure 8:
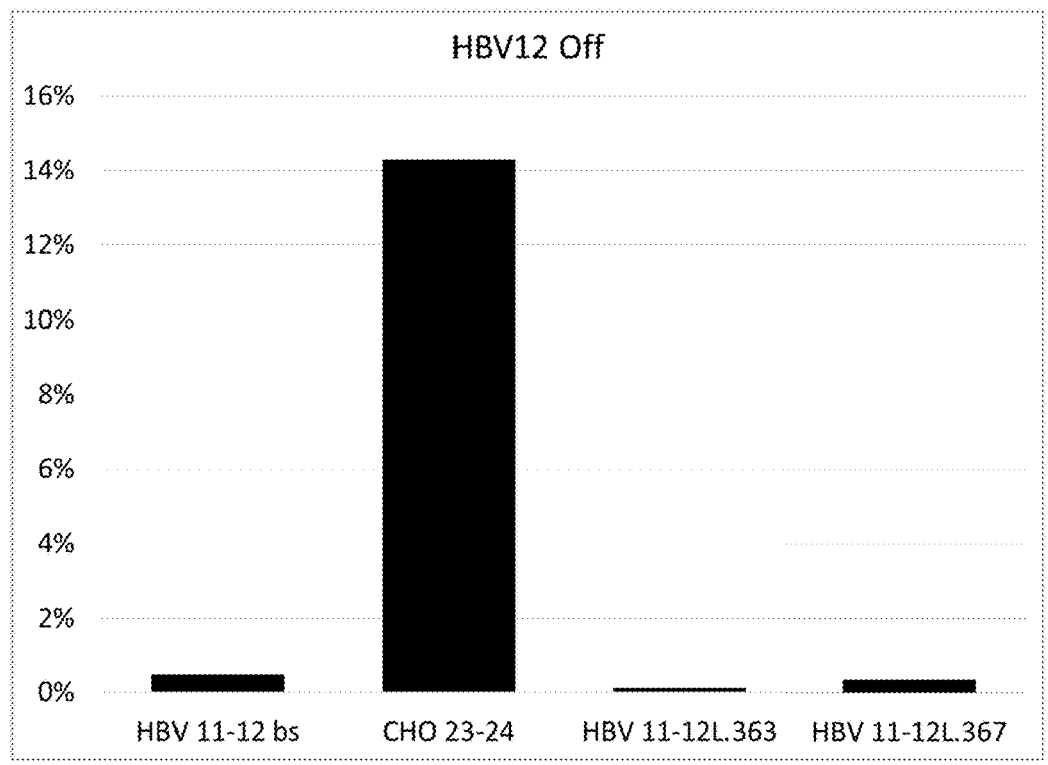

Alternatively, the HBV 11-12 meganucleases were also transfected into "HBV11 Off" or "HBV12 Off" cells which contain one of the counter selected off-target sequences between the GFP direct repeats. Unlike the intended target site in HBV 11-12 CHO cells, a desirable nuclease in HBV11 Off or HBV12 Off CHO cells has only background level GFP positive cells because it is able to discriminate against cutting the off-target sequence. The CHO 23-24 target site acts as a positive control in these experiments, demonstrating that the GFP can still be produced if the target site is cut by the CHO 23-24 nuclease. The new nucleases demonstrated a significantly improved (i.e., increased) discrimination against the HBV11 Off (FIG. 7) and HBV12 Off (FIG. 8) recognition sequences compared to the first-generation HBV 11-12x.26 meganuclease.

Figure 9:
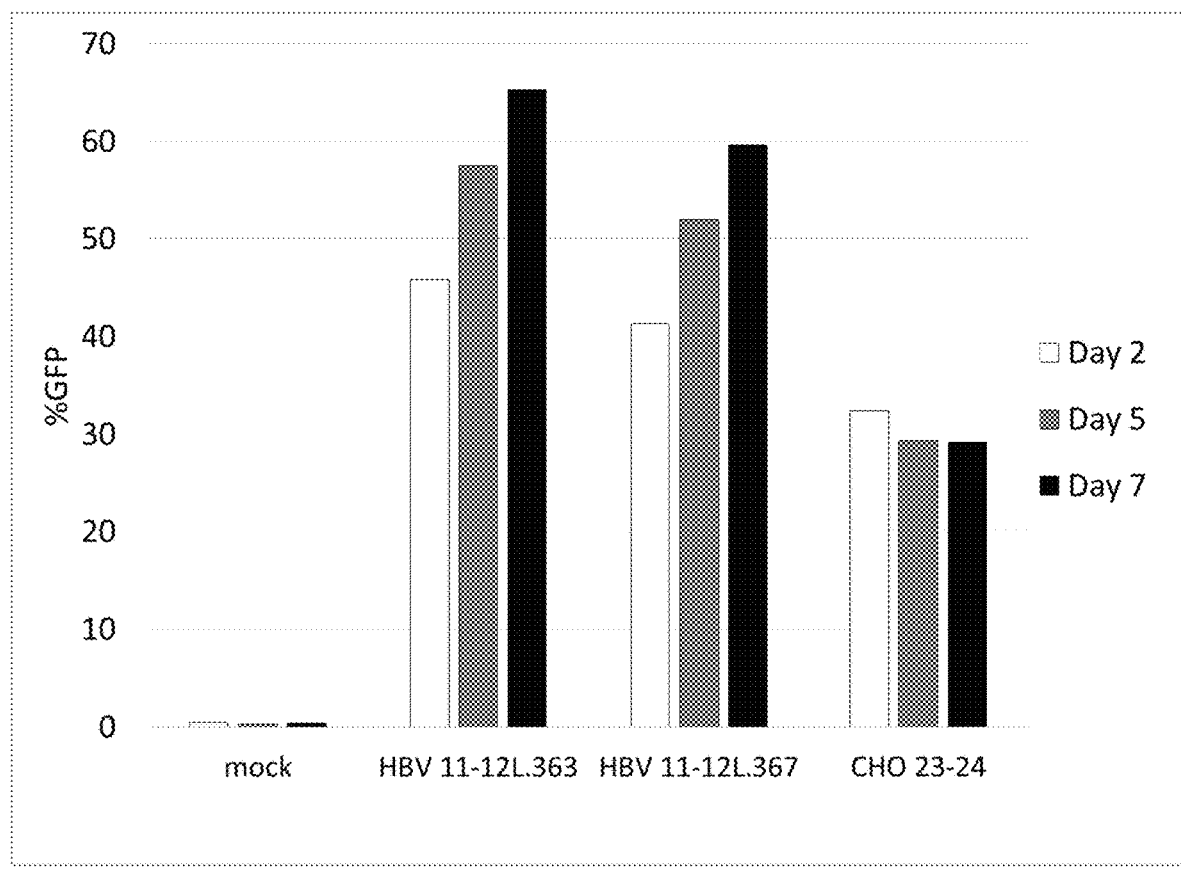
FIG. 9. Efficiency of engineered meganucleases for recognizing and cleaving the HBV 11-12 recognition sequence in a CHO cell reporter assay. The HBV 11-12L.363 and HBV 11-12L.367 meganucleases, set forth in SEQ ID NOs: 12 and 13, respectively, were screened for efficacy in the CHO cell reporter assay at 2, 5, and 7 days after nucleofection in order to determine toxicity associated with expression of the meganuclease. The results shown provide the percentage of GFP-expressing cells observed over the 7 day period of analysis, which indicates the efficacy of each meganuclease for cleaving a target recognition sequence or the CHO 23/24 recognition sequence as a function of time.

The efficacy of HBV 11-12L.363 and L.367 meganucleases was also determined in a time-dependent manner 2, 5, and 7 days after introduction of the meganucleases into HBV 11-12 cells. In this study, HBV 11-12 cells ($1.0 \times 10^6$) were electroporated with $1 \times 10^6$ copies of meganuclease mRNA per cell using a BioRad Gene Pulser Xcell according to the manufacturer's instructions. At 48 hours post-transfection, cells were evaluated by flow cytometry to determine the percentage of GFP-positive cells. A CHO 23/24 meganuclease was also included at each time point as a positive control. Each of the meganucleases showed a superior GFP-positive percentage relative to CHO 23-24 and the percent GFP continued to increase over the course of the experiment, indicating no gross toxicity to the cells (FIG. 9).

Figure 10:
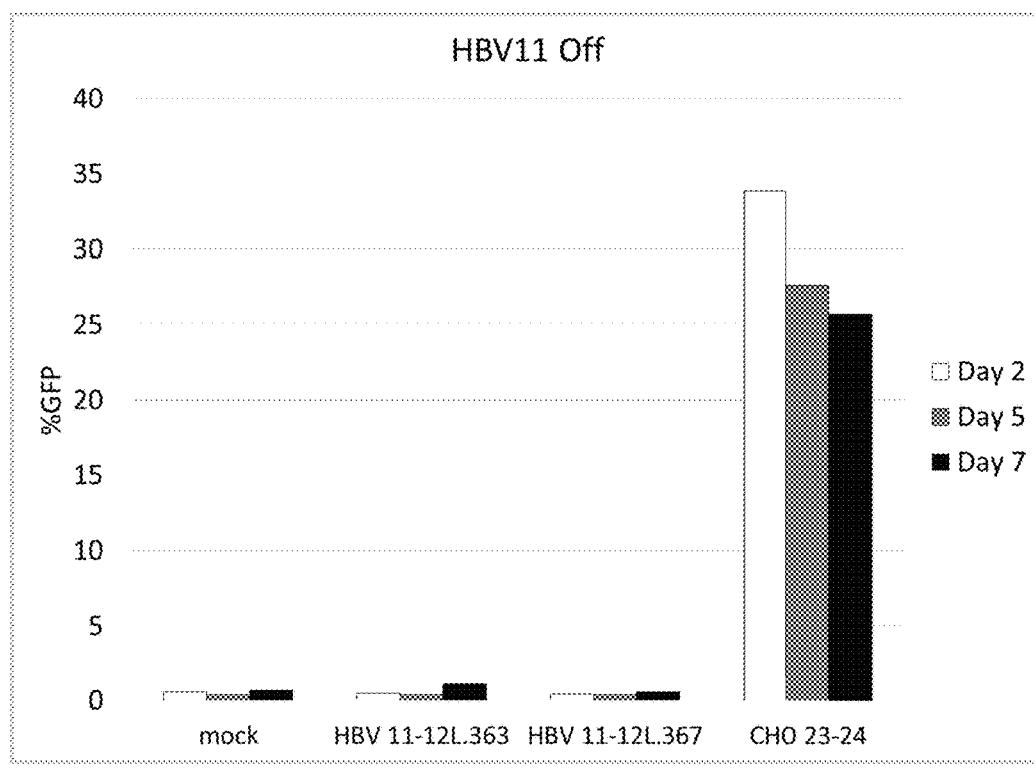
FIG. 10. Efficiency of engineered meganucleases for recognizing and cleaving the HBV11 Off and HBV12 Off recognition sequences in a CHO cell reporter assay. mRNA encoding the HBV 11-12 meganucleases of the invention were transfected into HBV11 Off cells or HBV12 Off cells and were screened for efficacy in the CHO cell reporter assay at 2, 5, and 7 days after nucleofection in order to determine toxicity. The results shown provide the percentage of GFP-expressing cells observed over the 7 day period of analysis. A) Cleavage of the HBV11 Off recognition sequence by the HBV 11-12L.363 and HBV 11-12L.367 meganucleases. B) Cleavage of the HBV12 Off recognition sequence by the HBV11-12L.363 and HBV 11-12L.367 meganucleases.
Figure 10:
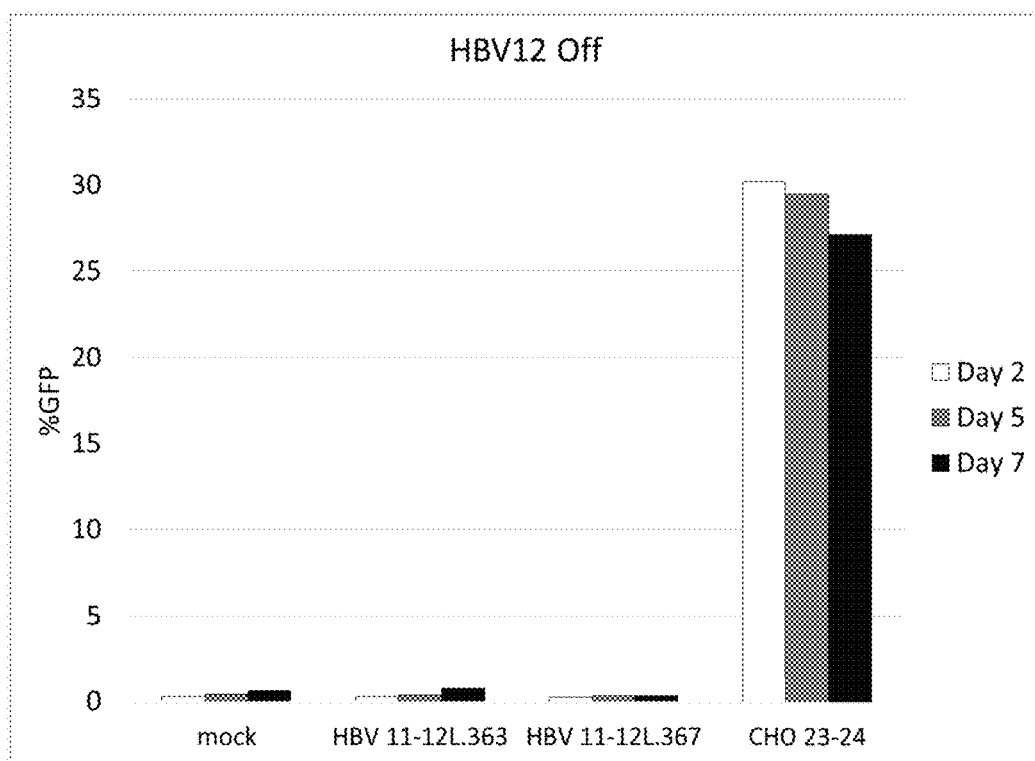

The extended iGFFP assay was also used to evaluate the same group of meganucleases for discrimination against the two off targets, HBV11 Off and HBV12 Off, over a 7 day period. In this case, cells containing either HBV11 Off or HBV12 Off, and CHO 23-24, were electroporated with $1 \times 10^6$ copies of meganuclease mRNA per cell using a BioRad Gene Pulser Xcell according to the manufacturer's instructions. At 2, 5, and 7 days post-transfection, cells were evaluated by flow cytometry to determine the percentage of GFP-positive cells. A CHO 23/24 meganuclease was also included at each time point as a positive control. Each of the nucleases showed excellent discrimination against both off-targets over the period observed (FIGS. 10A and 10B).

4. Oligo Capture Assay and Analysis of Off-Target Cutting

In these studies, an oligo capture assay was used to identify off target cutting induced by the first-generation HBV 11-12x.26 meganuclease and the optimized meganucleases HBV 11-12L.188, HBV 11-12L.363, and HBV 11-12L.367. Off target cutting was first assessed in HepG2 cells which lack the HBV 11-12 recognition sequence in their genome. Off target cutting was then assessed in a lentivirus-modified HepG2 cell line that comprises in its genome a partial HBV genome comprising the HBV 11-12 recognition sequence.

Similar to GUIDE-seq, the oligo capture assay identifies potential off-target sites produced by the HBV 11-12 meganucleases by capturing an oligonucleotide at break sites within the cell's genomic DNA. GUIDE-seq was developed for CRISPR-Cas9 generated DNA breaks and there are a few key modifications to the chemistry and analysis in order to apply this technique to the present nucleases. Unlike CRISPR-cas9, the engineered meganucleases of the invention generate a four base pair 3' overhang. To accommodate for this difference, the oligonucleotides used in oligo capture have randomized four base pair overhangs that could be compatible with the overhangs generated with the HBV 11-12 meganuclease. A higher frequency of insertion is observed due to the greater efficiency of ligating sticky ends rather than blunt ends. Cells were transfected with mRNA encoding the nuclease and the double stranded DNA oligonucleotides. After two days, the genomic DNA from these cells was isolated and sonicated to shear the DNA to smaller sizes. An oligonucleotide adapter was ligated to the sheared DNA and PCR was used to amplify any DNA pieces that contain an adapter at one end and the captured oligonucleotide at the other end. The amplified DNA was purified and sequencing libraries were prepared using standard commercial kits.

Sequencing libraries were run on an Illumina MiSeq using V2 $2 \times 150$ kits. The data was filtered and analyzed for valid sites that captured an oligonucleotide and a potential off-target site is predicted. Here again, the protocol needed to be adjusted from the PAM search used for CRISPR-cas9 to the HBV 11-12 meganuclease search. The software developed checks each sequence to make sure there is adapter and captured oligo flanking the sequence to verify that it is a valid read. The software also checks for PCR duplicates and removes reads that are identical to help reduce PCR bias. The sequence reads are aligned to a reference genome and grouped sequences within thousand base pair windows are scanned for a potential HBV 11-12 meganuclease site.

Each HBV 11-12 meganuclease is a linked dimer. Each monomer recognizes a nine base pair half site with a four base pair spacer in the center between the two half sites. The software looks for the closest sequence match for each half site with no allowed gaps. The middle four base pairs are not considered in the off-target selection because the HBV 11-12 meganucleases can generally tolerate a higher amount of degeneracy at these positions in the target site. The software outputs a list of potential off-target sites with the number of base mismatches in the combined half sites but not counting the middle four base pair mismatches. The software does not eliminate any off-targets based on an arbitrary mismatch filter, unlike CRISPR-Cas9 which eliminates any off-target identified with more than six base pairs mismatched. Instead, background noise generated from random capture of the oligo at fragile spots or hot spots within the genome can be reduced in two ways. First, an untreated mock sample is also run though oligo capture and windows of integration sites without the nuclease present can be subtracted from the nuclease containing samples. We have also found that running the assay in triplicate and eliminating any sites that do not repeat in at least two of the three repeats is a good way to empirically remove random integration noise.

Figure 11:
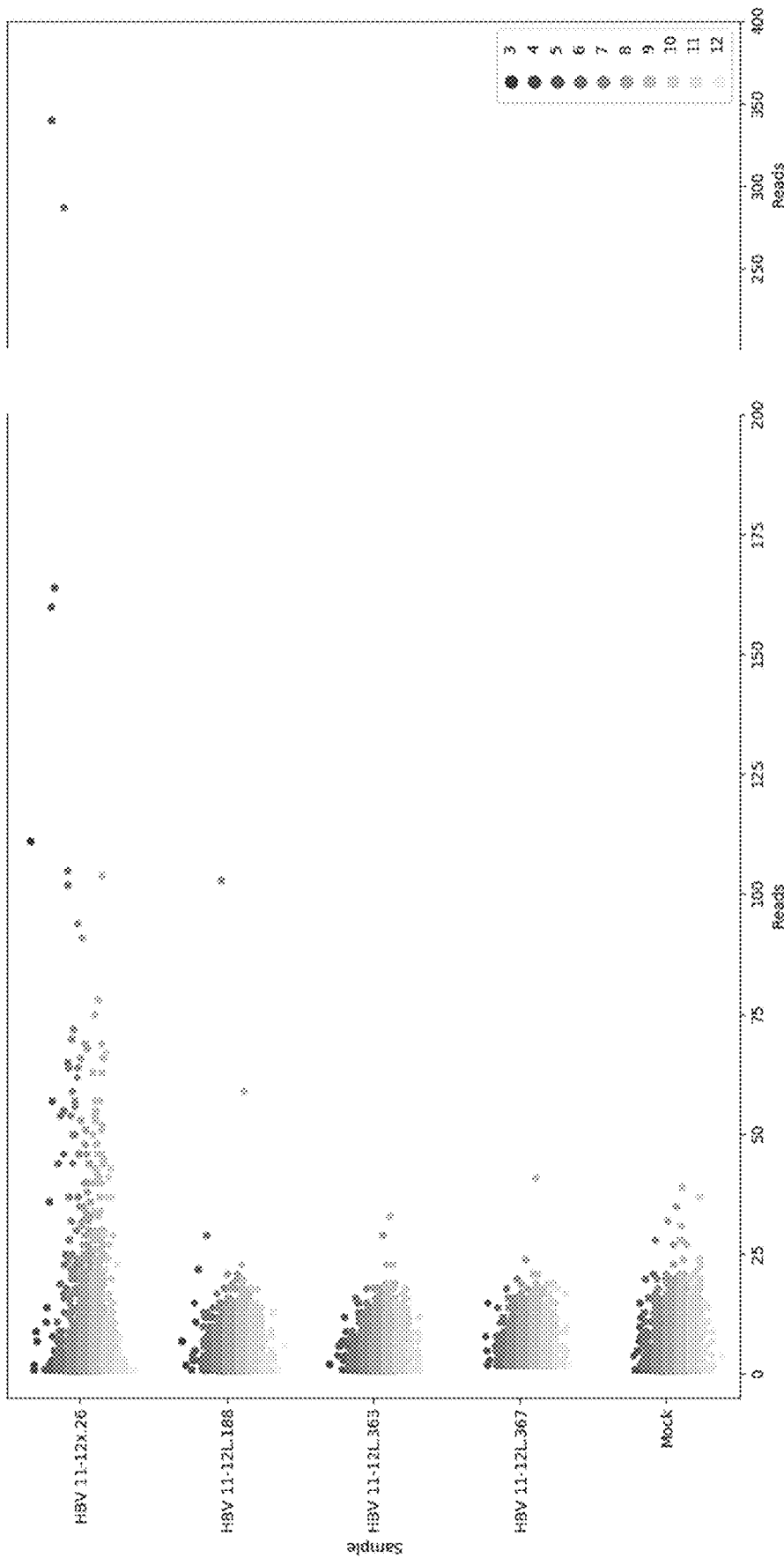
FIG. 11. Oligo capture assay in a HepG2 cell line lacking the HBV 11-12 recognition sequence. Oligo capture data is shown for HBV 11-12×.26, HBV 11-12L.188, HBV 11-12L.363, and HBV 11-12L.367. Data is graphically visualized wherein off target sites are plotted according to their number of aligned reads on the X axis, and the number of mismatched base pairs compared to the intended site are indicated by color, with darker colors indicating closer overall matches between off-targets and the intended binding site.

Although read count does not directly correlate with cutting frequency at a particular site, it can generally highlight off-targets that are potentially more concerning or more valid because they occur more often. One way to graphically visualize the oligo capture data as a measure of number of potentially valid off-target sites is shown in FIG. 11. Each off-target generated by a particular nuclease is plotted based on the number of unique sequence reads aligned at that site. The number of base pair mismatches between the putative off-target site and the intended site are indicated by color scale with darker colors indicating sites that are more similar to the intended target site. For a nuclease with high-specificity, the intended site should have the highest read count. Better nucleases remove both the higher count sites (to the right of the graph) and the sites with high similarity (darker colored points).

In FIG. 11, which was generated in the HepG2 cell line lacking the HBV 11-12 recognition sequence, each of the optimized meganucleases lacked the higher read count off-targets and reduced the number of high similarity off-targets observed for the first-generation HBV 11-12x.26 meganuclease. The HBV 11-12L.363 and HBV 11-12L.367 meganucleases, exhibited further improvements over the earlier generation HBV 11-12L.118 meganuclease. However, because oligo capture provides a relative activity of a nuclease to target sites within a sample, it is difficult to determine the extent to which these off-targets are cut without an on-target intended site for comparison.

Figure 12:
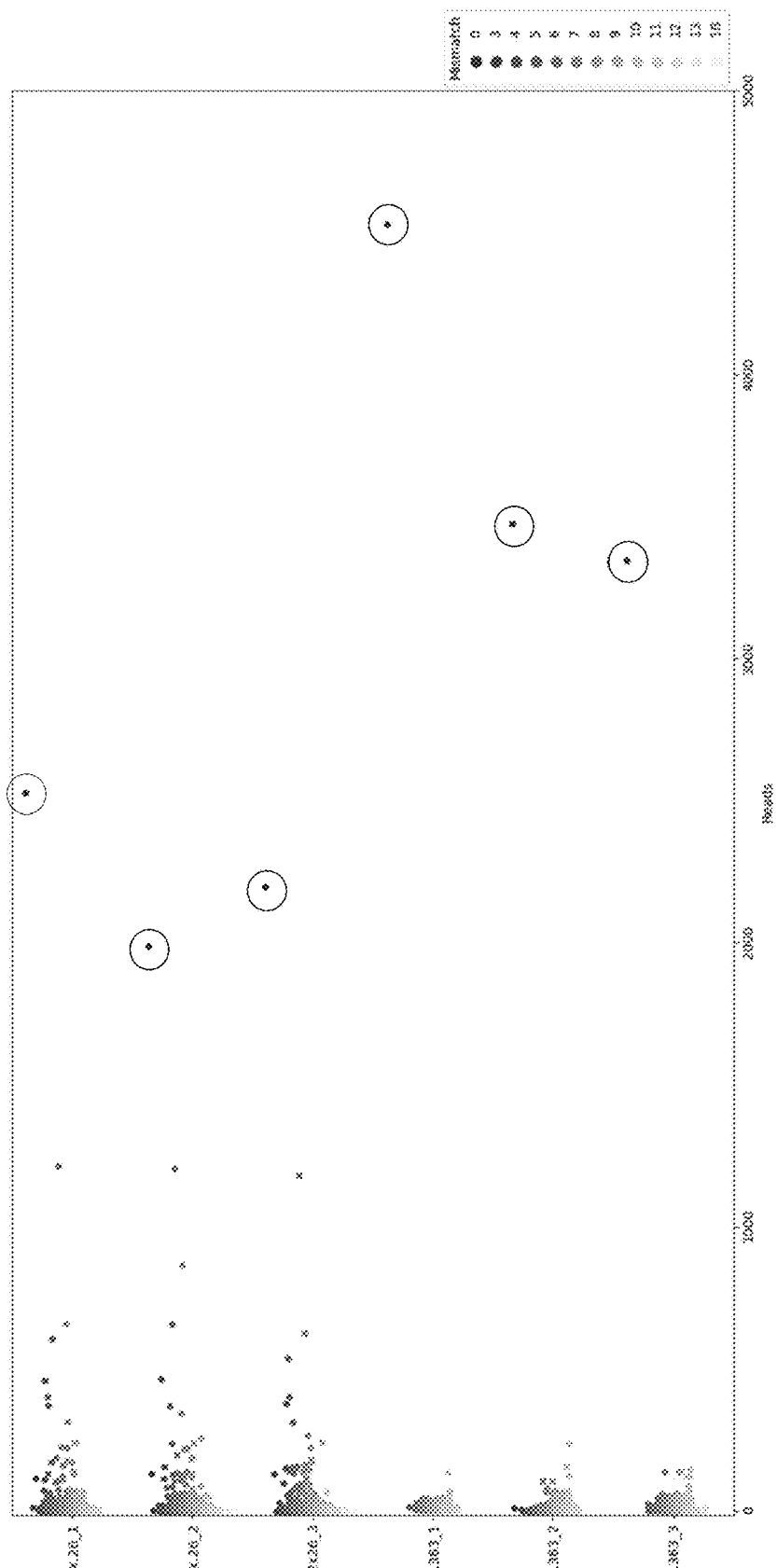
FIG. 12. Oligo capture assay in a HepG2 HepB cell line, which comprises a partial HBV genome including the HBV 11-12 recognition sequence. Oligo capture data of HBV 11-12×.26 and HBV 11-12L.363 are graphically visualized wherein off target sites are plotted according to their number of aligned reads on the X axis, and the number of mismatched base pairs compared to the intended site are indicated by color, with darker colors indicating closer overall matches between off-targets and the intended binding site. Intended target sites are indicated by circles.

In FIG. 12, HBV 11-12×.26 and HBV 11-12L.363 were compared in the HepG2 HepB cell line, which comprises a partial HBV genome including the HBV 11-12 recognition sequence. While the number of reads aligned at the intended site cannot be compared between samples as a measure of total activity at the intended site, the distance between the points indicating the intended site (circled) and the points indicating off-target sites can be compared. The far larger distance between the intended site and the off-target sites for HBV 11-12L.363 than that of HBV 11-12×.26 indicates a large increase in the specificity of the enzyme and a large decrease in cleavage of off-target sites both in number of sites and percentage cleaved.

In summary, the optimized meganucleases, and particularly HBV 11-12L.363 and HBV 11-12L.367, showed clear superiority in specificity over the parental HBV 11-12×.26 as determined by oligo capture. All three optimized enzymes showed a significant reduction in both highly similar, less frequently cleaved sites, and less similar, more frequently cut sites. Further analysis of HBV 11-12L.363 demonstrated a large increase in the ratio of cleavage activity at the intended site to cleavage activity at off-target sites compared to HBV 11-12×.26.

Example 2

Generation of Indels at Recognition Sequence In Vitro

Studies were conducted to evaluate the efficacy of HBV 11-12 meganucleases for causing insertions and/or deletions ("indels") at their intended recognition sequence (i.e., the HBV 11-12 recognition sequence). Indel formation was detected in these experiments by either a T7 endonuclease I (T7E) digest or digital PCR analysis.

In these experiments, a HepG2 cell line (HepG2 HepB) was generated by Precision BioSciences to stably express one copy (as determined by digital PCR) of a ~1500 bp region of the Hepatitis B genome including the HBV 11-12 meganuclease target site. HepG2 HepB (5×10$^5$) cells were transfected with mRNA (1 µg) encoding HBV 11-12L.26, HBV 11-12L.188, HBV 11-12L.363, HBV 11-12L.367, and HBV 11-12×.26, respectively, using the ThermoFisher Neon Transfection System according to the manufacturer's protocol. At two days post-transfection, genomic DNA was isolated from cells for analysis of indel formation by T7E and digital PCR. Genomic DNA from mock transfected HepG2 HepB cells was used as a control.

For T7E analysis, genomic DNA was PCR amplified using P1 and P2 primers:

```
P1:
                                            (SEQ ID NO: 25)
[5'-gccattttctataagtgttaacttccgctcctc-3']

P2:
                                            (SEQ ID NO: 26)
[5'-cgtgcagtcactatggatcaactacttagatg-3']
```

Amplification was confirmed by visualization of a ~1650 bp band on an agarose gel. PCR-amplified DNA was denatured and slowly rehybridized to allow formation of heteroduplex DNA sequences and then digested with T7 endonuclease I. Digestion products were visualized on an agarose gel.

Figure 13:
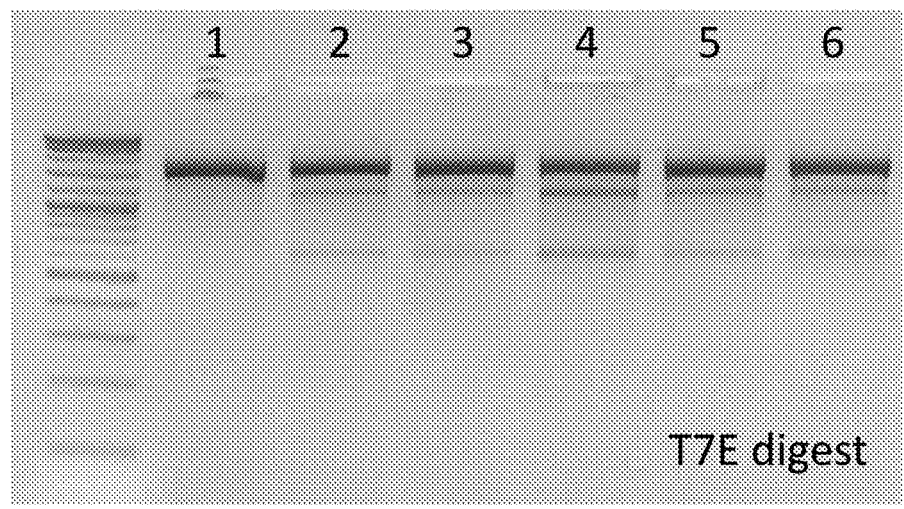
FIG. 13. Efficiency of indel formation detected by T7E assay. A HepG2 cell line (HepG2 HepB) was generated that stably expressed one copy of a ~1500 bp region of the Hepatitis B genome including the HBV 11-12 meganuclease target site. HepG2 HepB cells were transfected with mRNA encoding HBV 11-12L.26, HBV 11-12L.188, HBV 11-12L.363, HBV 11-12L.367, or HBV 11-12×.26, respectively. At two days post-transfection, genomic DNA was isolated from cells for analysis of indel formation by T7E assay. Genomic DNA from mock transfected HepG2 HepB cells was used as a control. Amplification was confirmed by visualization of a ~1650 bp band on an agarose gel. PCR-amplified DNA was denatured and slowly rehybridized to allow formation of heteroduplex DNA sequences and then digested with T7 endonuclease I. Digestion products were visualized on an agarose gel.

While mock-transfected cells yielded a single band at ~1650 bp, transfection with HBV 11-12L.26, HBV 11-12L.188, HBV 11-12L.363, HBV 11-12L.367 and HBV 11-12×.26, respectively, yielded two lower molecular weight bands at ~600 bp and ~1050 bp after T7E digestion, indicating successful gene editing (FIG. 13). Surprisingly, the increased intensity of the lower bands in HBV 11-12L.363 compared to the first-generation HBV 11-12×.26 indicates that a higher efficiency of gene editing at the target site was achieved.

Digital PCR was performed using the QX200 droplet digital PCR system to quantify indel formation in HepG2 HepB cells after meganuclease transfection. A FAM-tagged TaqMan probe (T1) was designed to recognize the HBV 11-12 meganuclease target site, as well as a HEX-tagged TaqMan probe (T2) that binds genomic sequence ~100 bp downstream of the target site, intended to serve as a reference probe. The probes were multiplexed for genomic DNA amplification using primers P3 and P4. Droplets were gated by fluorescence amplitude to indicate double-positive, double-negative, and single-positive populations. Indels were calculated as the number of HEX-positive droplets divided by the number of double-positive (FAM+/HEX+) droplets.

```
P3:
                                            (SEQ ID NO: 27)
[5'-ggtctgtgccaagtgtttg-3']

P4:
                                            (SEQ ID NO: 28)
[5'-gtagacaaaggacgttccg-3']

T1:
                                            (SEQ ID NO: 29)
[5'-tgccgatccatactgcggaact-3']

T2:
                                            (SEQ ID NO: 30)
[5'-cacagcctagcagccatggaaac-3']
```

Figure 14:
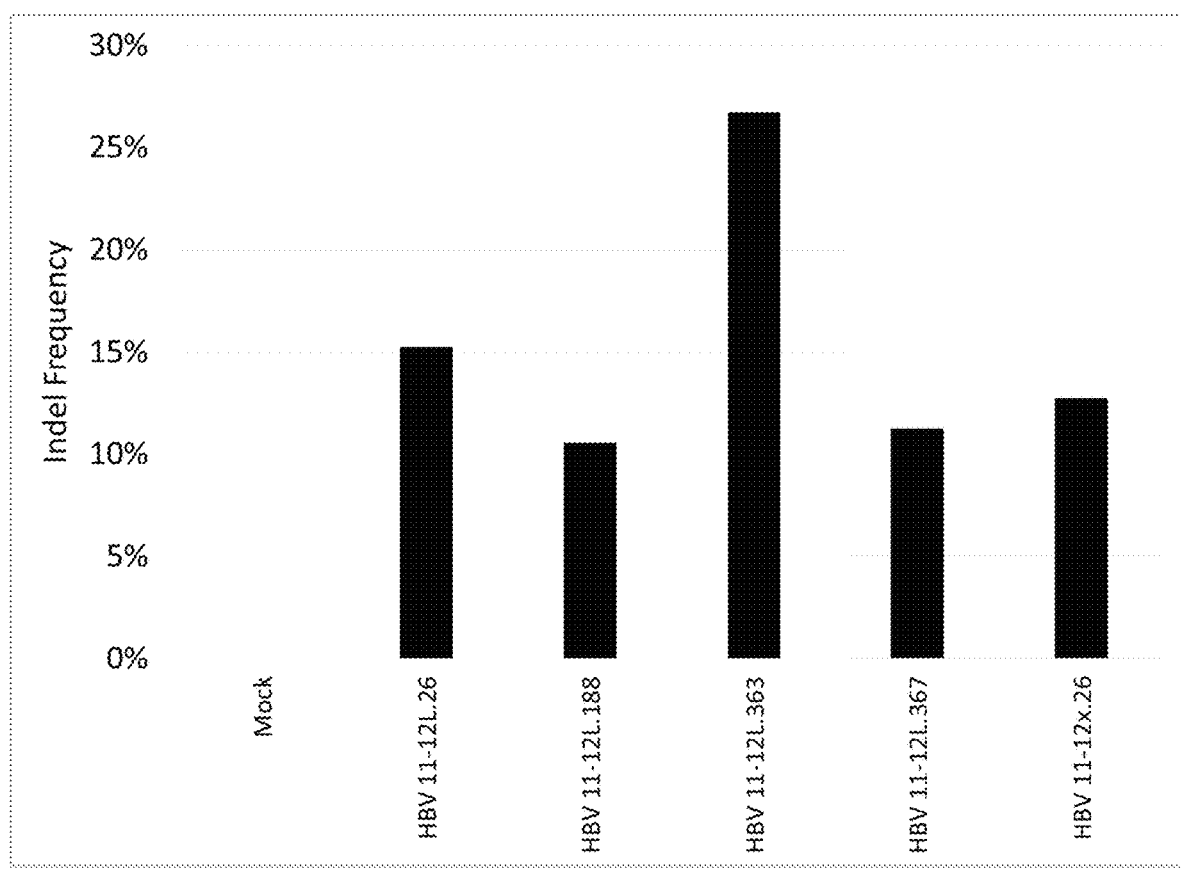
FIG. 14. Efficiency of indel formation detected by digital PCR. HepG2 HepB cells were transfected with mRNA encoding HBV 11-12L.26, HBV 11-12L.188, HBV 11-12L.363, HBV 11-12L.367, or HBV 11-12×.26, respectively. At two days post-transfection, genomic DNA was isolated from cells for analysis of indel formation by digital PCR. Genomic DNA from mock transfected HepG2 HepB cells was used as a control. Digital PCR was performed using the QX200 droplet digital PCR system. A FAM-tagged TaqMan probe was designed to recognize the HBV 11-12 meganuclease target site, as well as a HEX-tagged TaqMan probe that binds genomic sequence ~100 bp downstream of the target site. The probes were multiplexed for genomic DNA amplification. Droplets were gated by fluorescence amplitude to indicate double-positive, double-negative, and single-positive populations. Indels were calculated as the number of HEX-positive droplets divided by the number of double-positive (FAM+/HEX+) droplets.

Genomic DNA from cells treated with HBV 11-12 meganucleases showed 11-27% gene editing at the recognition site (FIG. 14). In agreement with the T7E data, genomic DNA from HBV 11-12L.363-treated cells advantageously yielded the highest efficiency of indel formation at 27%, while the first-generation HBV 11-12×.26 produced 13% indel formation, suggesting enhanced (i.e., increased) activity of the optimized HBV 11-12L.363 meganuclease.

Together, these data indicate an ability of HBV 11-12 meganucleases to achieve 11-27% indel formation at their recognition site. Furthermore, HBV 11-12L.363 shows enhanced (i.e., increased) activity for indel formation compared to the first-generation HBV 11-12×.26 meganuclease.

Example 3

Indel Frequency in HepG2 HepB Cells after Electroporation with HBV 11-12 mRNA

Further studies were conducted to evaluate the production of indels in HepG2 HepB cells following transfection with mRNA encoding the HBV 11-12×.26 or HBV 11-12L.363 meganucleases. HepG2 HepB cells described in Example 2 were electroporated with meganuclease-encoding mRNA according to the same protocols as above. In this experiment, two different mRNA batches encoding the HBV 11-12L.363 meganucleases were evaluated. Cells were electroporated with mRNA encoding either HBV 11-12×.26 (3605), a previously prepared batch of mRNA encoding HBV 11-12L.363 (3129), or a new batch of mRNA encoding HBV 11-12L.363 (3606). An mRNA encoding GFP was also electroporated into cells to serve as a transfection control. GFP-transfected cells were analyzed by flow cytometry, and transfection efficiency exceeded 90%. Cells were collected at 2 days and 6 days post-transfection, and subjected to gDNA isolation and ddPCR analysis as previously described in Example 2. Indel frequency was determined from ddPCR analysis.

Figure 15:
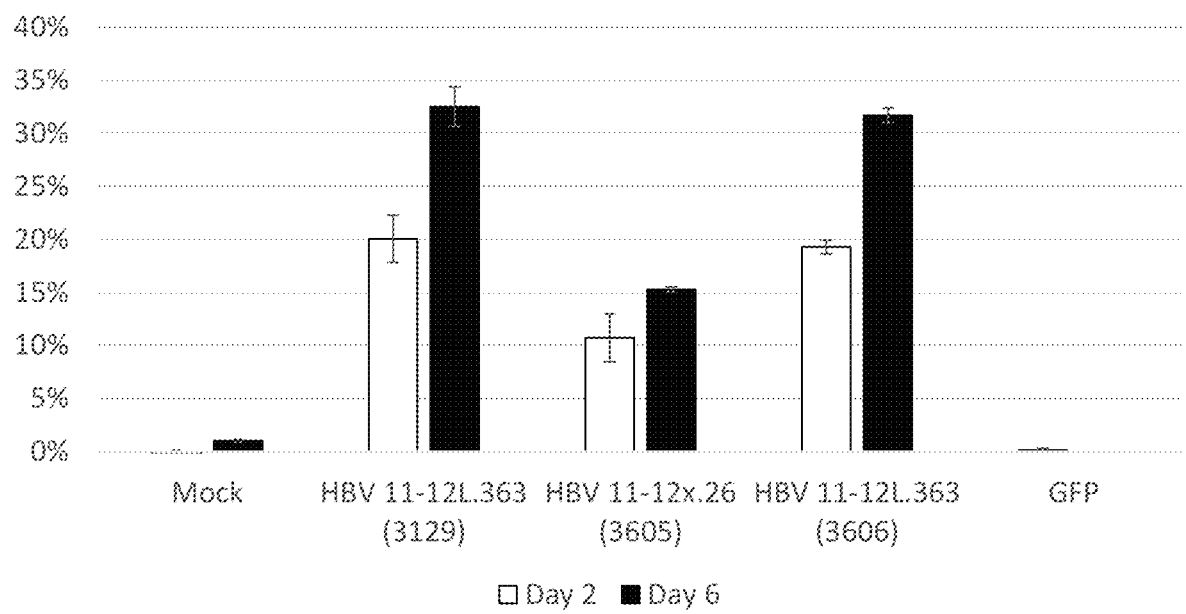
FIG. 15. Indel frequency in HepG2 HepB cells after electroporation with HBV 11-12 mRNA. HepG2 HepB cells were transfected with two different lots of mRNA (3129 and 3606) encoding HBV 11-12L.363 and one lot of mRNA encoding HBV 11-12x.26. At two days and six days post-transfection, genomic DNA was isolated from cells for analysis of indel formation by digital PCR. Genomic DNA from mock transfected HepG2 HepB cells was used as a control. Digital PCR was performed using the QX200 droplet digital PCR system. A FAM-tagged TaqMan probe was designed to recognize the HBV 11-12 meganuclease target site, as well as a HEX-tagged TaqMan probe that binds genomic sequence ~100 bp downstream of the target site. The probes were multiplexed for genomic DNA amplification. Droplets were gated by fluorescence amplitude to indicate double-positive, double-negative, and single-positive populations. Indels were calculated as the number of HEX-positive droplets divided by the number of double-positive (FAM+/HEX+) droplets.

Data obtained from ddPCR demonstrated that HBV 11-12L.363, which was optimized from HBV 11-12×.26, shows ~20% indels 2 days post-transfection, and ~33% indels at 6 days post-transfection (FIG. 15). Two batches of mRNA encoding HBV 11-12L.363 (3129 and 3606) were tested and showed consistent levels of indel formation. Each of these were superior to the level of indel formation observed using HBV 11-12×.26, which showed ~10% and 15% indels at 2 days and 6 days post-transfection, respectively.

Together these data suggest that the HBV 11-12L.363 nuclease is significantly more active in producing indels at the HBV 11-12 recognition sequence than the previous generation nuclease, HBV 11-12×.26. Furthermore, consistent levels of indels were observed between mRNA batches of HBV 11-12L.363.

Example 4

In Vitro Antiviral Evaluation of HBV 11-12L.363 in HBV-Integrated HepAD38 Cells by mRNA Expression Studies were conducted to evaluate the antiviral activities of HBV 11-12 meganuclease and efficacy for insertions and/or deletions ("indels") at their intended recognition sequence in HBV-integrated HepAD38 cells. Antiviral activity, secreted HBs antigen was measured by Hepatitis B Surface Antigen Chemiluminescence Immunoassay (CLIA) kit. Indel formation was detected by GeneART Genomic Cleavage Detection kit.

In this study, a HepAD38 cell line which expresses wild-type HBV, subtype ayw (Ladner, S K et al. "Inducible expression of human hepatitis B virus (HBV) in stably transfected hepatoblastoma cells: a novel system for screening potential inhibitors of HBV replication." *Antimicrobial agents and chemotherapy*vol. 41, 8 (1997): 1715-20.) was maintained in Dulbecco's modified Eagle's/F12 medium (DMEM/F12; Thermo Fisher) supplemented with 2% fetal bovine serum, 500 µg/ml of Penicillin-Streptomycin-Glutamine, 0.3 µg/ml tetracycline, 10 mM HEPES, lx MEM Non-Essential Amino Acids and 1% Dimethyl sulfoxide at 37° C. and 5% carbon dioxide. HepAD38 (1.5×10^6) cells were transfected with mRNA (3 ug) encoding HBV 11-12L.363, HBV 11-12×.26 and mCherry (TriLink), respectively, by using the Lipofectamine MessengerMAX (Thermo Fisher), TransIT-mRNA (Mirus), and jetMESSENGER (Polyplus) according to the manufacturer's instructions.

HepAD38 (1.5×10-6) cells were also transfected with mRNA (3 ug) formulated in lipid nanoparticles (LNPs). The lipid materials used for the formulation of LNPs consisted of Dlin-MC3-DMA, Cholesterol, DSPC, and DMG-PEG dissolved at a 50:38.5:10:1.5 molar ratio in ethanol at a total lipid concentration of 30 mM (N:P=8). The mix of lipids was stored at −80C and thawed by heating to 50° C. in heat block. Lipid mix was taken off heat and vortexed immediately before use in formulation. mRNA was stored at −80° C. and thawed at room temperature. Once thawed, the mRNA was diluted to 0.2 mg/mL in a 50 mM citrate buffer at pH=4.0. Microfluidic mixing of the mRNA and lipid solutions at a 3:1 ratio via Precision Nanosystems benchtop nanoassembler was performed. Crude solution was transferred to dialysis membrane and placed in 200× volume of PBS, pH=7.4, overnight. Final solution was collected from dialysis membrane and analyzed for physical characteristics such as size, PDI, and zeta potential, as well as for encapsulation efficiency. LNP transfection was performed with or without apolipoprotein E (1 µg/mL).

The mRNA materials encoding the HBV 11-12L.363, HBV 11-12×.26 nucleases comprised a clean cap structure (Trilink) with a uridine substitution to N1-methyl-pseudouridine.

At day 4 and day 6 post-transfection, supernatant was collected for measuring secreted HBs antigen by CLIA assay (AutoBio). To determine the percentage of HBs antigen reduction, mCherry transfected in HepAD38 cells was used as 100% control.

Figure 16:
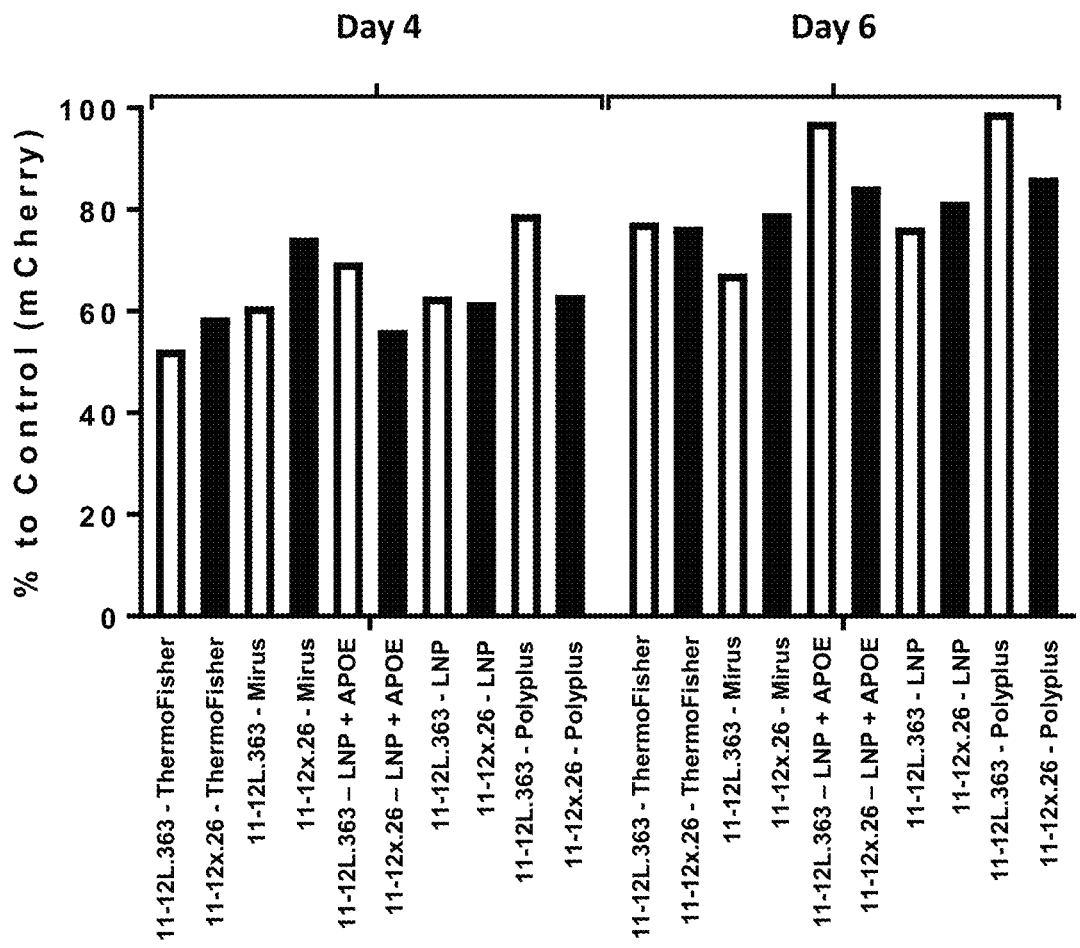
FIG. 16. In vitro antiviral evaluation of HBV 11-12L.363 in HBV-integrated HepAD38 cells. A HepAD38 cell line which expresses wild-type HBV (subtype ayw) was transfected with mRNA (3 ug) encoding HBV 11-12L.363, HBV 11-12x.26, and mCherry (TriLink) respectively, by using the Lipofectamine MessengerMAX (Thermo Fisher), TransIT-mRNA (Mirus), jetMESSENGER (Polyplus), or lipid nanoparticles (Precision BioSciences), each according to the manufacturer's instructions. At day 4 and day 6 post-transfection, supernatant was collected for measuring secreted HBs antigen by CLIA assay (AutoBio). To determine the percentage of HBs antigen reduction, mCherry transfected HepAD38 cells were used as 100% control.

Through mRNA expression, both HBV 11-12L.363 and HBV 11-12×.26 showed similar antiviral activity, reducing ~50% secreted HBs antigen. Four-day post-transfection had a higher effect than that of six-day post-transfection (FIG. 16).

At six-day post-transfection, genomic DNA was isolated from cells for analysis of indel formation by GeneART Genomic Cleavage Detection Kit (Thermo Fisher). Genomic DNA from mCherry transfected in HepAD38 cells was used as a control.

For Genomic Cleavage Detection assay, genomic DNA was PCR amplified using AD38-F1012 and AD38-R1479 primers:

AD38-F1012:
(SEQ ID NO: 31)
[5'-GGTTTTGCTGCCCCATTTACA-3']

AD38-R1479:
(SEQ ID NO: 32)
[5'-TCCCAAGCGACCCCGAGAAG-3']

Amplification was confirmed by the visualization of a ~467 bp band on an agarose gel. PCR-amplified DNA was analyzed in the cleavage assay according to the manufacture's protocol. Digestion products were visualized on an agarose gel.

Figure 17:
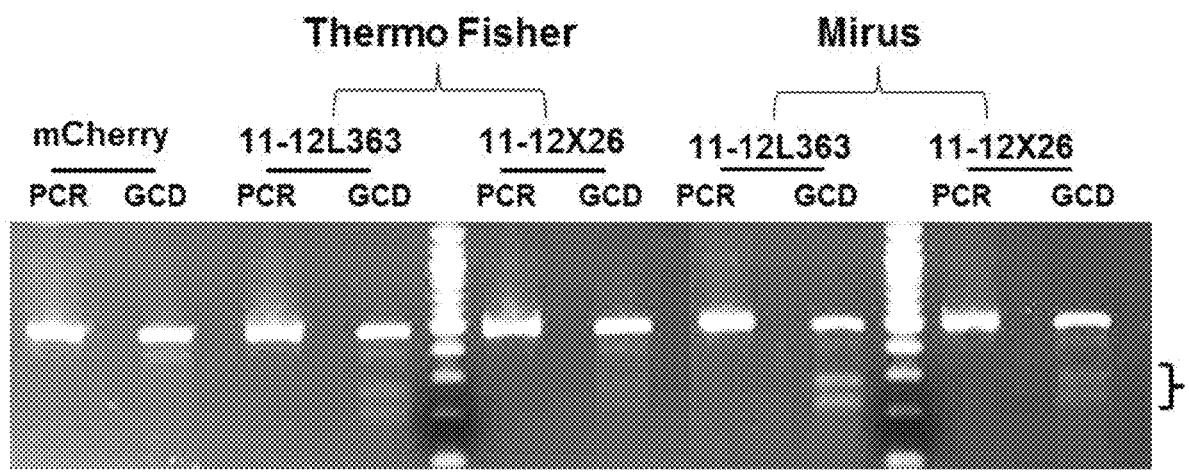
FIG. 17. Detection of indels in HBV 11-12L.363 mRNA-transfected HepAD38 cells. At day six post-transfection of HBV 11-12L.363 mRNA, genomic DNA was isolated from HepAD38 cells for analysis of indel formation by GeneART Genomic Cleavage Detection (GCD) Kit (Thermo Fisher). Genomic DNA from mCherry transfected HepAD38 cells were used as a control. Amplification was confirmed by the visualization of a ~467 bp band on an agarose gel. PCR-amplified DNA was analyzed in the cleavage assay and digestion products were visualized on an agarose gel.

While mCherry-transfected cells yielded a single band at ~467 bp, transfected with HBV 11-12L.363 and HBV 11-12×.26, respectively, yielded two lower molecular weight bands at ~267 bp and ~200 bp after Detection Enzyme digestion, indicating successful gene editing (FIG. 17). Comparing HBV 11-12L.363 with the first-generation HBV 11-12×.26, the increased intensity of lower bands indicates the higher efficiency of gene editing at the target site was achieved.

Overall, HBV 11-12L.363 showed similar antiviral activities as HBV 11-12×.26 in HBV-integrated HepAD38 cells by mRNA expression. Both HBV 11-12 meganuclease were capable of reducing ~50% HBs antigen secretion and achieving significant indels. Although the antiviral activity observed in these studies is lower than reductions observed in previous lentiviral studies with HBV 11-12×.26, these differences could be attributed to lower delivery efficiency of mRNA transfection vs ~100% lentiviral transduction, transient mRNA expression having shorter kinetics than persistent lentiviral expression, in addition to suboptimal timing and assay sensitivity for gene editing efficiency assessment.

The invention claimed is:

1. An engineered meganuclease that recognizes and cleaves a recognition sequence consisting of SEQ ID NO: 10 within a Hepatitis B virus genome, wherein said engineered meganuclease comprises a first subunit and a second subunit, wherein said first subunit binds to a first recognition half-site of said recognition sequence and comprises a first hypervariable (HVR1) region, wherein said second subunit binds to a second recognition half-site of said recognition sequence and comprises a second hypervariable (HVR2) region, wherein said engineered meganuclease comprises the amino acid sequence of SEQ ID NO: 12 or 13.

2. The engineered meganuclease of claim 1, wherein said engineered meganuclease exhibits optimized characteristics selected from the group consisting of improved specificity, enhanced efficiency of cleavage, and enhanced efficiency of indel formation, when compared to the HBV 11-12x.26 meganuclease of SEQ ID NO: 14.

3. A pharmaceutical composition for treatment of a subject having Hepatitis B virus or hepatocellular carcinoma caused by Hepatitis B virus, said pharmaceutical composition comprising a pharmaceutically acceptable carrier and said engineered meganuclease of claim 1.

4. The engineered meganuclease of claim 1, wherein said engineered meganuclease comprises the amino acid sequence of SEQ ID NO: 12.

5. The engineered meganuclease of claim 1, wherein said engineered meganuclease comprises the amino acid sequence of SEQ ID NO: 13.

6. A method for treating a subject having Hepatitis B virus or hepatocellular carcinoma caused by Hepatitis B virus, said method comprising delivering to a target cell in said subject a therapeutically effective amount of said engineered meganuclease of claim 1; wherein said engineered meganuclease recognizes and cleaves said recognition sequence consisting of SEQ ID NO: 10 within the Hepatitis B virus genome, and wherein the infection and/or proliferation of said Hepatitis B virus in said subject is reduced or eliminated.

* * * * *

```
                        SEQUENCE LISTING

<160> NUMBER OF SEQ ID NOS: 33

<210> SEQ ID NO 1
<211> LENGTH: 163
<212> TYPE: PRT
<213> ORGANISM: Chlamydomonas reinhardtii

<400> SEQUENCE: 1

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 2
<211> LENGTH: 9
<212> TYPE: PRT
<213> ORGANISM: Chlamydomonas reinhardtii

<400> SEQUENCE: 2

Leu Ala Gly Leu Ile Asp Ala Asp Gly
1               5

<210> SEQ ID NO 3
<211> LENGTH: 3221
<212> TYPE: DNA
<213> ORGANISM: Hepatitis B virus

<400> SEQUENCE: 3
ttccactgcc ttccaccaag ctctgcagga tcccagagtc aggggtctgt attttcctgc    60
tggtggctcc agttcaggaa cagtaaaccc tgctccgaat attgcctctc acatctcgtc   120
aatctccgcg aggactgggg accctgtggc gaacatggag aacatcacat caggattcct   180
aggacccctg ctcgtgttac aggcggggtt tttcttgttg acaagaatcc tcacaatacc   240
gcagagtcta gactcgtggt ggacttctct caatttccta ggggatcac ccgtgtgtct   300 tggccaaaat tcgcagtccc caacctccaa actcctcacca acctcctgtc ctccaatttg   360
tcctggttat cgctggatgt gtctgcggcg ttttatcata ttcctcttca tcctgctgct   420
```

```
atgcctcatc ttcttattgg ttcttctgga ttatcaaggt atgttgcccg tttgtcctct    480
aattccagga tcaacaacaa ccagtacggg accatgcaaa acctgcacga ctcctgctca    540
aggcaactct atgtttccct catgttgctg tacaaaacct acggatggaa attgcacctg    600
tattcccatc ccatcgtcct gggctttcgc aaaataccta tgggagtggg cctcagtccg    660
tttctcttgg ctcagtttac tagtgccatt tgttcagtgg ttcgtagggc tttcccccac    720
tgtttggctt tcagctatat ggatgatgtg gtattggggg ccaagtctgt acagcatcgt    780
gagtcccttt taccgctgt taccaatttt cttttgtctc tgggtataca tttaaaccct    840
aacaaaacaa aaagatgggg ttattcccta aacttcatgg gttacataat tggaagttgg    900
ggaactttgc cacaggatca tattgtacaa aagatcaaac actgttttag aaaacttcct    960
gttaacaggc ctattgattg aaagtatgt caaagaattg tgggtctttt gggctttgct   1020
gctccattta cacaatgtgg atatcctgcc ttaatgcctt tgtatgcatg tatacaagct   1080
aaacaggctt tcactttctc gccaacttac aaggcctttc taagtaaaca gtacatgaac   1140
ctttaccccg ttgctcggca acggcctggt ctgtgccaag tgtttgctga cgcaacccc    1200 actggctggg gcttggccat aggccatcag cgcatgcgtg gaacctttgt ggctcctctg   1260
ccgatccata ctgcggaact cctagccgct tgttttgctc gcagccggtc tggagcaaag   1320
ctcatcggaa ctgacaattc tgtcgtcctc tcgcggaaat atacatcgtt tccatggctg   1380
ctaggctgtg ctgccaactg gatccttcgc ggaacgtcct ttgtctacgt cccgtcggcg   1440
ctgaatcccg cggacgaccc ctctcggggc gcttgggac tctctcgtcc ccttctccgt   1500
ctgccgttcc agccgaccac ggggcgcacc tctctttacg cggtctcccc gtctgtgcct   1560
tctcatctgc cggtccgtgt gcacttcgct tcacctctgc acgttgcatg gagaccaccg   1620
tgaacgccca tcagatcctg cccaaggtct tacataagag gactcttgga ctcccagcaa   1680
tgtcaacgac cgaccttgag gcctacttca aagactgtgt gtttaaggac tgggaggagc   1740
tgggggagga gattaggtta aaggtctttg tattaggagg ctgtaggcat aaattggtct   1800
gcgcaccagc accatgcaac ttttcacct ctgcctaatc atctcttgta catgtcccac   1860
tgttcaagcc tccaagctgt gccttgggtg gctttgggc atggacattg acccttataa   1920
agaatttgga gctactgtgg agttactctc gttttgcct tctgacttct ttccttccgt   1980
cagagatctc ctagacaccg cctcagctct gtatcgagaa gccttagagt ctcctgagca   2040
ttgctcacct caccatactg cactcaggca agccattctc tgctggggg aattgatgac   2100 tctagctacc tgggtgggta ataatttgga agatccagca tccagggatc tagtagtcaa   2160
ttatgttaat actaacatgg gtttaaagat caggcaacta ttgtggtttc atatatcttg   2220
ccttactttt ggaagagaga ctgtacttga atatttggtc tctttcggag tgtggattcg   2280
cactcctcca gcctatagac caccaaatgc ccctatctta tcaacaattc cggaaactac   2340
tgttgttaga cgacgggacc gaggcaggtc ccctagaaga agaactccct cgcctcgcag   2400
acgcagatct caatcgccgc gtcgcagaag atctcaatct cgggaatctc aatgttagta   2460
ttccttggac tcataaggtg ggaaacttta cggggcttta ttcctctaca gtacctatct   2520
ttaatcctga atggcaaact ccttcctttc ctaagattca tttacaagag gacattatta   2580
ataggtgtca acaatttgtg ggccctctca ctgtaaatga aagagaaga ttgaaattaa   2640 ttatgcctgc tagattctat cctacccaca ctaaatattt gccctagac aaaggaatta   2700 aaccttatta tccagatcag gtagttaatc attacttcca aaccagacat tatttacata   2760
```

| | |
|---|---|
| ctctttggaa ggctggtatt ctatataaga gggaaaccac acgtagcgca tcattttgcg | 2820 |
| ggtcaccata ttcttgggaa caagagctac agcatgggag gttggtcatc aaaacctcgc | 2880 |
| aaaggcatgg ggacgaatct ttctgttccc aaccctctgg gattctttcc cgatcatcag | 2940 |
| ttggaccctg cattcggagc caactcaaac aatccagatt gggacttcaa ccccatcaag | 3000 |
| gaccactggc caacagccaa ccaggtagga gtgggagcat tcgggccagg gctcacccct | 3060 |
| ccacacggcg gtattttggg ggggagccct caggctcagg gcatattgac acagtgtca | 3120 |
| acaattcctc ctcctgcctc caccaatcgg cagtcaggaa ggcagcctac tcccatctct | 3180 |
| ccacctctaa gagacagtca tcctcaggcc atgcagtgga a | 3221 |

<210> SEQ ID NO 4
<211> LENGTH: 3214
<212> TYPE: DNA
<213> ORGANISM: Hepatitis B virus

<400> SEQUENCE: 4

| | |
|---|---|
| tccaccactt tccaccaaac tcttcaagat cccagagtca gggccctgta ctttcctgct | 60 |
| ggtggctcca gttcaggaac agtgagccct gctcagacta ctgtctctgc catatcgtca | 120 |
| atcttatcga agactgggga ccctgtaccg aacatgagaa catcgcatc aggactccta | 180 |
| ggacccctgc tcgtgttaca ggcggggttt tcttgttga caaaaatcct cacaatacca | 240 |
| cagagtctag actcgtggtg gacttctctc aattttctag ggggaamacc cgtgtgtctt | 300 |
| ggccaaaatt cgcagtccca aatctccagt cactcacyaa cctgttgtcc tccaatttgt | 360 |
| cctggttatc gctggatgtg tctgcggcgt tttatcatct tcctytgcat cctgctgcta | 420 |
| tgcctcatct tcttgttggt tcttctggac tatcraggta tgttgcccgt ttgtcctcwa | 480 |
| mttccaggat cawcaacaac cagcaccgga ccatgcaaaa cctgcacgac tcctgctcaa | 540 |
| ggaacctcta tryktccctc atgttgctgt acaaaaccta cggacggaaa ctgcacctgt | 600 |
| attcccatcc catcatcttg ggcttttcgca aaataccta gggagtsggc ctcagyccgt | 660 |
| ttctcttggc tcagtttact agcgccattt gttcagtggt tcgtagggct ttcccccact | 720 |
| gtctggcttt cagttatatg gatgatgtgg tattgggggc caagtctgta caacatcttg | 780 |
| agtccctta tgccgctgtt accaatttyc ttttgtcttt gggtatacay ttgaaccctc | 840 |
| acaaaacaaa aagatgggga tattcccta acttcatggg atatgtaatt gggtgttggg | 900 |
| gcacattgcc acaggaacat attgtacaaa aaatcaaaat gtgttttmgg aaacttcctg | 960 |
| taaacagacc tattgattgg aaagtatgtc aacgaattgt gggtcttttg gggtttgccg | 1020 |
| cccctttcac gcaatgtgga tatcctgctt tratgccttt atatgcatgt atacaagcaa | 1080 |
| aacaggcttt tactttctcg ccaacttaca aggcctttct aagtaaacag tatctgaacc | 1140 |
| tttaccccgt tactcggcaa cggtctggtc tgtgccaagt gtttgctgac gcaaccccca | 1200 |
| ctggttgggg cttggccata ggccwtcagc gcatgcgtgg aacctttgtg tctcctctgc | 1260 |
| cgatccatac tgcggaactc ctagccgctt gttttgctcg cagcaggtct ggggcaaaac | 1320 |
| tcatcgggac tgacaattct gtcgtgctct cccgcaagta tacatcgttc ccatggctgc | 1380 |
| taggctgtgc tgccaactgg atcctgcgcg ggacgtcctt tgtttacgtc ccgtcggcgc | 1440 |
| tgaatcccgc ggacgacccc tccggggcc gcttggggct ctaccgcccg cttctccgcc | 1500 |
| tgttgtaccg tccgaccacg gggcgcacct ctctttacgc ggactccccg tctgtgcctt | 1560 |
| ctcatctrcc ggaccgtgtg cacttcgctt cacctctgca cgtcgcatgg agaccaccgt | 1620 |
| gaacgcccac cggaacctgc ccaaggtctt gcataagagg actcttggac tttccgcaat | 1680 |

| | |
|---|---|
| gtcaacgacc gaccttgagg catacttcaa agactgtgtg tttamtgagt gggaggagtt | 1740 |
| gggggaggag aktaggttaa aggtctttgt actaggaggc tgtaggcata aattggtgtg | 1800 |
| ttcaccagca ccatgcaact ttttcacctc tgcctaatca tctcwtgttc atgtcctact | 1860 |
| gttcaagcct ccaagctgtg ccttgggtgg ctttagggca tggacattga cccgtataaa | 1920 |
| gaatttggag cttctgtgga gttactctct tttttgcctm mtgacttctt tccttctatt | 1980 |
| cgagatctcc tcgacaccgc ctctgctttg tatcggagg ccttagagtc tccggaacat | 2040 |
| tgttcacctc accatacggc actcaggcaa gctattctgt gttggggtga gttgatgaat | 2100 |
| ctagccacct gggtgggaag taatttggaa gatccagcat ccagggaatt agtmgttagc | 2160 |
| tatgtcaacg ttaatatggg cmtaaaaatc agacaactat tgtggtttca catttcctgt | 2220 |
| cttacttttg ggaragamac tgttcttgaa tatttggtgt cttttggagt gtggattcgc | 2280 |
| actcctcctg catatagacc aycaaatgcc cctatcttat caacacttcc ggaaactact | 2340 |
| gttgttagac gaagaggcag gtcccctaga agaagaactc cctcgcctcg cagacgaagg | 2400 |
| tctcaatcgc cgcgtcgcag aagatctcaa tctcgggaat ctcaatgtta gtattccttg | 2460 |
| gacacataag gtgggaaact ttacggggct ttattcttct acggtacctt gctttaatcc | 2520 |
| taawtggcaa actccttctt ttcctgacat tcatttgcag gaggacattg ttgatagatg | 2580 |
| taagcamttt gtggggcccc ttacagtaaa tgaaaacagg agactaaaat taattatgcc | 2640 |
| tgctaggttt tatcccaatg ttaccaaata tttgccctta gataaaggga tcaaaccttta | 2700 |
| ttatccagag catgtagtta atcattactt ccagacgaga cattatttac ayactctttg | 2760 |
| gaaggcgggt atcytatata aaagagagtc cacacgtagc gcctcatttt gcggatcacc | 2820 |
| atattcttgg gaacaagatc tacagcatgg gaggttggtc ttccaaacct cgaaaaggca | 2880 |
| tggggacaaa tctttctgtc cccaatcccc tgggattctt cccmgatcat cagttggacc | 2940 |
| ctgcattcaa agccaactca saaaatccag attgggacct caacccgcac aaggacaact | 3000 |
| ggccggacgc caacaaggtg ggagtgggag cattcgggcc agggttcatc cctccccatg | 3060 |
| ggggactgtt ggggtggarc cctcaggctc agggcatact cacaactgtg ccagcagctc | 3120 |
| ctcctcctgc ctccaccaat cggcagtcag gaaggcagcc tactccctta tctccacctc | 3180 |
| taagggacac tcatcctcag gccatgcagt ggaa | 3214 |

<210> SEQ ID NO 5
<211> LENGTH: 3214
<212> TYPE: DNA
<213> ORGANISM: Hepatitis B virus

<400> SEQUENCE: 5

| | |
|---|---|
| tccacaacat tccaccaagc tctgctagat cccagagtga ggggcctata ttttcctgct | 60 |
| ggtggctcca gttccggaac agtaaaccct gttccgacta ctgcctcacc catatcgtca | 120 |
| atcttctcga ggactgggga ccctgcaccg aacatggaga gcacaacatc aggattccta | 180 |
| ggacccctgc tcgtgttaca ggcggggttt ttcttgttga caagaatcct cacaatacca | 240 |
| cagagtctag actcgtggtg gacttctctc aattttctag gggagcacc cacgtgtcct | 300 |
| ggccaaaatt cgcagtcccc aacctccaat cactcaccaa cctcttgtcc tccaatttgt | 360 |
| cctggctatc gctggatgtg tctgcggcgt tttatcatat tcctcttcat cctgctgcta | 420 |
| tgcctcatct tcttgttggt tcttctggac taccaaggta tgttgcccgt ttgtcctcta | 480 |
| cttccaggaa catcaactac cagcacggga ccatgcaaga cctgcacgat tcctgctcaa | 540 |

-continued

```
ggaacctcta tgtttccctc ttgttgctgt acaaaacctt cggacggaaa ctgcacttgt    600
attcccatcc catcatcctg ggctttcgca agattcctat gggagtgggc cttagtccgt    660
ttctcctggc tcagtttact agtgccattt gttcagtggt tcgcagggct ttcccccact    720
gtttggcttt cagttatatg gatgatgtgg tattgggggc caagtctgta caacatcttg    780
agtccttttt tacctctatt accaattttc ttttgtcgtt gggtatacat ttgaaccctc    840
ataaaaccaa acgttggggc tactcccta acttcatggg atatgtaatt ggaagttggg     900
ggactttacc acaggaacat attgtattaa aaatcaagca atgttttcgg aaactgcctg    960
taaatagacc tattgattgg aaagtatgtc aaagaattgt gggtcttttg ggctttgctg    1020 cccctttac acaatgtggc tatcctgcct tgatgccttt atatgcatgt atacaatcta     1080
agcaggcttt cactttctcg ccaacttaca aggcctttct gtgtcaacaa tacctgcacc    1140
tttaccccgt tgcccggcaa cggtcaggtc tctgccaagt gtttgctgac gcaaccccca    1200
ctggatgggg cttggccata ggccatcggc gcatgcgtgg aacctttgtg gctcctctgc    1260
cgatccatac tgcggaactc ctagcagctt gttttgctcg cagccggtct ggagcaaaac    1320
ttatcgggac tgacaactct gttgtcctct ctcggaaata caacctccttc ccatggctgc    1380 tcgggtgtgc tgccaactgg atcctgcgcg ggacgtcctt tgtctacgtc ccgtcggcgc    1440
tgaatcccgc ggacgacccg tctcggggcc gtttgggcct ctaccgtccc cttcttcatc    1500
tgctgttcca gccgactacg gggcgcacct ctctttacgc ggtctccccg tctgtgcctt    1560
ctcatctgcc ggaccgtgtg cacttcgctt cacctctgca cgtcgcatgg agaccaccgt    1620
gaatgcccac caggtcttgc ccaagctctt acataagagg actcttggac tctcagcaat    1680
gtcaacgacc gaccttgaag catacttcaa agactgtttg tttaaggact gggaggagtt    1740
gggggaggag attaggttaa aggtctttgt actaggaggc tgtaggcata aattggtctg    1800
ttcaccagca ccatgcaact ttttcacctc tgcctaatca tctcatgttc atgtcctact    1860
gttcaagcct ccaagctgtg ccttgggtgg ctttggggca tggacattga cccgtataaa    1920
gaatttggag cttctgtgga gttactctct ttttttgcctt ctgacttctt ccttctatt    1980 cgagatctcc tcgacaccgc ctctgctctg tatcggagg ccttagagtc tccggaacat    2040
tgttcacctc accatacagc actcaggcaa gctattctct gttggggtga gttgatgaat    2100
ctggccacct gggtgggaag taatttggaa gacccagcat ccagggaatt agtagtcagc    2160
tatgtcaatg ttaatatggg cctaaaaatc agacaactat tgtggtttca catttcctgt    2220
cttacttttg gaagagaaac tgttcttgag tatttggtgt cttttggagt gtggattcgc    2280
actcctccag cttacagacc accaaatgcc cctatcttat caacacttcc ggaaactact    2340
gttgttagac gacgaggcag gtcccctaga agaagaactc cctcgcctcg cagacgaagg    2400
tctcaatcgc cgcgtcgcag aagatctcaa tctcgggaat ctcaatgtta gtatcccttg    2460
gactcataag gtgggaaact ttactgggct ttattcttct actgttcctg tctttaatcc    2520
tgagtggcaa actccctcct ttcctaacat tcatttacag gaagacatta ttaatagatg    2580
tcaacaatat gtgggccctc ttacagttaa tgaaaaaagg agattaaaat taattatgcc    2640
tgctaggttc tatcctaacc ttaccaaata tttgcccttg gataaaggca ttaaaccttca   2700 ttatcctgaa catgcagtta atcattactt caaaactagg cattatttac atactctgtg    2760
gaaggctggc attctatata aaagagaaac tacacgcagc gcttcatttt gtgggtcacc    2820
atattcttgg gaacaagagc tacagcatgg gaggttggtc ttccaaacct cgacaaggca    2880
tggggacgaa tctttctgtt cccaatcctc tgggattctt tcccgatcac cagttggacc    2940
```

```
ctgcgttcgg agccaactca aacaatccag attgggactt caaccccaac aaggatcact    3000
ggccagaggc aaatcaggta ggagcgggag cattcgggcc agggttcacc ccaccacacg    3060
gcggtctttt ggggtggagc cctcaggctc agggcatatt gacaacagtg ccagcagcgc    3120
ctcctcctgc ctccaccaat cggcagtcag gaagacagcc tactcccatc tctccacctc    3180
taagagacag tcatcctcag gccatgcagt ggaa                                3214

<210> SEQ ID NO 6
<211> LENGTH: 3182
<212> TYPE: DNA
<213> ORGANISM: Hepatitis B virus

<400> SEQUENCE: 6
ttccacaacc tttcaccaaa ctctgcaaga tcccagagtg agaggcctgt atttccctgc      60
tggtggctcc agttcaggag cagtaaaccc tgttccgact actgcctctc ccttatcgtc     120
aatcttctcg aggattgggg accctgcgct gaacatggag aacatcacat caggattcct     180
aggacccctt ctcgtgttac aggcggggtt tttcttgttg acaagaatcc tcacaatacc     240
gcagagtcta gactcgtggt ggacttctct caattttcta gggggaacta ccgtgtgtct     300
tggccaaaat tcgcagtccc caacctccaa tcactcacca acctcctgtc ctccaacttg     360
tcctggttat cgctggatgt gtctgcggcg ttttatcatc ttcctcttca tcctgctgct     420
atgcctcatc ttcttgttgg ttcttctgga ctatcaaggt atgttgcccg tttgtcctct     480
aattccagga tcctcaacca ccagcacggg accatgccga acctgcatga ctactgctca     540
aggaacctct atgtatccct cctgttgctg taccaaacct tcggacggaa attgcacctg     600
tattcccatc ccatcatcct gggctttcgg aaaattccta tgggagtggg cctcagcccg     660
tttctcctgg ctcagtttac tagtgccatt tgttcagtgg ttcgtagggc tttcccccac     720
tgtttggctt tcagttatat ggatgatgtg gtattggggg ccaagtctgt acagcatctt     780
gagtcccttt ttaccgctgt taccaatttt cttttgtctt gggtataca tttaaacccct     840 aacaaaacaa agagatgggg ttactctctg aattttatgg gttatgtcat tggaagttat     900
gggtccttgc cacaagaaca catcatacaa aaaatcaaag aatgttttag aaaacttcct     960
attaacaggc ctattgattg gaaagtatgt caacgaattg tgggtctttt ggttttgct    1020 gcccccattta cacaatgtgg ttatcctgcg ttaatgccct tgtatgcatg tattcaatct    1080
aagcaggctt tcactttctc gccaacttac aaggcctttc tgtgtaaaca atacctgaac    1140
ctttaccccg ttgcccggca acggccaggt ctgtgccaag tgtttgctga cgcaaccccc    1200
actggctggg gcttggtcat gggccatcag cgcgtgcgtg gaaccttttc ggctcctctg    1260
ccgatccata ctgcggaact cctagccgct tgttttgctc gcagcaggtc tggagcaaac    1320
attatcggga ctgataactc tgttgtcctc tcccgcaaat atacatcgta tccatggctg    1380
ctaggctgtg ctgccaactg gatcctgcgc gggacgtcct tgtttacgt cccgtcggcg    1440 ctgaatcctg cggacgaccc ttctcggggt cgcttgagac tctctcgtcc ccttctccgt    1500
ctgccgttcc gaccgaccac ggggcgcacc tctctttacg cggactcccc gtctgtgcct    1560
tctcatctgc cggaccgtgt gcacttcgct tcacctctgc acgtcgcatg gagaccaccg    1620
tgaacgccca ccgaatgttg cccaaggtct tacataagag gactcttgga ctctctgcaa    1680
tgtcaacgac cgaccttgag gcatacttca aagactgttt gtttaaagac tgggaggagt    1740
tgggggagga gattagatta aaggtctttg tactaggagg ctgtaggcat aaattggtct    1800
```

```
gcgcaccggc gccatgcacc tttttcacct ctgcctaatc atctcttgtt catgtcctac   1860
tgttcaagcc tccaagctgt gccttgggtg gctttgggc atggacatcg acccttataa    1920
agaatttgga gctactgtgg agttactctc gttttttgcct tctgacttct ttccttcagt   1980
acgagatctt ctagataccg cctcagctct gtatcgggaa gccttagagt ctcctgagca    2040
ttgttcacct caccatactg cactcaggca agcaattctt tgctgggggg aactaatgac   2100
tctagctacc tgggtgggtg ttaatttgga agatccagca tctagagacc tagtagtcag   2160
ttatgtcaac actaatatgg gcctaaagtt caggcaactc ttgtggtttc acatttcttg    2220
tctcactttt ggaagagaaa ccgttataga gtatttggtg tctttcggag tgtggattcg   2280
cactcctcca gcttatagac caccaaatgc ccctatccta tcaacacttc cggaaactac    2340
tgttgttaga cgacgaggca ggtcccctag aagaagaact ccctcgcctc gcagacgaag   2400
gtctcaatcg ccgcgtcgca gaagatctca atctcgggaa cctcaatgtt agtattcctt   2460
ggactcataa ggtggggaac tttactggtc tttattcttc tactgtacct gtctttaatc   2520
ctcattggaa aacaccatct tttcctaata tacatttaca ccaagacatt atcaaaaaat    2580
gtgaacagtt tgtaggccca cttacagtta atgagaaaag aagattgcaa ttgattatgc   2640
ctgctaggtt ttatccaaag gttaccaaat atttaccatt ggataagggt attaaacctt    2700
attatccaga acatcagtt aatcattact ccaaactag acactattta cacactctat     2760
ggaaggcggg tatattatat aagagagaaa caacacatag cgcctcattt tgtgggtcac   2820
catattcttg gaacaagat ctacagcatg gggcagaatc tttccaccag caatcctctg    2880
ggattctttc ccgaccacca gttggatcca gccttcagag caaacacagc aaatccagat   2940
tgggacttca atcccaacaa ggacacctgg ccagacgcca acaaggtagg agctggagca   3000
ttcgggctgg gtttcactcc accgcacgga ggccttttgg ggtggagctc tcaggctcag   3060
ggcatactac aaactttgcc agcaaatccg cctcctgcct ccaccaatcg ccagacagga   3120
aggcagccta ccccgctgtc tccacctttg agaaacactc atcctcaggc catgcagtgg   3180
aa                                                                  3182

<210> SEQ ID NO 7
<211> LENGTH: 3212
<212> TYPE: DNA
<213> ORGANISM: Hepatitis B virus

<400> SEQUENCE: 7
ttccacaaca ttccaccaag ctcascagga tcccagagta agrggcctgt atyttcctgc     60
tggtggctcc agttccggaa cagtgaaccc tgttccgact actgcctcac tcatctcgtc    120
aatcttctcg aggattgggg accctgcacc gaacatggaa ggcatcacat caggattcct    180
aggacccctg ctcgtgttac aggcggggtt tttcttgttg acaaaaatcc tcacaatacc    240
gcagagtcta gactcgtggt ggacttctct caattttcya ggggaagctc ccgtgtgtcg    300
tggccaaaat tcgcagtycc caacctccaa tcactcacca acctcttgtc tccaatttg     360 tcctggctat cgctggatgt gtctgcggcg ttttatcatc ttcctcttca tcctgctgct    420
atgcctcatc ttcttgttgg ttcttctgga ctatcaaggt atgttgcccg tttgtcctct    480
aattccagga tcatcaacca ccagtacggg accctgccga acctgcacga ctcttgctca    540
aggaacctct atgtttccct catgttgctg ttcaaaacct tcggacggaa attgcacttg    600
tattcccatc ccatcatcat gggctttcgg aaaattccta tgggagtggg cctcagcccg    660
tttctcctgg ctcagtttac tagtgccatt tgttcagtgg ttcgccgggc tttcccccac    720
```

```
tgtctggctt tcagttatat ggatgatgtg gtattgggggg ccaagtctgt acaacatctt    780
gagtcccttt atacctctgt taccaattt cttttgtctt tgggtataca tttaaatcct    840
aacaaaacaa aaagatgggg atattcccta aatttcatgg gttatgttat tggtagttgg    900
gggtcattac cacaggaaca catcagaatg aaaatcaaag actgttttag aaaactccct    960
gttaaccggc ctattgattg gaaagtatgt caaagaattg tgggtctctt gggctttgct   1020 gccccttta cacaatgtgg atatcctgct ttaatgcctc tgtatgcgtg tattcaatct   1080
aagcaggctt tcactttctc gccaacttac aaggcctttc tgtgtaaaca atacctgaac   1140
ctttaccccg ttgcccggca acggccaggt ctgtgccaag tgtttgctga tgcaaccccc   1200
actggttggg gcttggccat aggccatcag cgcatgcgtg aacctttgy ggctcctctg   1260 ccgatccata ctgcggaact cctggccgct tgttttgctc gcagcaggtc tggagcgaaa   1320
cttattggaa cggataattc tgtcgttctc tcccggaaat atacatcatt tccatggctg   1380
ctaggctgtg ctgccaactg gatcctgcga gggacgtcct ttgtctacgt cccgtcagcg   1440
ctgaatcctg cggacgaccc gtctcggggt cgcttgggga tctatcgtcc ccttctccgt   1500
ctgccgttcc ggccgaccac ggggcgcacc tctctttacg cggtctcccc gtctgtgcct   1560
tctcatctgc cggaccgtgt gcacttcgct tcacctctgc acgtcgcatg gaaaccaccg   1620
tgaacgccca ccaaatcttg cccaaggtct tatataagag gactcttgga ctctctgcaa   1680
tgtcaacgac cgaccttgag gcatacttca aagactgctt gtttaaagac tgggaggagt   1740
tgggggagga gattagatta atgatctttg tactaggagg ctgtaggcat aaattggtct   1800
gcgcaccagc accatgcaac tttttcacct ctgcctaatc atctcttgtt catgtcctac   1860
tgttcaagcc tccaagctgt gccttgggtg gctttaggac atggacattg acccttataa   1920
agaatttgga gctwctgtgg agttactctc ktttttgcct catgacttct ttccttcaat   1980
aagagatctt ctagataccg ccacagctct gtatcgggat gccttagaat ctcctgagca   2040
ttgttcacct caccacacgg cactcaggca agccattctt tgctgggggg atgtaatgaa   2100
tctagctacc tgggtgggtg taaatttgga agatccagca tccagggacc tggtagtcgg   2160
ttatgtcaat actaatatgg gcctaaagtt cagacaatta ttgtggtttc acacttcctg   2220
tctcactttt ggaagagaaa ccgtcttaga gtatttggtg tcttttggag tgtggattcg   2280
cactcctcca ccttatagac caccaaatgc ccctatctta tcaacactc cggagactac   2340 tgttgttaga cgaagaggca ggtcccctag aagaagaact ccctcrcctc gcagacgtag   2400
atctcaatcg ccgcgtcgca gaagatctca atctccagct tcccgatgtt agtattcctt   2460
ggactcacaa ggtgggaaat tttacggggc tttactcttc tactatacct gtctttaatc   2520
ctaactggaa aactccatct tttcctgata ttcatttgca ccaggacatt attaacaaat   2580
gtgaacaatt tgtaggtccc ctaacagtaa atgaaaaacg aagattmaac ttagtcatgc   2640
ctgctagatt ttttcccatc tctacgaaat atttgcctct agagaaaggt ataaaaccct   2700
attatccaga taatgtagtt aatcattact tccaaaccag acactattta catacccctat  2760 ggaaggcggg tatcttatat aaaagagaaa ctgcacgtag cgcctcattt tgtgggtcac   2820
catattcttg ggaacaagag ctacatcatg ggtctttctt ggacggtccc tctcgaatgg   2880
gggaagaatc attccaccac caatcctctg ggatttttc ccgaccacca gttggatcca   2940
gcattcagag caaacaccag aaatccagat tgggaccaca atcccaacaa agaccactgg   3000
acagaagcca acaaggtagg agtgggagca ttcgggccgg ggttcactcc cccacacgga   3060
```

-continued

```
ggccttttgg ggtggagccc tcaggctcaa ggcatgctaa aaacattgcc agcagatccg    3120
cctcctgcct ccaccaatcg gcagtcagga aggcagccta ccccaatcac tccacctttg    3180
agagacactc atcctcaggc catrcagtgg aa                                  3212
```

<210> SEQ ID NO 8
<211> LENGTH: 3205
<212> TYPE: DNA
<213> ORGANISM: Hepatitis B virus

<400> SEQUENCE: 8

```
ttccatcagg ctctgttgga tcccagggta agggctctgt atcttcctgc tggtggctcc      60
agttcaggaa cacaaaaccc tgctccgact attgcctctc tcacatcctc aatcttctcg     120
acgactgggg gccctgctat gaacatggac aacattacat caggactcct aggacccctg     180
ctcgtgttac aggcggtgtg tttcttgttg acaaaaatcc tcacaatacc acagagtcta     240
gactcgtggt ggacttctct caattttcta gggggactac ccgggtgtcc tggccaaaat     300
tcgcagtccc caacctccaa tcacttacca acctcctgtc ctccaacttg tcctggctat     360
cgttggatgt gtctgcggcg ttttatcatc ttcctcttca tcctgctgct atgcctcatc     420
ttcttgttgg ttcttctgga ctaccagggt atgttgcccg tttgtcctct acttccagga     480
tccacgacca ccagcacggg accctgcaaa acctgcacaa ctcttgcaca aggaacctct     540
atgtttccct cctgttgctg ttcaaaaccc tcggacggaa actgcacttg tattcccatc     600
ccatcatcct gggctttagg aaaatacta tgggagtggg cctcagcccg tttctcatgg     660
ctcagtttac tagtgcaatt tgttcagtgg tgcgtagggc tttcccccac tgtctggctt     720
ttagttatat tgatgatctg gtattggggg ccaaatctgt gcagcacctt gagtcccttt     780
ataccgctgt taccaatttt ctgttatctg tgggtatcca tttaaatact tctaaaacta     840
agagatgggg ttacacccta catttatgg gttatgtcat tggtagttgg ggatcattac     900
ctcaagatca tattgtacac aaaatcaaag aatgttttcg gaaactgcct gtaaatcgtc     960
caattgattg gaaagtctgt caacgcattg tgggtctttt gggctttgct gccccttca    1020
cacaatgtgg ttatcctgct ctcatgcctc tgtatgcttg tattactgct aaacaggctt    1080
ttgtttttc gccaacttac aaggcctttc tctgtaaaca atacatgaac ctttaccccg    1140
ttgccaggca acggccgggc ctgtgccaag tgtttgctga cgcaaccccc actggttggg    1200
gcttggccat tggccatcag cgcatgcgtg gaacctttgt ggctcctctg ccgatccata    1260
ctgcggaact cctagcagct tgtttcgctc gcagcaggtc tggagcgact ctcatcggca    1320
cggacaactc tgttgtcctc tctaggaagt acacctcctt cccatggctg ctcgggtgtg    1380
ctgcaaactg gatcctgcgc gggacgtcct ttgtttacgt cccgtcggcg ctgaatcccg    1440
cggacgaccc ctcccggggc cgcttggggc tgtaccgccc tcttctccgt ctgccgttcc    1500
agccgacaac gggtcgcacc tctctttacg cggactcccc gtctgttcct tctcatctgc    1560
cggaccgtgt gcacttcgct tcacctctgc acgtcgcatg gagaccaccg tgaacgcccc    1620
ttggagtttg ccaacagtct tacataagag gactcttgga ctttcaggag ggtcaatgac    1680
ccggattgca gaatacatca aagactgtgt atttaaggac tgggaggagt tgggggagga    1740
gactaggtta atgatctttg tactaggagg ctgtaggcat aaattggtct gttcaccagc    1800
accatgcaac ttttcacct ctgcctaatc atctttgtt catgtcctac tgttcaagcc    1860
tccaagctgt gccttgggtg gctttgggac atggacattg accctataa agaatttggc    1920
gcttctgtgg agttactctc ttttttgcct tctgatttct ttccatcggt tcgggaccta    1980
```

```
ctcgacaccg cttcagccct ttaccgggat gctttagagt cacctgaaca ttgcactccc    2040
catcacactg ccctcaggca agttattttg tgctggggtg agttaatgac tttggcttcc    2100
tgggtgggca ataacttgga agaccctgct gccagggatt tagtagttaa ctatgttaac    2160
actaacatgg gcctaaaaat tagacaacta ctgtggtttc acatttcctg ccttactttt    2220
ggaagagata tagttcttga gtatttggtg tcctttggag tgtggattcg cactcctcct    2280
gcttacagac cacaaaatgc ccctatccta tccacacttc cggaaactac tgttgttaga    2340
cgacgaggca ggtcccctag aagaagaact ccctcgcctc gcagacgaag atctcaatcg    2400
ccgcgtcgcc gaagatctca atctccagct tcccaatgtt agtattcctt ggactcataa    2460
ggtgggaaat tttacggggc tttactcttc tactgtgcct gcttttaatc ctgactggtt    2520
aactccttct tttcctaata ttcatttaca tcaagaccta atttctaaat gtgaacaatt    2580
tgtaggccca ctcactaaaa atgaattaag gaggttaaaa ttggttatgc cagctagatt    2640
ttatcctaag gttaccaaat attttcctat ggagaaagga atcaagcctt attatcctga    2700
gcatgcagtt aatcattact ttaaaacaag acattatttg catactttat ggaaggcggg    2760
aattttatat aagagagaat ccacacgtag cgcatcattt tgtgggtcac catattcctg    2820
ggaacaagag ctacagcatg ggagcacctc tctcaacgac aagaagaggc atgggacaga    2880
atctttctgt gcccaatcct ctgggattct ttccagacca tcagctggat ccgctattca    2940
aagcaaattc cagcagtccc gactgggact tcaacacaaa caaggacagt tggccaatgg    3000
caaacaaggt aggagtggga gcatacggtc cagggttcac accccacac ggtggcctgc    3060 tggggtggag ccctcaggca caaggtatgt taacaacctt gccagcagat ccgcctcctg    3120
cttccaccaa tcggcggtcc gggagaaagc caaccccagt ctctccacct ctaagagaca    3180
ctcatccaca ggcaatgcag tggaa                                         3205

<210> SEQ ID NO 9
<211> LENGTH: 3247
<212> TYPE: DNA
<213> ORGANISM: Hepatitis B virus

<400> SEQUENCE: 9
tctacagcat tccaccaagc tctacaaaat cccaaagtca ggggcctgta ttttcctgct     60
ggtggctcca gttcagggat agtgaaccct gttccgacta ttgcctctca catctcgtca    120
atcttctcca ggattgggga ccctgcaccg aacatggaga acatcacatc aggattccta    180 ggaccctgc tcgtgttaca ggcggggttt tcttgttga caagaatcct cacaataccg    240
cagaatctag actcgtggtg gacttctctc aattttctag ggggagtgcc cgtgtgtcct    300
ggcctaaatt cgcagtcccc aacctccaat cactcaccaa ctcctgtcc tccaacttgt    360 cctggctatc gctggatgtg tctgcggcgt tttatcatat tcctcttcat cctgctgcta    420
tgcctcatct tcttgttggt tcttctggac tatcaaggta tgttgcccgt ttgtcctctg    480
attccaggat cctcgaccac cagtacggga ccctgcaaaa cctgcacgac tcctgctcaa    540
ggcaactcta tgtatccctc atgttgctgt acaaaacctt cggacggaaa ttgcacctgt    600
attcccatcc catcatcttg ggctttcgca aaataccta gggagtgggc ctcagtccgt    660
ttctcttggc tcagtttact agtgccattt gttcagtggt tcgtagggct ttcccccact    720
gtctggcttt cagctatatg gatgatgtgg tattgggggc caaatctgta caacatcttg    780
agtcccttta taccgctgtt accaattttc ttttgtcttt gggtatacat ctaaacccta    840
```

```
acaaaacaaa aagatggggt tattccttaa attttatggg atatgtaatt ggaagttggg    900
gtactttgcc acaagaacac atcacacaga aaattaagca atgttttcgg aaactccctg    960
ttaacaggcc aattgattgg aaagtctgtc aacgaataac tggtctgttg ggtttcgctg    1020
ctccttttac ccaatgtggt taccctgcct aatgccttt atatgcatgt atacaagcta    1080
agcaggcttt tactttctcg ccaacttata aggcctttct ctgtaaacaa tacatgaacc    1140
tttaccccgt tgctaggcaa cggcccggtc tgtgccaagt gtttgctgac gcaaccccca    1200
ctggttgggg cttggccatc ggccatcagc gcatgcgtgg aacctttgtg gctcctctgc    1260
cgatccatac tgcggaactc ctagctgctt gttttgctcg cagccggtct ggagcaaaac    1320
tcattgggac tgacaattct gtcgtccttt ctcggaaata tacatccttt ccatggctgc    1380
taggctgtgc tgccaactgg atccttgcgc ggacgtcctt tgtttacgtc ccgtcagcgc    1440
tgaatccagc ggacgacccc tcccggggcc gtttggggct ctgtcgcccc cttctccgtc    1500
tgccgttcct gccgaccacg gggcgcacct ctctttacgc ggtctccccg tctgttcctt    1560
ctcatctgcc ggaccgtgtg cacttcgctt cacctctgca cgttacatgg aaaccgccat    1620
gaacacctct catcatctgc caaggcagtt atataagagg actcttggac tgtttgttat    1680
gtcaacaacc ggggtggaga aatacttcaa ggactgtgtt tttgctgagt gggaagaatt    1740
aggcaatgag tccaggttaa tgaccttgt attaggagc tgtaggcata aattggtctg    1800
cgcaccagca ccatgtaact ttttcacctc tgcctaatca tctcttgttc atgtcctact    1860
gttcaagcct ccaagctgtg ccttgggtgg ctttagggca tggatagaac aactttgcca    1920
tatgcctttt ttggcttaga cattgaccct tataaagaat ttggagctac tgtggagttg    1980
ctctcgtttt tgccttctga cttttttcccg tctgttcgtg atcttctcga caccgcttca    2040
gctttgtacc gggaatcctt agagtcctct gatcattgtt cgcctcacca tacagcactc    2100
aggcaagcaa tcctgtgctg gggtgagttg atgactctag ccacctgggt gggtaataat    2160
ttggaagatc cagcatccag agatttggtg gtcaattatg ttaatactaa tatgggttta    2220
aaaatcaggc aactattgtg gtttcacatt tcctgtctta cttttgggag agaaaccgtt    2280
cttgagtatt tggtgtcttt tggagtgtgg attcgcactc ctcctgctta tagaccacca    2340
aatgcccta tcctatcaac acttccggag actactgttg ttagacgaag aggcaggtcc    2400
cctcgaagaa gaactccctc gcctcgcaga cgaagatctc aatcgccgcg tcgcagaaga    2460
tctgcatctc cagcttccca atgttagtat tccttggact cacaaggtgg gaaactttac    2520
ggggctgtat tcttctacta tacctgtctt taatcctgat tggcaaactc cttcttttcc    2580
aaatatccat ttgcatcaag acattataac taaatgtgaa caatttgtgg gccctctcac    2640
agtaaatgag aaacgaagat taaaactagt tatgcctgcc agattttttcc caaactctac    2700
taaatattta ccattagaca aaggtatcaa accgtattat ccagaaaatg tagttaatca    2760
ttacttccag accagacatt atttacatac ccttttggaag gcgggtattc tatataagag    2820
agaaacatcc cgtagcgctt cattttgtgg gtcaccatat acttgggaac aagatctaca    2880
gcatggggct ttcttggacg gtccctctcg agtggggaaa gaacctttcc accagcaatc    2940
ctctaggatt ccttcccgat caccagttgg acccagcatt cagagcaaat accaacaatc    3000
cagattggga cttcaatccc aaaaaggacc cttggccaga ggccaacaag gtaggagttg    3060
gagcctatgg acccgggttc acccctccac acggaggcct tttggggtgg agccctcagt    3120
ctcagggcac actaacaact ttgccagcag atccgcctcc tgcctccacc aatcgtcagt    3180
caggggaggca gccgactccc atctctccac cactaagaga cagtcatcct caggccatgc    3240
```

```
                                                  agtggaa                                                    3247

<210> SEQ ID NO 10
<211> LENGTH: 22
<212> TYPE: DNA
<213> ORGANISM: Hepatitis B virus

<400> SEQUENCE: 10
tgccgatcca tactgcggaa ct                                                                                       22

<210> SEQ ID NO 11
<211> LENGTH: 22
<212> TYPE: DNA
<213> ORGANISM: Hepatitis B virus

<400> SEQUENCE: 11
acggctaggt atgacgcctt ga                                                                                       22

<210> SEQ ID NO 12
<211> LENGTH: 354
<212> TYPE: PRT
<213> ORGANISM: Artificial Sequence
<220> FEATURE:
<223> OTHER INFORMATION: Synthesized

<400> SEQUENCE: 12

Met Asn Thr Lys Tyr Asn Lys Glu Phe Leu Leu Tyr Leu Ala Gly Phe
1               5                   10                  15

Val Asp Gly Asp Gly Ser Ile Asn Ala Ala Ile Ala Pro Arg Gln Ser
            20                  25                  30

Phe Lys Phe Lys His Gly Leu Lys Leu Arg Phe Glu Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Asn Gly Ser Val Ser Val Tyr Cys Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ser Ile Arg Pro Arg Gln His Ala
    210                 215                 220

Lys Phe Lys His Asp Leu Glu Leu Ile Phe Asn Val Arg Gln Leu Thr
225                 230                 235                 240

Ser Arg Arg Trp Phe Leu Asp Lys Leu Val Asp Glu Ile Gly Val Gly
```

```
                    245                 250                 255
Tyr Val Ile Asp Trp Gly Gly Ala Ser Thr Tyr Lys Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 13
<211> LENGTH: 354
<212> TYPE: PRT
<213> ORGANISM: Artificial Sequence
<220> FEATURE:
<223> OTHER INFORMATION: Synthesized

<400> SEQUENCE: 13

Met Asn Thr Lys Tyr Asn Lys Glu Phe Leu Leu Tyr Leu Ala Gly Phe
1               5                   10                  15

Val Asp Gly Asp Gly Ser Ile Asn Ala Cys Ile Ala Pro Arg Gln Ser
                20                  25                  30

Phe Lys Phe Lys His Gly Leu Lys Leu Arg Phe Glu Val Gly Gln Lys
            35                  40                  45

Thr Gln Arg Arg Trp Phe Leu Asp Lys Leu Val Asp Glu Ile Gly Val
        50                  55                  60

Gly Tyr Val Tyr Asp Asn Gly Ser Val Ser Val Tyr Ala Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ser Ile Arg Pro Arg Gln His Ala
210                 215                 220

Lys Phe Lys His Asp Leu Glu Leu Ile Phe Asn Val Arg Gln Lys Thr
225                 230                 235                 240

Asn Arg Arg Trp Phe Leu Asp Lys Leu Val Asp Glu Ile Gly Val Gly
                245                 250                 255
```

```
Tyr Val Ile Asp Trp Arg Asn Cys Ser Thr Tyr Lys Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 14
<211> LENGTH: 354
<212> TYPE: PRT
<213> ORGANISM: Artificial Sequence
<220> FEATURE:
<223> OTHER INFORMATION: Synthesized

<400> SEQUENCE: 14

Met Asn Thr Lys Tyr Asn Lys Glu Phe Leu Leu Tyr Leu Ala Gly Phe
1               5                   10                  15

Val Asp Gly Asp Gly Ser Ile Asn Ala Ser Ile Ala Pro Arg Gln Ser
            20                  25                  30

Phe Lys Phe Lys His Gly Leu Lys Leu Arg Phe Glu Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Asn Gly Ser Val Ser Val Tyr Ser Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ser Ile Arg Pro Arg Gln Tyr Ala
    210                 215                 220

Lys Phe Lys His Asp Leu Glu Leu Arg Phe Asn Val Arg Gln Lys Thr
225                 230                 235                 240

Gln Arg Arg Trp Phe Leu Asp Lys Leu Val Asp Glu Ile Gly Val Gly
                245                 250                 255
```

```
Tyr Val Val Asp Trp Gly Ser Val Ser Thr Tyr Gln Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 15
<211> LENGTH: 147
<212> TYPE: PRT
<213> ORGANISM: Artificial Sequence
<220> FEATURE:
<223> OTHER INFORMATION: Synthesized

<400> SEQUENCE: 15

Lys Glu Phe Leu Leu Tyr Leu Ala Gly Phe Val Asp Gly Asp Gly Ser
1               5                   10                  15

Ile Tyr Ala Ser Ile Arg Pro Arg Gln His Ala Lys Phe Lys His Asp
            20                  25                  30

Leu Glu Leu Ile Phe Asn Val Arg Gln Leu Thr Ser Arg Arg Trp Phe
        35                  40                  45

Leu Asp Lys Leu Val Asp Glu Ile Gly Val Gly Tyr Val Ile Asp Trp
    50                  55                  60

Gly Gly Ala Ser Thr Tyr Lys Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 16
<211> LENGTH: 147
<212> TYPE: PRT
<213> ORGANISM: Artificial Sequence
<220> FEATURE:
<223> OTHER INFORMATION: Synthesized

<400> SEQUENCE: 16

Lys Glu Phe Leu Leu Tyr Leu Ala Gly Phe Val Asp Gly Asp Gly Ser
1               5                   10                  15

Ile Tyr Ala Ser Ile Arg Pro Arg Gln His Ala Lys Phe Lys His Asp
            20                  25                  30

Leu Glu Leu Ile Phe Asn Val Arg Gln Lys Thr Asn Arg Arg Trp Phe
        35                  40                  45
```

```
Leu Asp Lys Leu Val Asp Glu Ile Gly Val Gly Tyr Val Ile Asp Trp
    50              55                  60

Arg Asn Cys Ser Thr Tyr Lys Leu Ser Glu Ile Lys Pro Leu His Asn
65              70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
    130                 135                 140

Val Leu Asp
145

<210> SEQ ID NO 17
<211> LENGTH: 147
<212> TYPE: PRT
<213> ORGANISM: Artificial Sequence
<220> FEATURE:
<223> OTHER INFORMATION: Synthesized

<400> SEQUENCE: 17

Lys Glu Phe Leu Leu Tyr Leu Ala Gly Phe Val Asp Gly Asp Gly Ser
1               5                   10                  15

Ile Tyr Ala Ser Ile Arg Pro Arg Gln Tyr Ala Lys Phe Lys His Asp
                20                  25                  30

Leu Glu Leu Arg Phe Asn Val Arg Gln Lys Thr Gln Arg Trp Phe
            35                  40                  45

Leu Asp Lys Leu Val Asp Glu Ile Gly Val Gly Tyr Val Val Asp Trp
    50              55                  60

Gly Ser Val Ser Thr Tyr Gln Leu Ser Gln Ile Lys Pro Leu His Asn
65              70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
    130                 135                 140

Val Leu Asp
145

<210> SEQ ID NO 18
<211> LENGTH: 147
<212> TYPE: PRT
<213> ORGANISM: Artificial Sequence
<220> FEATURE:
<223> OTHER INFORMATION: Synthesized

<400> SEQUENCE: 18

Lys Glu Phe Leu Leu Tyr Leu Ala Gly Phe Val Asp Gly Asp Gly Ser
1               5                   10                  15

Ile Asn Ala Ala Ile Ala Pro Arg Gln Ser Phe Lys Phe Lys His Gly
                20                  25                  30

Leu Lys Leu Arg Phe Glu Val Gly Gln Lys Thr Gln Arg Arg Trp Phe
            35                  40                  45
```

```
Leu Asp Lys Leu Val Asp Glu Ile Gly Val Gly Tyr Val Tyr Asp Asn
        50                  55                  60

Gly Ser Val Ser Val Tyr Cys Leu Ser Gln Ile Lys Pro Leu His Asn
 65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
        130                 135                 140

Val Leu Asp
145

<210> SEQ ID NO 19
<211> LENGTH: 147
<212> TYPE: PRT
<213> ORGANISM: Artificial Sequence
<220> FEATURE:
<223> OTHER INFORMATION: Synthesized

<400> SEQUENCE: 19

Lys Glu Phe Leu Leu Tyr Leu Ala Gly Phe Val Asp Gly Asp Gly Ser
  1               5                  10                  15

Ile Asn Ala Cys Ile Ala Pro Arg Gln Ser Phe Lys Phe Lys His Gly
                20                  25                  30

Leu Lys Leu Arg Phe Glu Val Gly Gln Lys Thr Gln Arg Arg Trp Phe
            35                  40                  45

Leu Asp Lys Leu Val Asp Glu Ile Gly Val Gly Tyr Val Tyr Asp Asn
        50                  55                  60

Gly Ser Val Ser Val Tyr Ala Leu Ser Gln Ile Lys Pro Leu His Asn
 65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
                115                 120                 125

Leu Asn Asp Ser Lys Thr Arg Lys Thr Thr Ser Glu Thr Val Arg Ala
        130                 135                 140

Val Leu Asp
145

<210> SEQ ID NO 20
<211> LENGTH: 147
<212> TYPE: PRT
<213> ORGANISM: Artificial Sequence
<220> FEATURE:
<223> OTHER INFORMATION: Synthesized

<400> SEQUENCE: 20

Lys Glu Phe Leu Leu Tyr Leu Ala Gly Phe Val Asp Gly Asp Gly Ser
  1               5                  10                  15

Ile Asn Ala Ser Ile Ala Pro Arg Gln Ser Phe Lys Phe Lys His Gly
                20                  25                  30

Leu Lys Leu Arg Phe Glu Val Gly Gln Lys Thr Gln Arg Arg Trp Phe
```

-continued

```
                35                  40                  45
Leu Asp Lys Leu Val Asp Glu Ile Gly Val Gly Tyr Val Tyr Asp Asn
         50                  55                  60

Gly Ser Val Ser Val Tyr Ser Leu Ser Gln Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 21
<211> LENGTH: 22
<212> TYPE: DNA
<213> ORGANISM: Hepatitis B virus

<400> SEQUENCE: 21
gatgatgtgg tattgggggc ca                                          22

<210> SEQ ID NO 22
<211> LENGTH: 22
<212> TYPE: DNA
<213> ORGANISM: Hepatitis B virus

<400> SEQUENCE: 22
ctactacacc ataaccccg gt                                           22

<210> SEQ ID NO 23
<211> LENGTH: 22
<212> TYPE: DNA
<213> ORGANISM: Homo sapiens

<400> SEQUENCE: 23
ttcctcccca tactgcggaa ct                                          22

<210> SEQ ID NO 24
<211> LENGTH: 22
<212> TYPE: DNA
<213> ORGANISM: Homo sapiens

<400> SEQUENCE: 24
tgccgatcca tactgatgaa aa                                          22

<210> SEQ ID NO 25
<211> LENGTH: 33
<212> TYPE: DNA
<213> ORGANISM: Artificial Sequence
<220> FEATURE:
<223> OTHER INFORMATION: Synthesized

<400> SEQUENCE: 25 gccattttc ataagtgtta acttccgctc ctc                               33

<210> SEQ ID NO 26
<211> LENGTH: 32
<212> TYPE: DNA
```

```
<213> ORGANISM: Artificial Sequence
<220> FEATURE:
<223> OTHER INFORMATION: Synthesized

<400> SEQUENCE: 26
cgtgcagtca ctatggatca actacttaga tg                                    32

<210> SEQ ID NO 27
<211> LENGTH: 19
<212> TYPE: DNA
<213> ORGANISM: Artificial Sequence
<220> FEATURE:
<223> OTHER INFORMATION: Synthesized

<400> SEQUENCE: 27
ggtctgtgcc aagtgtttg                                                   19

<210> SEQ ID NO 28
<211> LENGTH: 19
<212> TYPE: DNA
<213> ORGANISM: Artificial Sequence
<220> FEATURE:
<223> OTHER INFORMATION: Synthesized

<400> SEQUENCE: 28
gtagacaaag gacgttccg                                                   19

<210> SEQ ID NO 29
<211> LENGTH: 22
<212> TYPE: DNA
<213> ORGANISM: Artificial Sequence
<220> FEATURE:
<223> OTHER INFORMATION: Synthesized

<400> SEQUENCE: 29
tgccgatcca tactgcggaa ct                                               22

<210> SEQ ID NO 30
<211> LENGTH: 23
<212> TYPE: DNA
<213> ORGANISM: Artificial Sequence
<220> FEATURE:
<223> OTHER INFORMATION: Synthesized

<400> SEQUENCE: 30
cacagcctag cagccatgga aac                                              23

<210> SEQ ID NO 31
<211> LENGTH: 21
<212> TYPE: DNA
<213> ORGANISM: Artificial Sequence
<220> FEATURE:
<223> OTHER INFORMATION: Synthesized

<400> SEQUENCE: 31
ggttttgctg ccccatttac a                                                21

<210> SEQ ID NO 32
<211> LENGTH: 20
<212> TYPE: DNA
<213> ORGANISM: Artificial Sequence
<220> FEATURE:
<223> OTHER INFORMATION: Synthesized

<400> SEQUENCE: 32
tcccaagcga ccccgagaag                                                  20
```

```
<210> SEQ ID NO 33
<211> LENGTH: 42
<212> TYPE: PRT
<213> ORGANISM: Artificial Sequence
<220> FEATURE:
<223> OTHER INFORMATION: Synthesized

<400> SEQUENCE: 33

Ser Leu Pro Gly Ser Val Gly Gly Leu Ser Pro Ser Gln Ala Ser Ser
1               5                   10                  15

Ala Ala Ser Ser Ala Ser Ser Ser Pro Gly Ser Gly Ile Ser Glu Ala
                20                  25                  30

Leu Arg Ala Gly Ala Gly Ser Gly Thr Gly
            35                  40
```